(12) United States Patent
Emtage et al.

(10) Patent No.: US 12,065,498 B2
(45) Date of Patent: Aug. 20, 2024

(54) METHODS OF MAKING BISPECIFIC ANTI-CD307E AND ANTI-BCMA CHIMERIC ANTIGEN RECEPTORS AND USES OF THE SAME

(71) Applicant: Cell Design Labs, Inc., Emeryville, CA (US)

(72) Inventors: Peter Emtage, Lafayette, CA (US); Stephen Santoro, Daly City, CA (US); Stephanie Secrest, San Francisco, CA (US)

(73) Assignee: Cell Design Labs, Inc., Emeryville, CA (US)

( * ) Notice: Subject to any disclaimer, the term of this patent is extended or adjusted under 35 U.S.C. 154(b) by 643 days.

(21) Appl. No.: 16/144,003

(22) Filed: Sep. 27, 2018

(65) Prior Publication Data

US 2019/0194340 A1    Jun. 27, 2019

Related U.S. Application Data

(60) Provisional application No. 62/566,025, filed on Sep. 29, 2017.

(51) Int. Cl.
| | |
|---|---|
| *C07K 16/28* | (2006.01) |
| *A61K 35/17* | (2015.01) |
| *A61K 39/00* | (2006.01) |
| *A61P 35/00* | (2006.01) |
| *C07K 14/00* | (2006.01) |
| *C07K 14/705* | (2006.01) |
| *C07K 14/725* | (2006.01) |
| *A61K 38/00* | (2006.01) |

(52) U.S. Cl.
CPC .......... *C07K 16/2878* (2013.01); *A61K 35/17* (2013.01); *A61K 39/0011* (2013.01); *A61P 35/00* (2018.01); *C07K 14/00* (2013.01); *C07K 14/7051* (2013.01); *C07K 14/70517* (2013.01); *C07K 14/70521* (2013.01); *C07K 14/70578* (2013.01); *C07K 16/283* (2013.01); *A61K 38/00* (2013.01); *A61K 2039/5156* (2013.01); *A61K 2039/5158* (2013.01); *C07K 2317/31* (2013.01); *C07K 2317/56* (2013.01); *C07K 2317/622* (2013.01); *C07K 2319/02* (2013.01); *C07K 2319/03* (2013.01); *C07K 2319/30* (2013.01); *C07K 2319/33* (2013.01)

(58) Field of Classification Search
CPC ............ C07K 16/2878; C07K 14/7051; C07K 16/283; C07K 2317/622; C07K 2319/03; A61P 35/00; A61K 35/17
See application file for complete search history.

(56) References Cited

U.S. PATENT DOCUMENTS

2013/0089555 A1 * 4/2013 Elkins .................. A61K 31/568
424/136.1

FOREIGN PATENT DOCUMENTS

| WO | WO-2012163805 A1 * | 12/2012 | ......... A61K 47/6817 |
|---|---|---|---|
| WO | 2014127261 | 8/2014 | |
| WO | 2014134165 | 9/2014 | |
| WO | 2015142675 | 9/2015 | |
| WO | 2015150526 | 10/2015 | |
| WO | 2016014565 A2 | 1/2016 | |
| WO | 2016014789 A2 | 1/2016 | |
| WO | 2016090337 A1 | 6/2016 | |
| WO | 2016130598 A1 | 8/2016 | |

OTHER PUBLICATIONS

Barrett et al., "Chimeric Antigent Receptor Therapy for Cancer," Annu Rev Med, vol. 65, (2014), pp. 333-347.
Cartellieri et al., "Chimeric Antigen Receptor-Engineered T Cells for Immunotherapy of Cancer," Journal of Biomedicine and Biotechnology, vol. 2010, (2010), pp. 1-13.
Cheadle et al., "CAR T Cells: Driving the Road from the Laboratory to the Clinic," Immunological Reviews, vol. 257, (2014), pp. 91-106.
Chen et al., "Fusion Protein Linkers: Property, Design and Functionality," Adv Drug Deliv Rev, vol. 65, No. 10, (2013), pp. 1-32.
Chiu et al., "Hodgkin Lymphoma Cells Express TACI and BCMA Receptors and Generate Survival and Proliferation Signals in Response to BAFF and APRIL," Blood, vol. 109, No. 2, (2007), pp. 729-739.
Cromie et al., "Nanobodies and Their Use in GPCR Drug Discovery," Current Topics in Medicinal Chemistry, vol. 15, (2015), pp. 2543-2557.
De Genst et al., "Antibody Repertoire Development in Camelids," Developmental and Comparative Immunology, vol. 30, (2006), pp. 187-198.
De Meyer et al., "Nanobody-Based Products as Research and Diagnostic Tools," Trends in Biotechnology, vol. 32, No. 5, (2014), pp. 263-270.
Deshayes et al., "Abnormal Production of the TNF-Homologue APRIL Increases the Proliferation of Human Malignant Glioblastoma Cell Lines via a Specific Receptor," Oncogene, vol. 23, (2004), pp. 3005-3012.
Federov et al., "PD-1- and CTLA-4-Based Inhibitory Chimeric Antigen Receptors (iCARs) Divert Off-Target Immunotherapy Responses," Sci Transl Med., vol. 5, No. 215, (2013), pp. 1-25.
Glienke et al., "Advantages and Applications of CAR-Expressing Natural Killer Cells," Frontiers in Pharmacology, vol. 8, (2015), pp. 1-7.
Eshhar et al., "Specific Activation and Targeting of Cytotoxic Lymphocytes Through Chimeric Single Chains Consisting of Antibody-Binding Domains and the γ or ζ Subunits of the Immunoglobulin and T-cell Receptors," Proc. Natl. Acad. Sci. USA, vol. 90, (1993), pp. 720-724.
Elkins et al., "FcRL5 as a Target of Antibody-Drug Conjugates for the Treatment of Multiple Myeloma," Mol Cancer Ther., vol. 11, No. 10, (2012), pp. 2222-2232.

(Continued)

*Primary Examiner* — Amy E Juedes
*Assistant Examiner* — Brian Hartnett

(57) ABSTRACT

Provided herein are chimeric antigen receptors that binds specifically to B-cell maturation antigen (BCMA) and CD307e, nucleic acids that encode these chimeric antigen receptors, and methods of making and using these chimeric antigen receptors.

11 Claims, 16 Drawing Sheets

Specification includes a Sequence Listing.

(56) References Cited

OTHER PUBLICATIONS

Ise et al., "Elevation of Soluble CD307 (IRTA2/FcRH5) Protein in the Blood and Expression on Malignant Cells of Patients with Multiple Myeloma, Chronic Lymphocytic Leukemia, and Mantle Cell Lymphoma," Leukemia, vol. 21, (2007), pp. 169-174.
Janik, "Tumor Markers in Hairy Cell Leukemia," Leukemia and Lymphoma, vol. 52, No. S2, (2011), pp. 69-71.
Kakarla et al., "CAR T Cells for Solid Tumors: Armed and Ready to Go?" Cancer J., vol. 20, No. 2, (2014), pp. 1-11.
Mackay et al., "BAFF and APRIL: A Tutorial on B Cell Survival," Annu. Rev. Immunol., vol. 21, (2003), pp. 231-264.
Kalled, "The Role of BAFF in Immune Function and Implications for Autoimmunity," Immunological Reviews, vol. 204, (2005), pp. 43-54.
Kijanka et al., "Nanobody-Based Cancer Therapy of Solid Tumors," Nanomedicine, vol. 10, No. 1, (2015), pp. 161-174.
Kershaw et al., "Supernatural T Cells: Genetic Modification of T Cells for Cancer Therapy," Nature, vol. 5, (2005), pp. 928-940.
Kovaleva et al., "Shark Variable New Antigen Receptor Biologics—a Novel Technology Platform for Therapeutic Drug Development," Expert Opin. Biol. Ther., vol. 14, No. 10, (2014), pp. 1527-1539.
Krah et al., "Single Domain Antibodies for Biomedical Applications," Immunopharmacol., (2016), pp. 1-22.
Laabi et al., "The BCMA Gene, Preferentially Expressed During B Lymphoid Maturation, is Bidirectionally Transcribed," Nucleic Acids Research, vol. 22, No. 7, (1994), pp. 1147-1154.
Li et al., "Fc Receptor-Like 5 Expression Distinguishes Two Distinct Subsets fo Human Circulating Tissue-Like Memory B Cells," J. Immunol., vol. 196, (2016), pp. 4064-4074.
Mohan et al., "Epstein-Barr Virus Nuclear Antigen 2 Induces FcRH5 Expression Through CBF1," Immunobiology, vol. 107, No. 11, (2006), pp. 4433-4439.
Rahbarizadeh et al., "Nanobody: An Old Concept and New Vehicle for Immunotargeting," Immunological Investigations, vol. 40, (2011), pp. 299-338.
Mujic-Delic et al., "GPCR-Targeting Nanobodies: Attractive Research Tools, Diagnostics, and Therapeutics," Trends in Pharmacological Sciences, vol. 35, No. 5, (2014), pp. 247-255.
Muyldermans et al., "Recognition of Antigens by Single-Domain Antibody Fragments: The Superfluous Luxury of Paired Domains," Trends in Biochemical Sciences, vol. 26, No. 4, (2001), pp. 230-235.
Muyldermans, "Single Domain Camel Antibodies: Current Status," Reviews in Molecular Biotechnology, vol. 74, (2001), pp. 277-302.
Muyldermans, "Nanobodies: Natural Single-Domain Antibodies," Annu. Rev. Biochem., vol. 82, (2013), pp. 775-797.
Novak et al., "Aberrant Expression of B-Lymphocyte Stimulator by B Chronic Lymphocytic Leukemia Cells: A Mechanism for Survival," Blood, vol. 100, No. 8, (2002), pp. 2973-2979.
Novak et al., "Expression of BCMA, TACI, and BAFF-R in Multiple Myeloma: A Mechanism for Growth and Survival," Blood, vol. 103, No. 2, (2004), pp. 689-694.
O'Connor et al., "BCMA is Essential for the Survival of Long-Lived Bone Marrow Plasma Cells," J. Exp. Med., vol. 199, No. 1, (2004), pp. 91-97.
Pegram et al., "CD28z CARs and Armored CARs," Cancer J., vol. 20, No. 2, (2014), pp. 1-14.
Riddell et al., "Adoptive Therapy with Chimeric Antigen Receptor Modified T Cells of Defined Subset Composition," Cancer J., vol. 20, No. 2, (2014), pp. 1-10.
Sadelain et al., "The Basic Principles of Chimeric Antigen Receptor (CAR) Design," Cancer Discov., vol. 3, No. 4, (2013), pp. 1-21.
Sadelain et al., "The Promise and Potential Pitfalls of Chimeric Antigen Receptors," Curr Opin Immunol., vol. 21, No. 2, (2009), pp. 1-18.
Van Audenhove et al., "Nanobodies as Versatile Tools to Understand, Diagnose, Visualize and Treat Cancer," EBioMedicine, vol. 8, (2016), pp. 40-48.
Van Bockstaele et al., "The Development of Nanobodies for Therapeutic Applications," Current Opinion in Investigational Drugs., vol. 10, No. 11, (2009), pp. 1212-1224.
Vincke et al., "Introduction to Heavy Chain Antibodies and Derived Nanobodies," Methods in Molecular Biology, vol. 911, (2012), pp. 15-26.
Wesolowski et al., "Single Domain Antibodies: Promising Experimental and Therapeutic Tools in Infection and Immunity," Med Microbiol Immunol., vol. 198, (2009), pp. 157-174.
Wilson et al., "DAP12 and KAP10 (DAP10)-Novel Transmembrane Adapter Proteins of the CD3ζ Family," Immunologic Research, vol. 22, No. 1, (2000), pp. 21-42.
Li et al., "Membrane-Proximal Epitope Facilitates Efficient T Cell Synapse Formation by Anti-FcRH5/CD3 and is a Requirement for Myeloma Cell Killing," Cancer Cell, vol. 31, No. 3, (2017), pp. 383-395.
Seckinger et al., "Target Expression, Generation, Preclinical Activity, and Pharmacokinetics of the BCMA-T Cell Bispecific Antibody EM801 for Multiple Myeloma Treatment," Cancer Cell, vol. 31, No. 3, (2017), pp. 396-410.
Abate-Daga et al., "CAR Models: Next Generation CAR Modifications for Enhanced T-Cell Function," Molecular Therapy—Oncolytics, vol. 3, (2015), p. 16014.
Atanackovic et al., "Chimeric Antigen Receptor (CAR) Teraphy for Multiple Myeloma," British Journal of Haematology, vol. 172, No. 5, (2016), pp. 685-698.
International Search Report, issued in PCT/US2018/053051, dated Apr. 12, 2018.
International Preliminary Report on Patentability, in PCT/US2018/053051, dated Mar. 31, 2020.
Office Action dated Sep. 20, 2019 for Taiwanese Appl. No. 107134265.
Office Action dated Mar. 23, 2023 EP Appl. No. 18 786 595.1.

* cited by examiner

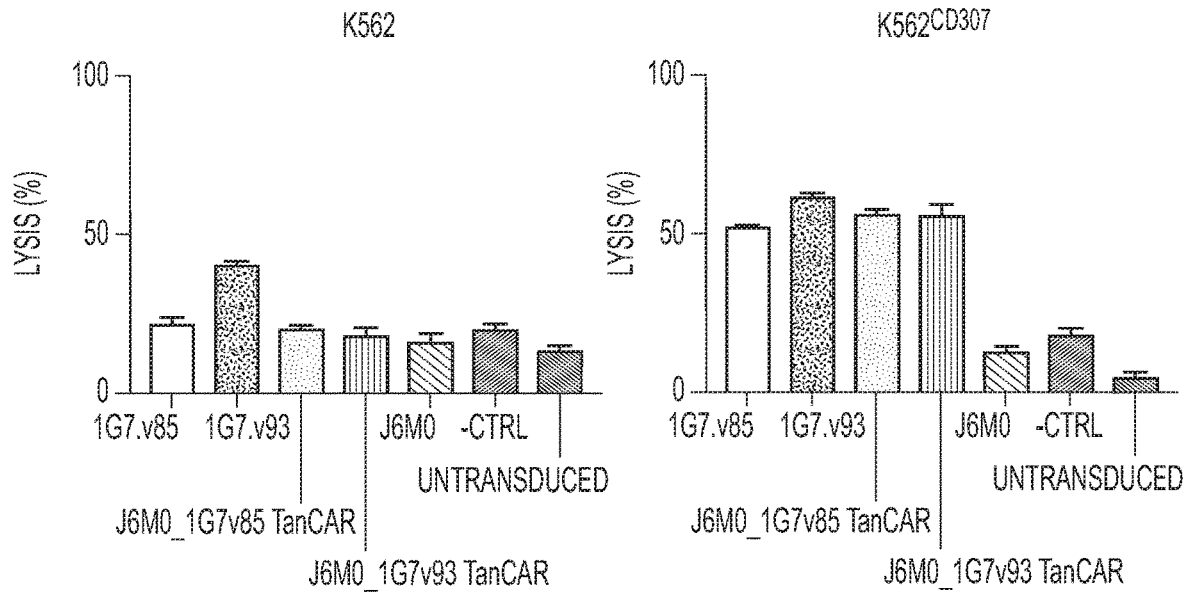
*FIG. 15A*  *FIG. 15B*
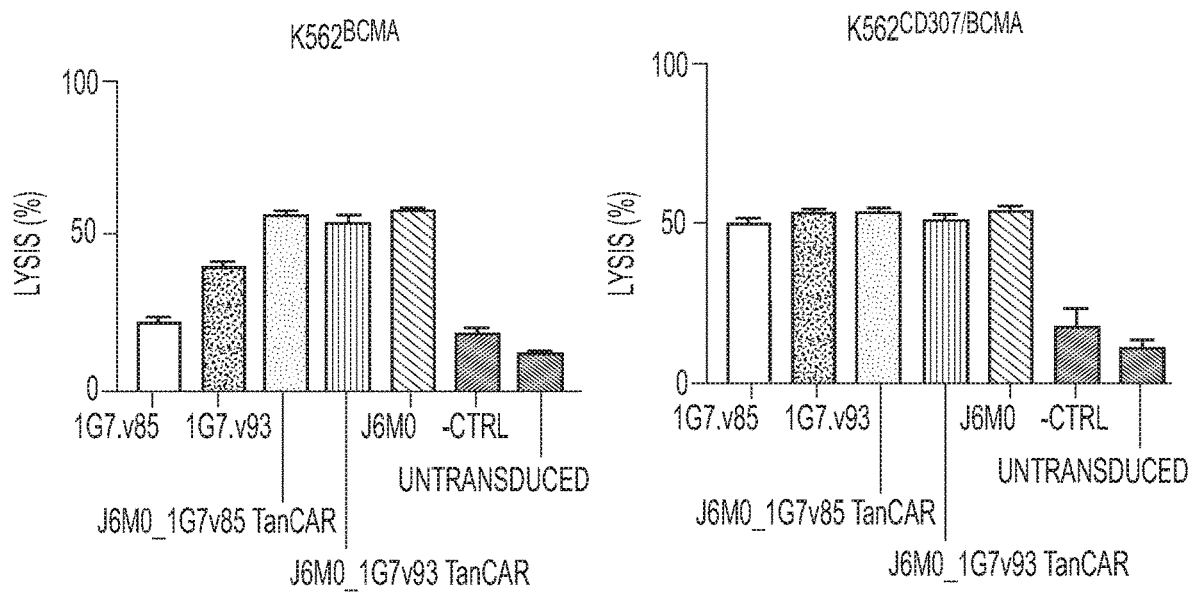
*FIG. 15C*  *FIG. 15D*

METHODS OF MAKING BISPECIFIC ANTI-CD307E AND ANTI-BCMA CHIMERIC ANTIGEN RECEPTORS AND USES OF THE SAME

CROSS-REFERENCE TO RELATED APPLICATIONS

This application claims the benefit of priority to U.S. Provisional Patent Application Ser. No. 62/566,025 filed Sep. 29, 2017, the contents of which are incorporated herein by reference in their entirety.

STATEMENT REGARDING SEQUENCE LISTING

The Sequence Listing associated with this application is provided in text format in lieu of paper copy, and is hereby incorporated by reference into the specification. The name of the text file containing the Sequence Listing is "82352-314182 2021-09-23 Sequence Listing_ST25." The text file is 88 KB, was created on Sep. 23, 2021, and is being submitted electronically via EFS-Web.

TECHNICAL FIELD

The present disclosure relates to the field of biotechnology, and more specifically to chimeric antigen receptors.

BACKGROUND

Millions of people suffer from cancer worldwide. Immunotherapy provides a targeted approach to selectively kill cancer cells by mobilizing the patient's immune system.

SUMMARY

The present invention is based on the discovery that bispecific chimeric antigen receptors that can specifically bind to both BCMA and CD307e can be used to selectively target cancer cells that express both BCMA and CD307e on their surface. This bispecific approach to treating cancer reduces the likelihood of tumors escaping therapy by losing one or the other antigens. Deeper responses due to more active chimeric antigen receptors targeting two antigens versus one antigen thus produces a durability of anti-tumor response which is longer than targeting a single antigen.

Provided herein are chimeric antigen receptors (CARs) that include: a first antigen-binding domain that binds specifically to B-cell maturation antigen (BCMA); a second antigen-binding domain that binds specifically to CD307e; a transmembrane domain; a co-stimulatory domain; and an intracellular signaling domain. Some embodiments of any of the CARs described herein further include a linker that is positioned between the first antigen-binding domain and the second antigen-binding domain. In some embodiments of any of the CARs described herein, the linker is a GS connector. Some embodiments of any of the CARs described herein further include a hinge sequence that is positioned between the second antigen-binding domain and the transmembrane domain. Some embodiments of any of the CARs described herein further include a hinge sequence that is positioned between the first antigen-binding domain and the transmembrane domain. In some embodiments of any of the CARs described herein, the hinge sequence is a CD8a hinge sequence or a CD28 hinge sequence.

In some embodiments of any of the CARs described herein, the CAR includes, going in the N-terminal to the C-terminal direction: the first antigen-binding domain, the linker, the second antigen-binding domain, the transmembrane domain, the co-stimulatory domain, and the intracellular signaling domain. Some embodiments of any of the CARs described herein further include a hinge sequence positioned between the second antigen-binding domain and the transmembrane domain.

In some embodiments of any of the CARs described herein, the CAR includes, going in the N-terminal to the C-terminal direction: the second antigen-binding domain, the linker, the first antigen-binding domain, the transmembrane domain, the co-stimulatory domain, and the intracellular signaling domain. Some embodiments of any of the CARs described herein further include a hinge sequence positioned between the first antigen-binding domain and the transmembrane domain.

In some embodiments of any of the CARs described herein, one or both of the first antigen-binding domain and the second antigen-binding domain is a single-chain variable fragment (scFv). In some embodiments of any of the CARs described herein, the first antigen-binding domain and the second antigen-binding domain are both a scFv. In some embodiments of any of the CARs described herein, the first antigen-binding domain includes, going in the N-terminal to the C-terminal direction, a $V_L$ domain and a $V_H$ domain separated by a first scFv linker. In some embodiments of any of the CARs described herein, the first antigen-binding domain includes, going in the N-terminal to the C-terminal direction, a $V_H$ domain and a $V_L$ domain separated by a first scFv linker. In some embodiments of any of the CARs described herein, the second antigen-binding domain comprises, going in the N-terminal to the C-terminal direction, a $V_L$ domain and a $V_H$ domain separated by a second scFv linker. In some embodiments of any of the CARs described herein, the second antigen-binding domain comprises, going in the N-terminal to the C-terminal direction, a $V_H$ domain and a $V_L$ domain separated by a second scFv linker. In some embodiments of any of the CARs described herein, one or both of the first scFv linker and the second scFv linker is a Whitlow linker. In some embodiments of any of the CARs described herein, both the first scFv linker and the second scFv linker are Whitlow linkers.

In some embodiments of any of the CARs described herein, the transmembrane domain is the transmembrane domain of CD28, CD3 epsilon, CD4, CD5, CD6, CD8a, CD9, CD16, CD22, CD33, CD37, CD45, CD64, CD80, CD86, CD134, 4-1BB, or CD154. In some embodiments of any of the CARs described herein, the co-stimulatory domain is the co-stimulatory domain of 4-1BB, CD28, CD2, CD4, CD8, GITR glucocorticoid-induced TNFR family related gene (GITR), nerve growth factor receptor (NGFR, CD271), or CD154. In some embodiments of any of the CARs described herein, the intracellular signaling domain is the intracellular signaling domain of CD3zeta, CD5, CD22, CD79, hematopoietic cell signal transducer (DAP-10, KAP10), or TYRO protein tyrosine kinase binding protein (DAP-12, KARAP) (see, e.g., Wilson et al. (2000) Immunol Res. 22(1):21-42). In some embodiments of any of the CARs described herein, the intracellular signaling domain is the intracellular signaling domain of CD3zeta and the co-stimulatory domain is the co-stimulatory domain of 4-1BB.

Also provided herein are nucleic acids that encode any of the CARs described herein. Also provided herein are vectors that include any of the nucleic acids encoding any of the CARs described herein. In some embodiments of any of the vectors described herein, the nucleic acid encoding any of the CARs described herein is operably linked to one or both of a promoter and an enhancer. In some embodiments of any of the vectors described herein, the promoter is an inducible promoter.

Also provided herein are cells that include any of the nucleic acids encoding any of the CARs described herein described herein or any of the vectors described herein. In some embodiments of any of the cells described herein, the cell is a eukaryotic cell. In some embodiments of any of the cells described herein, the eukaryotic cell is a mammalian cell. In some embodiments of any of the cells described herein, the mammalian cell is a human cell. In some embodiments of any of the cells described herein, the mammalian cell is a cell selected from the group of: a T cell, a natural killer (NK) cell, a monocyte/macrophage, and a B cell. In some embodiments of any of the cells described herein, the mammalian cell is a mammalian cell obtained from a subject. In some embodiments of any of the cells described herein, the subject is diagnosed or identified as having a cancer. In some embodiments of any of the cells described herein, the cancer is characterized by cancer cells that express one or both of BCMA and CD307e.

Also provided herein are pharmaceutical compositions that include any of the cells described herein and a pharmaceutically acceptable carrier. Also provided herein are kits that include any of the pharmaceutical compositions described herein.

Also provided herein are pharmaceutical compositions including any of the nucleic acids encoding any of the CARs described herein and a pharmaceutically acceptable carrier. Also provided herein are kits that include any of the pharmaceutical compositions described herein.

Also provided herein are methods of generating a chimeric antigen receptor (CAR)-expressing cell that include introducing into a cell any of the nucleic acids encoding any of the CARs described herein, or any of the vectors described herein. In some embodiments of any of the methods described herein, the cell is a eukaryotic cell. In some embodiments of any of the methods described herein, the eukaryotic cell is a mammalian cell. In some embodiments of any of the methods described herein, the mammalian cell is a human cell. In some embodiments of any of the methods described herein, the mammalian cell is a cell selected from the group consisting of: a T cell, a NK cell, a macrophage/monocyte, and a B cell. In some embodiments of any of the methods described herein, the mammalian cell is a mammalian cell obtained from a subject. In some embodiments of any of the methods described herein, the subject is diagnosed or identified as having a cancer. In some embodiments of any of the methods described herein, the cancer is characterized by cancer cells that express one or both of BCMA and CD307e. Some embodiments of any of the methods described herein further include, after the introducing step: culturing the cell in a liquid culture medium. Some embodiments of any of the methods described herein can further include, before the introducing step: obtaining the cell from the subject.

Also provided herein are methods of treating a cancer in a subject that include: administering a therapeutically effective amount of any of the cells described herein to the subject. In some embodiments of any of the methods described herein, the cancer is characterized by cancer cells that express one or both of BCMA and CD307e. In some embodiments of any of the methods described herein, the cancer is a carcinoma, a sarcoma, a myeloma, a leukemia, or a lymphoma. In some embodiments of any of the methods described herein, the subject has been diagnosed or identified as having the cancer. Some embodiments of any of the methods described herein further include, prior the administering step: obtaining an initial cell from the subject; and introducing any of the nucleic acids encoding any of the CARs described herein, or any of the vectors described herein into the initial cell, to yield the cell that is administered to the subject. Some embodiments of any of the methods described herein further include, between the introducing step and the administering step, a step of culturing the cell that is administered to the subject in a liquid culture medium. In some embodiments of any of the methods described herein, the subject is a human. Also provided herein are methods of treating multiple myeloma in a subject that include administering to a subject a therapeutically effective amount of any of the cells described herein. In some embodiments of any of the methods described herein, the subject has been diagnosed or identified as having multiple myeloma. Some embodiments of any of the methods described herein further include, prior the administering step: obtaining an initial cell from the subject; and introducing any of the nucleic acids encoding any of the CARs described herein, or any of the vectors described herein into the initial cell, to yield the cell that is administered to the subject. Some embodiments of any of the methods described herein further include, between the introducing step and the administering step, a step of culturing the cell that is administered to the subject in a liquid culture medium. In some embodiments of any of the methods described herein, the subject is human.

Some embodiments of any of the methods described herein further include administering to the subject one or more additional anti-cancer therapies. In some embodiments of any of the methods described herein, the one or more additional anti-cancer therapies is selected from the group consisting of chemotherapy, immunotherapy, surgical resection, and radiation therapy.

The use of the term "a" before a noun is meant "one or more" of the particular noun. For example, the phrase "a mammalian cell" means "one or more mammalian cell."

The terms "chimeric antigen receptor" and "CAR" are used interchangeably herein, and refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. Exemplary CARs, exemplary domains within CARs, and derivatives thereof (e.g., CAR variants) are described, e.g., in PCT Application No. US2014/016527; Fedorov et al. Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety.

The term "transmembrane domain" means a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The term "costimulatory domain" means a signaling domain from an endogenous co-stimulatory transmembrane polypeptide expressed in a T lymphocyte that promotes the downstream T-cell receptor signaling and/or T cell activation. Non-limiting examples of costimulatory domains are described herein. Additional examples of costimulatory domains are known in the art. See, e.g., Chen et al., Nature Reviews Immunol. 13:227-242, 2013.

A "intracellular signaling domain" is an intracellular domain in a transmembrane protein that is required for the activation and/or proliferation of a cell (e.g., any of the mammalian cells described herein, e.g., any of the T-cells, any of the B-cells, monocytes, macrophages, eosinophils, NK cells, and neutrophils described herein). Non-limiting examples of intracellular signaling domains are described herein. Additional examples of intracellular signaling domains are known in the art.

The term "antigen-binding domain" means a domain that binds specifically to a target antigen. In some examples, an antigen-binding domain can be formed from the amino acids present within a single-chain polypeptide. In other examples, an antigen-binding domain can be formed from amino acids present within a first single-chain polypeptide and the amino acids present in one or more additional single-chain polypeptides (e.g., a second single-chain polypeptide). Non-limiting examples of antigen-binding domains are described herein. Additional examples of antigen-binding domains are known in the art.

The phrase "treatment of cancer" or "treating cancer" means a reduction in the number, frequency, or severity of one or more (e.g., two, three, four, or five) symptoms of a cancer in a subject having a cancer. Non-limiting symptoms of cancer are described herein. Additional symptoms of cancer are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 15A is a representative graph of antigen negative K562 tumor cell lysis following incubation with 1G7.v85, 1G7.v93, J6M0_1G7v85 TanCAR, J6M0_1G7v93 TanCAR, J6M0, negative control, or untransduced (UNTR) control T cells.

FIG. 15B is a representative graph of CD307$^+$ K562 tumor cell lysis following incubation with 1G7.v85, 1G7.v93, J6M0_1G7v85 TanCAR, J6M0_1G7v93 TanCAR, J6M0, negative control, or untransduced (UNTR) control T cells.

FIG. 15C is a representative graph of BCMA$^+$ K562 tumor cell lysis following incubation with 1G7.v85, 1G7.v93, J6M0_1G7v85 TanCAR, J6M0_1G7v93 TanCAR, J6M0, negative control, or untransduced (UNTR) control T cells.

FIG. 15D is a representative graph of CD307$^+$ BCMA$^+$ K562 tumor cell lysis following incubation with 1G7.v85, 1G7.v93, J6M0_1G7v85 TanCAR, J6M0_1G7v93 TanCAR, J6M0, negative control, or untransduced (UNTR) control T cells.

DETAILED DESCRIPTION

Figure 1:
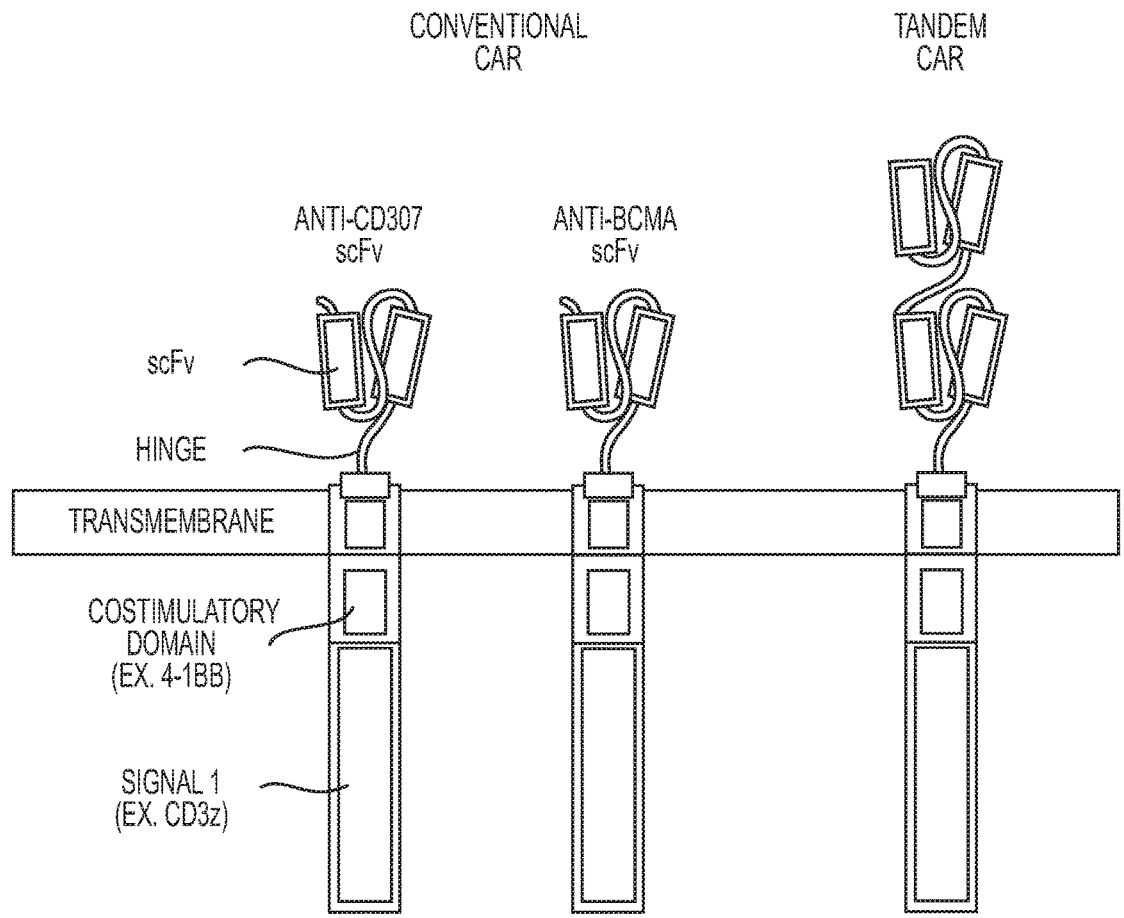
FIG. 1 is a schematic representation of a conventional chimeric antigen receptor (CAR) and a tandem CAR.

Accordingly, the present disclosure provides chimeric antigen receptors (CAR) that include a first antigen-binding domain that binds specifically to B-cell maturation antigen (BCMA); a second antigen-binding domain that binds specifically to CD307e; a transmembrane domain; a co-stimulatory domain; and an intracellular signaling domain. Also provided are nucleic acids the encode any of these CARs, vectors that include a nucleic acid encoding any of these CARs, and cells that express any of these CARs. Also provided are compositions that include any of the cells that express any of the CARs. Also provided are compositions that include any of the nucleic acids that encode any of the CARs described herein, or any of the vectors that include any of the nucleic acids encoding any of the CARs described herein. Also provided are kits that include any of the compositions described herein. Also provided here are methods of making a cell expressing any of the CARs described herein, and methods of treating a subject having a cancer that include administering any of the cells expressing any of the CARs described herein.

Various exemplary aspects of these CARs and methods are described below and can be used in any combination in the compositions and methods provided herein without limitation. Exemplary aspects of the provided methods are described below; however, one skilled in the art will appreciate that additional steps can be added to the methods described herein and other materials can be used to perform any of the steps of the methods described herein.

Chimeric Antigen Receptor (CAR)

A chimeric antigen receptor (CAR) is an artificially constructed hybrid protein or that includes at least one antigen-binding domain (e.g., a single chain variable fragment (scFv)), a transmembrane domain, and at least one cellular signaling domain (e.g., at least one co-stimulatory domain and at least one intracellular signaling domain). CARs have the ability to redirect T-cell specificity and reactivity toward a selected target in a non-MHC-restricted manner (e.g., a BCMA antigen or a CD307e antigen). CARs have been described in, e.g., Kershaw et al., Nature Reviews Immunol. 5(12):928-940, 2005; Eshhar et al., Proc. Natl. Acad. Sci. U.S.A. 90(2):720-724, 1993; Sadelain et al., Curr. Opin. Immunol. 21(2): 215-223, 2009; WO 2015/142675; WO 2015/150526; and WO 2014/134165, the disclosures of each of which are incorporated herein by reference in their entirety.

Provided herein are chimeric antigen receptors (CARs) that include a first antigen-binding domain that binds specifically to B-cell maturation antigen (BCMA); a second antigen-binding domain that binds specifically to CD307e; a transmembrane domain; a co-stimulatory domain; and an intracellular signaling domain. Non-limiting aspects and examples of first antigen-binding domains, second antigen-binding domains, transmembrane domains, co-stimulatory domains, and intracellular signaling domains are described herein. Additional aspects and examples of first antigen-binding domains, second antigen-binding domains, transmembrane domains, co-stimulatory domains, and intracellular signaling domains are known in the art.

In some examples of any of the CARs described herein, going in the N-terminal to the C-terminal direction, the intracellular portion of the CAR includes a co-stimulatory domain and an intracellular signaling domain. In some examples of any of the CARs described herein, going in the N-terminal to the C-terminal direction, the intracellular portion of the CAR includes an intracellular signaling domain and a co-stimulatory domain.

In some examples of any of the CARs described herein, going in the C-terminal to the N-terminal direction, the intracellular portion of the CAR includes a co-stimulatory domain and an intracellular signaling domain. In some examples of any of the CARs described herein, going in the C-terminal to the N-terminal direction, the intracellular portion of the CAR includes an intracellular signaling domain and a co-stimulatory domain.

Some embodiments of any of the CARs described herein further include a linker that is positioned between the first antigen-binding domain and the second antigen-binding domain. Non-limiting examples of linkers are described herein. In some embodiments, the linker is a GS connector.

Some embodiments of any of the CARs described herein further include a hinge sequence that is positioned between the second antigen-binding domain and the transmembrane domain. Some embodiments of any of the CARs described herein further include a hinge sequence that is positioned between the first antigen-binding domain and the transmembrane domain. In some embodiments, the hinge sequence is or includes a CD8a hinge sequence. In some embodiments, the hinge sequence is or includes CD28 hinge sequence.

In some embodiments of any of the CARs described herein, the CAR includes, going in the N-terminal to the C-terminal direction: the first antigen-binding domain, the linker, the second antigen-binding domain, the transmembrane domain, the co-stimulatory domain, and the intracellular signaling domain. In some embodiments of any of the CARs described herein, the CAR includes, going in the C-terminal to the N-terminal direction: the first antigen-binding domain, the linker, the second antigen-binding domain, the transmembrane domain, the co-stimulatory domain, and the intracellular signaling domain. Some embodiments of any of the CARs described herein include a hinge sequence positioned between the second antigen-binding domain and the transmembrane domain.

In some embodiments of any of the CARs described herein, the CAR includes, going in the N-terminal to the C-terminal direction: the second antigen-binding domain, the linker, the first antigen-binding domain, the transmembrane domain, the co-stimulatory domain, and the intracellular signaling domain. In some embodiments of any of the CARs described herein, the CAR includes, going in the C-terminal to the N-terminal direction: the second antigen-binding domain, the linker, the first antigen-binding domain, the transmembrane domain, the co-stimulatory domain, and the intracellular signaling domain. Some embodiments of any of the CARs described herein further include a hinge sequence positioned between the first antigen-binding domain and the transmembrane domain.

In some examples of any of the CARs described herein, one or both of the first antigen-binding domain and the second antigen-binding domain is a single-domain variable fragment (scFv). In some examples of any of the CARs described herein, both the first antigen-binding domain and the second antigen-binding domain are both a single-domain variable fragment (scFv).

In some embodiments of any of the CARs described herein, the first antigen-binding domain includes, going in the N-terminal to the C-terminal direction, a VL domain and a VH domain separated by a first scFv linker. In some embodiments of any of the CARs described herein, the first antigen-binding domain includes, going in the N-terminal to the C-terminal direction, a VH domain and a VL domain separated by a first scFv linker.

In some embodiments of any of the CARs described herein, the second antigen-binding domain includes, going in the N-terminal to the C-terminal direction, a VL domain and a VH domain separated by a second scFv linker. In some embodiments of any of the CARs described herein, the second antigen-binding domain includes, going in the N-terminal to the C-terminal direction, a VH domain and a VL domain separated by a second scFv linker.

Non-limiting aspects and examples of first and second scFv linkers are described herein. In some embodiments of any of the CARs described herein, one or both of the first scFv linker and the second scFv linker is a Whitlow linker. In some embodiments of any of the CARs described herein, both of the first scFv linker and the second scFv linker are Whitlow linkers.

In some embodiments of any of the CARs described herein, the transmembrane is or includes a transmembrane domain of CD28, CD3 epsilon, CD4, CD5, CD6, CD8a, CD9, CD16, CD22, CD33, CD37, CD45, CD64, CD80, CD86, CD134, 4-1BB, or CD154. Additional examples and aspects of transmembrane domains are described herein.

In some embodiments of any of the CARs described herein, the co-stimulatory domain is or includes the co-stimulatory domain of 4-1BB, CD28, CD2, CD4 or CD8. Additional examples and aspects of co-stimulatory domains are described herein.

In some embodiments of any of the CARs described herein, the intracellular signaling domain is or includes the intracellular signaling domain of CD3 zeta, CD5, CD22, DAP-10, DAP-12, CD5, CD22, or CD79. Additional examples and aspects of intracellular signaling domains are described herein.

In some embodiments of any of the CARs described herein, the intracellular signaling domain is CD3 zeta and the costimulatory domain is the co-stimulatory domain of 4-1BB or CD28.

A variety of methods that can be used to determine the $K_D$ values of any of the CARs described herein are known in the art (e.g., an electrophoretic mobility shift assay, a filter binding assay, surface plasmon resonance, and a biomolecular binding kinetics assay, etc.).

Antigen-Binding Domains

In some embodiments, the first antigen-binding domain and the second antigen-binding domain are each independently selected from the group consisting of: a VHH domain, a VNAR domain, and a scFv. Additional examples of antigen-binding domains that can be used are known in the art.

A $V_HH$ domain is a single monomeric variable antibody domain that can be found in camelids. A $V_{NAR}$ domain is a single monomeric variable antibody domain that can be found in cartilaginous fish. Non-limiting aspects of $V_HH$ domains and $V_{NAR}$ domains are described in, e.g., Cromie et al., *Curr Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments of any of the CARs described herein, the first antigen-binding domain and the second antigen-binding domain are both VHH domains, or at least one antigen-binding domain is a VHH domain. In some embodiments of any of the CARs described herein, the first antigen-binding domain and the second antigen-binding domain are both VNAR domains, or at least one antigen-binding domain is a VNAR domain. In some embodiments of any of the CARs described herein, the first antigen-binding domain and the second antigen-binding domain are both scFv domains, or at least one antigen-binding domain is a scFv domain.

In some examples, the first antigen-binding domain and/or the second antigen-binding domain is human. In some examples, the first antigen-binding domain and/or the second antigen-binding domain is humanized.

In some examples, the first antigen-binding domain is a scFv, e.g., a scFv derived from J6M0.

The light chain variable domain and the heavy chain variable domain of J6M0 are provided below. The three CDRs present in the light chain variable domain and the three CDRs present in the heavy chain variable domain are shown in bold.

Light Chain Variable Domain of J6M0 (SEQ ID NO: 1) (Each CDR is Shown in Bold.)

```
Light Chain Variable Domain of J6M0
(Each CDR is shown in bold.)
                                      (SEQ ID NO: 1)
DIQMTQSPSSLSASVGDRVTITCSASQDISNYLNWYQQKPGKAPKLLIYY

TSNLHSGVPSRFSGSGSGTDFTLTISSLQPEDFATYYCQQYRKLPWTFGQ

GTKLEIKR

Heavy Chain Variable Domain of J6M0
(Each CDR is shown in bold.)
                                      (SEQ ID NO: 2)
QVQLVQSGAEVKKPGSSVKVSCKASGGTFSNYWMHWVRQAPGQGLEWMGA

TYRGHSDTYYNQKFKGRVTITADKSTSTAYMELSSLRSEDTAVYYCARGA

IYDGYDVLDNWGQGTLVTVSS
```

The nucleic acid sequence encoding the light chain variable domain of J6M0 and the nucleic acid sequence encoding the heavy chain variable domain of J6M0. cDNA Encoding Light Chain Variable Domain of J6M0 (SEQ ID NO: 3) gatatacaaatgacccaaagcccaagctctct-gagtgcgtccgtcggggacagagtgacaataacatgtagtgcgtct cagga-catcagtaactacctgaactggtaccagcaaaaaccaggtaaggctcc-caagctgcttatttattatacctcaa atctgcacagcggcgttccatcacgcttttc-tggctctggcagtgggacggacttcaccctcacaatttctagccttcaa ccagaa-gatttcgccacttactactgtcaacagtaccggaagctgccctggacgt-tcgggcagggaacaaaacttga

```
cDNA Encoding Light Chain Variable Domain of J6M0
                                      (SEQ ID NO: 3)
gatatacaaatgacccaaagcccaagctctctgagtgcgtccgtcgggga cagagtgacaataacatgtagtgcgtctcaggacatcagtaactacctga actggtaccagcaaaaaccaggtaaggctcccaagctgcttatttattat acctcaaatctgcacagcggcgttccatcacgcttttctggctctggcag tgggacggacttcaccctcacaatttctagccttcaaccagaagatttcg ccacttactactgtcaacagtaccggaagctgccctggacgttcgggcag ggaacaaaacttgaaatcaagcgg cDNA Encoding Heavy Chain Variable Domain of J6M0
                                      (SEQ ID NO: 4)
caagtccagctggttcaatccggagctgaggtgaaaaaaccaggctcaag cgttaaggtttcttgcaaggccagtggggggactttctccaactactgga tgcactgggtacggcaggcccccggtcaagggcttgaatggatgggtgcc acgtacagaggacactcagacacatactataaccaaaaattcaaggggcg agttactattactgcagacaagtcaacttctacagcctacatggaattgt cctcccttaggtctgaagacacagcagtgtactattgcgcgcggggggcc atatacgacggatacgacgtgcttgataactggggccagggcaccctcgt gactgttagctcc
```

In some embodiments of the CARs described herein, the first antigen-binding domain includes a VL domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the VL domain of J6M0, and/or includes a VH domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the VH domain of J6M0. In some embodiments of the CARs described herein, the first antigen-binding domain includes a VL domain that is or includes the VL domain of J6M0, and/or a VH domain that is or includes the VH domain of J6M0. In some embodiments of any of the CARs described herein, the first antigen-binding domain includes a VL domain that is or includes the sequence of VL of J6M0, except that it includes one, two, three, four, five, six, seven, eight, nine, ten, eleven, twelve, thirteen, fourteen, or fifteen amino acid substitutions, and/or includes a VH domain that is or includes the sequence of VH of J6M0, except that it includes one, two, three, four, five, six, seven, eight, nine, ten, eleven, twelve, thirteen, fourteen, or fifteen amino acid substitutions. In some embodiments the first antigen-binding domain includes the three CDRs in the light chain variable domain of J6M0, and/or the three CDRs in the heavy chain variable domain of J6M0.

In some examples of any of the CARs described herein, the CAR can bind to a BCMA antigen (e.g., an epitope present in the extracellular domain of BCMA) with a dissociation equilibrium constant ($K_D$) of less than $1\times10^{-5}$ M, less than $0.5\times10^{-5}$ M, less than $1\times10^6$ M, less than $0.5\times10$ M, less than $1\times10^{-7}$ M, less than $0.5\times10^{-7}$ M, less than $1\times10^{-8}$ M, less than $0.5\times10^{-8}$ M, less than $1\times10^{-9}$ M, less than $0.5\times10^{-9}$, less than $1\times10^{-10}$ M, less than $0.5\times10^{-10}$ M, or less than $1\times10^{-11}$ M (e.g., as measured using surface plasmon resonance).

In some examples of any of the CARs described herein, the CAR can bind to a BCMA antigen (e.g., an epitope present in the extracellular domain of BCMA) with a $K_D$ of about $1\times10^{-11}$ M to about $1\times10^{-5}$ M, about $1\times10^{-11}$ M to about $0.5\times10^{-5}$ M, about $1\times10^{-11}$ M to about $1\times10^6$ M, about $1\times10^{-11}$ M to about $0.5\times10^6$ M, about $1\times10^{-11}$ M to about $1\times10^{-7}$ M, about $1\times10^{-11}$ M to about $0.5\times10^{-7}$ M, about $1\times10^{-11}$ M to about $1\times10^{-8}$ M, about $1\times10^{-11}$ M to about $0.5\times10^{-8}$ M, about $1\times10^{-11}$ M to about $1\times10^{-9}$ M, about $1\times10^{-11}$ M to about $0.5\times10^{-9}$ M, about $1\times10^{-11}$ M to about $1\times10^{-10}$ M, about $1\times10^{-11}$ M to about $0.5\times10^{-10}$ M; about $0.5\times10^{-10}$ M to about $1\times10^{-5}$ M, about $0.5\times10^{-10}$ M to about $0.5\times10^{-5}$ M, about $0.5\times10^{-10}$ M to about $1\times10^{-6}$ M, about $0.5\times10^{-10}$ M to about $0.5\times10^6$ M, about $0.5\times10^{-10}$ M to about $1\times10^{-7}$ M, about $0.5\times10^{-10}$ M to about $0.5\times10^{-7}$ M, about $0.5\times10^{-10}$ M to about $1\times10^{-8}$ M, about $0.5\times10^{-10}$ M to about $0.5\times10^{-8}$ M, about $0.5\times10^{-10}$ M to about $1\times10^{-9}$ M, about $0.5\times10^{-10}$ M to about $0.5\times10^{-9}$ M, about $0.5\times10^{-10}$ M to about $1\times10^{-10}$ M, about $1\times10^{-10}$ M to about $1\times10^{-5}$ M, about $1\times10^{-10}$ M to about $0.5\times10^{-5}$ M, about $1\times10^{-10}$ M to about $1\times10^6$ M, about $1\times10^{-10}$ M to about $0.5\times10^6$ M, about $1\times10^{-10}$ M to about $1\times10^{-7}$ M, about $1\times10^{-10}$ M to about $0.5\times10^{-7}$ M, about $1\times10^{-10}$ M to about $1\times10^{-8}$ M, about $1\times10^{-10}$ M to about $0.5\times10^{-8}$ M, about $1\times10^{-10}$ M to about $1\times10^{-9}$ M, about $1\times10^{-10}$ M to about $0.5\times10^{-9}$ M, about $0.5\times10^{-9}$ M to about $1\times10^{-5}$ M, about $0.5\times10^{-9}$ M to about $0.5\times10^{-5}$ M, about $0.5\times10^{-9}$ M to about $1\times10^{-6}$ M, about $0.5\times10^{-9}$ M to about $0.5\times10^{-6}$ M, about $0.5\times10^{-9}$ M to about $1\times10^{-7}$ M, about $0.5\times10^{-9}$ M to about $0.5\times10^{-7}$ M, about $0.5\times10^{-9}$ M to about $1\times10^{-8}$ M, about $0.5\times10^{-9}$ M to about $0.5\times10^{-8}$ M, about $0.5\times10^{-9}$ M to about $1\times10^{-9}$ M, about $1\times10^{-9}$ M to about $1\times10^{-5}$ M, about $1\times10^{-9}$ M to about $0.5 \times 10^{-5}$ M, about $1 \times 10^{-9}$ M to about $1 \times 10^{-6}$ M, about $1 \times 10^{-9}$ M to about $0.5 \times 10^{-6}$ M, about $1 \times 10^{-9}$ M to about $1 \times 10^{-7}$ M, about $1 \times 10^{-9}$ M to about $0.5 \times 10^{-7}$M, about $1 \times 10^{-9}$ M to about $1 \times 10^{-8}$ M, about $1 \times 10^{-9}$ M to about $0.5 \times 10^{-8}$ M, about $0.5 \times 10^{-8}$ M to about $1 \times 10^{-5}$ M, about $0.5 \times 10^{-8}$ M to about $0.5 \times 10^{-5}$ M, about $0.5 \times 10^{-8}$ M to about $1 \times 10^{-6}$ M, about $0.5 \times 10^{-8}$ M to about $0.5 \times 10^{-6}$ M, about $0.5 \times 10^{-8}$ M to about $1 \times 10^{-7}$ M, about $0.5 \times 10^{-8}$ M to about $0.5 \times 10^{-7}$ M, about $0.5 \times 10^{-7}$ M to about $0.5 \times 10^{-8}$ M to about $1 \times 10^{-8}$ M, $1 \times 10^{-8}$ M to about $1 \times 10^{-5}$ M, about $1 \times 10^{-8}$ M to about $0.5 \times 10^{-5}$ M, about $1 \times 10^{-8}$ M to about $1 \times 10^{-6}$ M, about $1 \times 10^{-8}$ M to about $0.5 \times 10^{-6}$ M, about $1 \times 10^{-8}$ M to about $1 \times 10^{-7}$ M, about $1 \times 10^{-8}$M to about $0.5 \times 10^{-7}$ M, about $0.5 \times 10^{-7}$ M to about $1 \times 10^{-5}$ M, about $0.5 \times 10^{-7}$ M to about $0.5 \times 10^{-5}$ M, about $0.5 \times 10^{-7}$ M to about $1 \times 10^{-6}$ M, about $0.5 \times 10^{-7}$ M to about $0.5 \times 10^{-6}$ M, about $0.5 \times 10^{-7}$ M to about $1 \times 10^{-7}$ M, about $1 \times 10^{-7}$ M to about $1 \times 10^{-5}$ M, about $1 \times 10^{-7}$ M to about $0.5 \times 10^{-5}$ M, about $1 \times 10^{-7}$ M to about $1 \times 10^{-6}$ M, about $1 \times 10^{-7}$ M to about $0.5 \times 10^{-6}$ M, about $0.5 \times 10^{-6}$ M to about $1 \times 10^{-5}$ M, about $0.5 \times 10^{-6}$ M to about $0.5 \times 10^{-5}$ M, about $0.5 \times 10^{-6}$ M to about $1 \times 10^{-6}$ M, about $1 \times 10^{-6}$ M to about $1 \times 10^{-5}$ M, about $1 \times 10$ M to about $0.5 \times 10^{-5}$M, or about $0.5 \times 10^{-5}$ M to about $1 \times 10^{-5}$ M (e.g., as measured using surface plasmon resonance).

In some examples, the second antigen-binding domain is a scFv, e.g., a scFv derived from 10A8.

The light chain variable domain and the heavy chain variable domain of 10A8 are provided below. The three CDRs present in the light chain variable domain and the three CDRs present in the heavy chain variable domain are shown in bold.

```
Human Light Chain Variable Domain of 10A8
(Each CDR isshown in bold.)
                                   (SEQ ID NO: 5)
DIQMTQSPSSLSASVGDRVTITCKASQDVSTAVAWYQQKPGKAPKLLIYS

ASYRYTGVPSRFSGSGSGTDFTLTISSLQPEDFATYYCQQHFSSPRTFGQ

GTKVEIKR

Human Heavy Chain Variable Domain of 10A8
(Each CDR isshown in bold.)
                                   (SEQ ID NO: 6)
EVQLVESGGGLVQPGGSLRLSCAASGFTFSSYAVSWVRQAPGKGLEWVAT

ISSGGSLTFYLDSVRGRFTISRDNSKNTLYLQMNSLRAEDTAVYYCARPI

PDYYALDYVVGQGTLVTVSS cDNA Encoding Human Light Chain Variable Domain of
10A8
                                   (SEQ ID NO: 7)
gatatccagatgacccagtctcctagttccttgtccgcatcagtaggaga cagggtcaccatcacctgcaaggccagtcaggatgtgagtactgctgtag cctggtatcaacagaaaccaggaaaagctcctaaactactgatttattcg gcatcctaccggtacactggagtcccttctcgcttctctggcagtggatc tgggacggatttcactctcaccatcagcagtctgcagcctgaagactttg caacttattactgtcagcaacattttagtagtcctcggacgttcggtcaa ggtaccaaggtggagatcaaacga cDNA Encoding Human Heavy Chain Variable Domain of
10A8
                                   (SEQ IDNO: 8)
gaagtgcagttggtggagtctgggggaggcttagtgcagcctggagggtc cctgcgactctcctgtgcagcctctggattcactttcagtagctatgccg
```

```
tgtcttgggttcgccaggctccggggaagggactggagtgggtcgctacc attagcagtggtggtagtttgaccttctatttagacagtgtgagggtcg attcaccatctccagagacaatagcaagaacaccctgtacctgcaaatga atagtctgagggctgaagacacggccgtgtattactgtgcaaggcccatt ccggattactatgctttggactactggggtcaaggaaccttagtcaccgt ctcctca Mouse Light Chain Variable Domain of 10A8
(Each CDR isshown in bold.)
                                   (SEQ ID NO: 9)
DIVMTQSHKFMSTSVRDRVSITCKASQDVSTAVAWYQQKPGQSPKLLIYS

ASYRYTGVPDRFTGSGSGTDFTFTISSVQAEDLAVYYCQQHFSSPRTFGG

GTKVEIKR

Mouse Heavy Chain Variable Domain of 10A8
(Each CDRis shown in bold.)
                                   (SEQ ID NO: 10)
EVQLVESGGGLVKPGGSLKISCAASGFTFSSYAVSWVRQTPEKRLEWVAT

ISSGGSLTFYLDSVRGRFTISRDNAKNTLYLQMSSLRSEDTAMYYCARPI

PDYYALDYWGQGTSVTVSS cDNA Encoding Mouse Light Chain Variable Domain of
10A8
                                   (SEQ ID NO: 11)
gatatcgtgatgacccagtctcataaattcatgtccacatcagtaagaga cagggtcagcatcacctgcaaggccagtcaggatgtgagtactgctgtag cctggtatcaacagaaaccaggacaatctcctaaactactgatttattcg gcatcctaccggtacactggagtccctgatcgcttcactggcagtggatc tgggacggatttcactttcaccatcagcagtgtgcaggctgaagacctgg cagtttattactgtcagcaacattttagtagtcctcggacgttcggtgga ggtaccaaggtggagatcaaacga cDNA Encoding Mouse Heavy Chain Variable Domain of
10A8
                                   (SEQ ID NO: 12)
gaagtgcagttggtggagtctgggggaggcttagtgaagcctggagggtc cctgaaaatctcctgtgcagcctctggattcactttcagtagctatgccg tgtcttgggttcgccagactccggagaagaggctggagtgggtcgctacc attagcagtggtggtagtttgaccttctatttagacagtgtgagggtcg attcaccatctccagagacaatgccaagaacaccctgtacctgcaaatga gcagtctgaggtctgaagacacggccatgtattactgtgcaaggcccatt ccggattactatgctttggactactggggtcaaggaacctcagtcaccgt ctcctca
```

The light chain variable domain and the heavy chain variable domain of human 1G7.v85 are provided below. The three CDRs present in the light chain variable domain and the three CDRs present in the heavy chain variable domain are shown in bold.

Human Light Chain Variable Domain of 1G7.v85
(Each CDR is shown in bold.)
(SEQ ID NO: 13)
DIQMTQSPSSLSASVGDRVTITCKASQDVRNLVVWFQQKPGKAPKLLIYS

GSYRYSGVPSRFSGSGSGTDFTLTISSLQPEDFATYYCQQHYSPPYTFGQ

GTKVEIK

Human Heavy Chain Variable Domain of 1G7.v85
(Each CDR is shown in bold.)
(SEQ ID NO: 14)
EVQLVESGPGLVKPSETLSLTCTVSGFSLTRFGVHWVRQPPGKGLEWLGV

IWRGGSTDYNAAFVSRLTISKDNSKNQVSLKLSSVTAADTAVYYCSNHYY

GSSDYALDNWGQGTLVTVSS cDNA Encoding Human Light Chain Variable Domain of
1G7.v85
(SEQ ID NO: 15)
gatattcagatgacccagagcccgagcagcctgagcgcgagcgtgggcga tcgcgtgaccattacctgcaaagcgagccaggatgtgcgcaacctggtgg tgtggtttcagcagaaacccgggcaaagcgccgaaactgctgatttatagc ggcagctatcgctatagcggcgtgccgagccgctttagcggcagcggcag cggcaccgattttaccctgaccattagcagcctgcagccggaagattttg cgacctattattgccagcagcattatagcccgccgtatacctttggccag ggcaccaaagtggaaattaaa cDNA Encoding Human Heavy Chain Variable Domain of
1G7.v85
(SEQ ID NO: 16)
gaagtgcagctggtggaaagcggcccaggcctggtgaaaccgagcgaaac cctgagcctgacctgcaccgtgagcggctttagcctgacccgctttggcg tgcattgggtgcgccagccgccgggcaaaggcctggaatggctgggcgtg atttggcgcggcggcagcaccgattataacgcggcgtttgtgagccgcct gaccattagcaaagataacagcaaaaaccaggtgagcctgaaactgagca gcgtgaccgcggcggataccgcggtgtattattgcagcaaccattattat ggcagcagcgattatgcgctggataactggggccagggcaccctggtgac cgtgagcagc The light chain variable domain and the heavy chain variable domain of human 1G7.v93 are provided below. The three CDRs present in the light chain variable domain and the three CDRs present in the heavy chain variable domain are shown in bold.

Human Light Chain Variable Domain of 1G7.v93 (SEQ ID NO: 17) (Each CDR is shown in bold.)

Human Light Chain Variable Domain of 1G7.v93
(Each CDR is shown in bold.)
(SEQ ID NO: 17)
DIQMTQSPSSLSASVGDRVTITCKASQDVSNLVVWFQQKPGKAPKLLIYS

GSYRYSGVPSRFSGSGSGTDFTLTISSLQPEDFATYYCQQHYSPPYTFGQ

GTKVEIK

Human Heavy Chain Variable Domain of 1G7.v93
(Each CDR is shown in bold.)
(SEQ ID NO: 18)
EVQLVESGPGLVKPSETLSLTCTVSGFSTTRFGVHWVRQPPGKGLEWLGV

IWRGGSTDYNAAFVSRLTISKDNSKNQVSLKLSSVTAADTAVYYCSNHYY

GSPDYALDNWGQGTLVTVSS cDNA Encoding Human Light Chain Variable Domain of
1G7.v93
(SEQ ID NO: 19)
gatattcagatgacccagagcccgagcagcctgagcgcgagcgtgggcga tcgcgtgaccattacctgcaaagcgagccaggatgtgagcaacctggtgg tgtggtttcagcagaaacccgggcaaagcgccgaaactgctgatttatagc ggcagctatcgctatagcggcgtgccgagccgctttagcggcagcggcag cggcaccgattttaccctgaccattagcagcctgcagccggaagattttg cgacctattattgccagcagcattatagcccgccgtatacctttggccag ggcaccaaagtggaaattaaa cDNA Encoding Human Heavy Chain Variable Domain of
1G7.v93
(SEQ ID NO: 20)
gaagtgcagctggtggaaagcggcccgggcctggtgaaaccgagcgaaac cctgagcctgacctgcaccgtgagcggctttagcacgacccgctttggcg tgcattgggtgcgccagccgccgggcaaaggcctggaatggctgggcgtg atttggcgcggcggcagcaccgattataacgcggcgtttgtgagccgcct gaccattagcaaagataacagcaaaaaccaggtgagcctgaaactgagca gcgtgaccgcggcggataccgcggtgtattattgcagcaaccattattat ggcagcccgattatgcgctggataactggggccagggcaccctggtgac cgtgagcagc In some embodiments of the CARs described herein, the first antigen-binding domain includes a VL domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the VL domain of 10A8, and/or includes a VH domain that is or includes a sequence that is at least 80% identical (e.g., at least 82%, at least 84%, at least 86%, at least 88%, at least 90%, at least 92%, at least 94%, at least 96%, at least 98%, or at least 99%) identical to the VH domain of 10A8. In some embodiments of the CARs described herein, the first antigen-binding domain includes a VL domain that is or includes the VL domain of 10A8, and/or a VH domain that is or includes the VH domain of 10A8. In some embodiments of any of the CARs described herein, the first antigen-binding domain includes a VL domain that is or includes the sequence of VL of 10A8, except that it includes one, two, three, four, five, six, seven, eight, nine, ten, eleven, twelve, thirteen, fourteen, or fifteen amino acid substitutions, and/or includes a VH domain that is or includes the sequence of VH of 10A8, except that it includes one, two, three, four, five, six, seven, eight, nine, ten, eleven, twelve, thirteen, fourteen, or fifteen amino acid substitutions. In some embodiments, the second antigen-binding domain includes the three CDRs in the light chain variable domain of 10A8, and/or the three CDRs in the heavy chain variable domain of 10A8.

In some examples of any of the CARs described herein, the CAR can bind to a CD307e antigen (e.g., an epitope present in the extracellular domain of CD307e) with a dissociation equilibrium constant ($K_D$) of less than $1\times10^{-5}$ M, less than $0.5\times10^{-5}$ M, less than $1\times10^{-6}$ M, less than $0.5\times10^{6}$ M, less than $1\times10^{-7}$ M, less than $0.5\times10^{-7}$ M, less than $1\times10^{-8}$ M, less than $0.5\times10^{-8}$ M, less than $1\times10^{-9}$ M, less than $0.5\times10^{-9}$, less than $1\times10^{-10}$ M, less than $0.5\times10^{-10}$ M, or less than $1\times10^{-11}$ M (e.g., as measured using surface plasmon resonance).

In some examples of any of the CARs described herein, the CAR can bind to a CD307e antigen (e.g., an epitope present in the extracellular domain of CD307e) with a $K_D$ of about $1\times10^{-11}$ M to about $1\times10^{-5}$ M, about $1\times10^{-11}$ M to about $0.5\times10^{-5}$ M, about $1\times10^{-11}$ M to about $1\times10^{6}$ M, about $1\times10^{-11}$ M to about $0.5\times10^{-6}$ M, about $1\times10^{-11}$ M to about $1\times10^{7}$ M, about $1\times10^{-11}$ M to about $0.5\times10^{-7}$ M, about $1\times10^{-11}$ M to about $1\times10^{-8}$ M, about $1\times10^{-11}$ M to about $0.5\times10^{-8}$ M, about $1\times10^{-11}$ M to about $1\times10^{-9}$ M, about $1\times10^{-11}$ M to about $0.5\times10^{-9}$ M, about $1\times10^{11}$ M to about $1\times10^{-10}$ M, about $1\times10^{-11}$ M to about $0.5\times10^{-10}$ M; about $0.5\times10^{-10}$ M to about $1\times10^{-5}$ M, about $0.5\times10^{-10}$ M to about $0.5\times10^{-5}$ M, about $0.5\times10^{-10}$ M to about $1\times10^{-6}$ M, about $0.5\times10^{-10}$ M to about $0.5\times10^{-6}$ M, about $0.5\times10^{-10}$ M to about $1\times10^{-7}$ M, about $0.5\times10^{-10}$ M to about $0.5\times10^{-7}$ M, about $0.5\times10^{-10}$ M to about $1\times10^{-8}$ M, about $0.5\times10^{-10}$ M to about $0.5\times10^{-8}$ M, about $0.5\times10^{-10}$ M to about $1\times10^{-9}$ M, about $0.5\times10^{-10}$ M to about $0.5\times10^{-9}$ M, about $0.5\times10^{-10}$ M to about $1\times10^{-10}$ M, about $1\times10^{-10}$ M to about $1\times10^{-5}$ M, about $1\times^{-10}$ M to about $0.5\times10^{-5}$ M, about $1\times^{-10}$ M to about $1\times10^{-6}$ M, about $1\times^{-10}$ M to about $0.5\times10^{-11}$ M, about $1\times^{-10}$ M to about $1\times10^{-7}$ M, about $1\times10^{-10}$ M to about $0.5\times10^{-7}$ M, about $1\times10^{-10}$ M to about $1\times10^{-8}$ M, about $1\times10^{-10}$ M to about $0.5\times10^{-8}$ M, about $1\times10^{-10}$ M to about $1\times10^{-9}$ M, about $1\times10^{-10}$ M to about $0.5\times10^{-9}$ M, about $0.5\times10^{-9}$ M to about $1\times10^{-5}$ M, about $0.5\times10^{-9}$ M to about $0.5\times10^{-5}$ M, about $0.5\times10^{-9}$ M to about $1\times10^{6}$ M, about $0.5\times10^{-9}$ M to about $0.5\times10^{-6}$ M, about $0.5\times10^{-9}$ M to about $1\times10^{-7}$ M, about $0.5\times10^{-9}$ M to about $0.5\times10^{-7}$ M, about $0.5\times10^{-9}$ M to about $1\times10^{-8}$ M, about $0.5\times10^{-9}$ M to about $0.5\times10^{-8}$ M, about $0.5\times10^{-9}$ M to about $1\times10^{-9}$ M, about $1\times10^{-9}$ M to about $1\times10^{-5}$ M, about $1\times10^{-9}$ M to about $0.5\times10^{-5}$ M, about $1\times10^{-9}$ M to about $1\times10^{-6}$ M, about $1\times10^{-9}$ M to about $0.5\times10^{-6}$ M, about $1\times10^{-9}$ M to about $1\times10^{-7}$ M, about $1\times10^{-9}$ M to about $0.5\times10^{-7}$M, about $1\times10^{-9}$ M to about $1\times10^{-8}$ M, about $1\times10^{-9}$ M to about $0.5\times10^{-8}$ M, about $0.5\times10^{-8}$ M to about $1\times10^{-5}$ M, about $0.5\times10^{-8}$ M to about $0.5\times10^{-5}$ M, about $0.5\times10^{-8}$ M to about $1\times10^{-6}$ M, about $0.5\times10^{-8}$ M to about $0.5\times10^{-6}$ M, about $0.5\times10^{-8}$ M to about $1\times10^{-7}$ M, about $0.5\times10^{-8}$ M to about $0.5\times10^{-7}$ M, about $0.5\times10^{-8}$ M to about $1\times10^{-8}$ M, about $1\times10^{-8}$ M to about $1\times10^{-5}$ M, about $1\times10^{-8}$ M to about $0.5\times10^{-5}$ M, about $1\times10^{-8}$ M to about $1\times10^{-6}$ M, about $1\times10^{-8}$ M to about $0.5\times10^{-6}$ M, about $1\times10^{-8}$ M to about $1\times10^{-7}$ M, about $1\times10^{-8}$M to about $0.5\times10^{-7}$ M, about $0.5\times10^{-7}$ M to about $1\times10^{-5}$ M, about $0.5\times10^{-7}$ M to about $0.5\times10^{-5}$ M, about $0.5\times10^{-7}$ M to about $1\times10^{-6}$ M, about $0.5\times10^{-7}$ M to about $1\times10^{-7}$ M, about $1\times10^{-6}$ M to about $1\times10^{-5}$ M, about $1\times10^{-5}$ M to about $0.5\times10^{-5}$ M, about $1\times10^{-7}$ M to about $1\times10^{-6}$ M, about $1\times10^{-6}$ M to about $0.5\times10^{-6}$ M, about $0.5\times10^{6}$ M to about $1\times10^{-5}$ M, about $0.5\times10^{-6}$ M to about $0.5\times10^{-5}$ M, about $0.5\times10^{-6}$ M to about $1\times10^{-6}$ M, about $1\times10^{-6}$ M to about $1\times10^{-5}$ M, about $1\times10^{-6}$ M to about $0.5\times10^{-5}$M, or about $0.5\times10^{-5}$ M to about $1\times10^{-5}$ M (e.g., as measured using surface plasmon resonance).

First scFv Linkers and Second scFv Linkers

In some embodiments, the first scFv linker and the second scFv linker are each independently, 1 amino acid to about 50 amino acids, 1 amino acid to about 48 amino acids, 1 amino acid to about 46 amino acids, 1 amino acid to about 44 amino acids, 1 amino acid to about 42 amino acids, 1 amino acid to about 40 amino acids, 1 amino acid to about 38 amino acids, 1 amino acid to about 36 amino acids, 1 amino acid to about 34 amino acids, 1 amino acid to about 32 amino acids, 1 amino acid to about 30 amino acids, 1 amino acid to about 28 amino acids, 1 amino acid to about 26 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, 1 amino acid to about 3 amino acids, about 2 amino acids to about 50 amino acids, about 2 amino acids to about 48 amino acids, about 2 amino acids to about 46 amino acids, about 2 amino acids to about 44 amino acids, about 2 amino acids to about 42 amino acids, about 2 amino acids to about 40 amino acids, about 2 amino acids to about 38 amino acids, about 2 amino acids to about 36 amino acids, about 2 amino acids to about 34 amino acids, about 2 amino acids to about 32 amino acids, about 2 amino acids to about 30 amino acids, about 2 amino acids to about 28 amino acids, about 2 amino acids to about 26 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 50 amino acids, about 4 amino acids to about 48 amino acids, about 4 amino acids to about 46 amino acids, about 4 amino acids to about 44 amino acids, about 4 amino acids to about 42 amino acids, about 4 amino acids to about 40 amino acids, about 4 amino acids to about 38 amino acids, about 4 amino acids to about 36 amino acids, about 4 amino acids to about 34 amino acids, about 4 amino acids to about 32 amino acids, about 4 amino acids to about 30 amino acids, about 4 amino acids to about 28 amino acids, about 4 amino acids to about 26 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 50 amino acids, about 6 amino acids to about 48 amino acids, about 6 amino acids to about 46 amino acids, about 6 amino acids to about 44 amino acids, about 6 amino acids to about 42 amino acids, about 6 amino acids to about 40 amino acids, about 6 amino acids to about 38 amino acids, about 6 amino acids to about 36 amino acids, about 6 amino acids to about 34 amino acids, about 6 amino acids to about 32 amino acids, about 6 amino acids to about 30 amino acids, about 6 amino acids to about 28 amino acids, about 6 amino acids to about 26 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 50 amino acids, about 8 amino acids to about 48 amino acids, about 8 amino acids to about 46 amino acids, about 8 amino acids to about 44 amino acids, about 8 amino acids to about 42 amino acids, about 8 amino acids to about 40 amino acids, about 8 amino acids to about 38 amino acids, about 8 amino acids to about 36 amino acids, about 8 amino acids to about 34 amino acids, about 8 amino acids to about 32 amino acids, about 8 amino acids to about 30 amino acids, about 8 amino acids to about 28 amino acids, about 8 amino acids to about 26 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 50 amino acids, about 10 amino acids to about 48 amino acids, about 10 amino acids to about 46 amino acids, about 10 amino acids to about 44 amino acids, about 10 amino acids to about 42 amino acids, about 10 amino acids to about 40 amino acids, about 10 amino acids to about 38 amino acids, about 10 amino acids to about 36 amino acids, about 10 amino acids to about 34 amino acids, about 10 amino acids to about 32 amino acids, about 10 amino acids to about 30 amino acids, about 10 amino acids to about 28 amino acids, about 10 amino acids to about 26 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 50 amino acids, about 12 amino acids to about 48 amino acids, about 12 amino acids to about 46 amino acids, about 12 amino acids to about 44 amino acids, about 12 amino acids to about 42 amino acids, about 12 amino acids to about 40 amino acids, about 12 amino acids to about 38 amino acids, about 12 amino acids to about 36 amino acids, about 12 amino acids to about 34 amino acids, about 12 amino acids to about 32 amino acids, about 12 amino acids to about 30 amino acids, about 12 amino acids to about 28 amino acids, about 12 amino acids to about 26 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 50 amino acids, about 14 amino acids to about 48 amino acids, about 14 amino acids to about 46 amino acids, about 14 amino acids to about 44 amino acids, about 14 amino acids to about 42 amino acids, about 14 amino acids to about 40 amino acids, about 14 amino acids to about 38 amino acids, about 14 amino acids to about 36 amino acids, about 14 amino acids to about 34 amino acids, about 14 amino acids to about 32 amino acids, about 14 amino acids to about 30 amino acids, about 14 amino acids to about 28 amino acids, about 14 amino acids to about 26 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 50 amino acids, about 16 amino acids to about 48 amino acids, about 16 amino acids to about 46 amino acids, about 16 amino acids to about 44 amino acids, about 16 amino acids to about 42 amino acids, about 16 amino acids to about 40 amino acids, about 16 amino acids to about 38 amino acids, about 16 amino acids to about 36 amino acids, about 16 amino acids to about 34 amino acids, about 16 amino acids to about 32 amino acids, about 16 amino acids to about 30 amino acids, about 16 amino acids to about 28 amino acids, about 16 amino acids to about 26 amino acids, about 16 amino acids to about 24 amino acids, about 16 amino acids to about 22 amino acids, about 16 amino acids to about 20 amino acids, about 16 amino acids to about 18 amino acids, about 18 amino acids to about 50 amino acids, about 18 amino acids to about 48 amino acids, about 18 amino acids to about 46 amino acids, about 18 amino acids to about 44 amino acids, about 18 amino acids to about 42 amino acids, about 18 amino acids to about 40 amino acids, about 18 amino acids to about 38 amino acids, about 18 amino acids to about 36 amino acids, about 18 amino acids to about 34 amino acids, about 18 amino acids to about 32 amino acids, about 18 amino acids to about 30 amino acids, about 18 amino acids to about 28 amino acids, about 18 amino acids to about 26 amino acids, about 18 amino acids to about 24 amino acids, about 18 amino acids to about 22 amino acids, about 18 amino acids to about 20 amino acids, about 20 amino acids to about 50 amino acids, about 20 amino acids to about 48 amino acids, about 20 amino acids to about 46 amino acids, about 20 amino acids to about 44 amino acids, about 20 amino acids to about 42 amino acids, about 20 amino acids to about 40 amino acids, about 20 amino acids to about 38 amino acids, about 20 amino acids to about 36 amino acids, about 20 amino acids to about 34 amino acids, about 20 amino acids to about 32 amino acids, about 20 amino acids to about 30 amino acids, about 20 amino acids to about 28 amino acids, about 20 amino acids to about 26 amino acids, about 20 amino acids to about 24 amino acids, about 20 amino acids to about 22 amino acids, about 22 amino acids to about 50 amino acids, about 22 amino acids to about 48 amino acids, about 22 amino acids to about 46 amino acids, about 22 amino acids to about 44 amino acids, about 22 amino acids to about 42 amino acids, about 22 amino acids to about 40 amino acids, about 22 amino acids to about 38 amino acids, about 22 amino acids to about 36 amino acids, about 22 amino acids to about 34 amino acids, about 22 amino acids to about 32 amino acids, about 22 amino acids to about 30 amino acids, about 22 amino acids to about 28 amino acids, about 22 amino acids to about 26 amino acids, about 22 amino acids to about 24 amino acids, about 24 amino acids to about 50 amino acids, about 24 amino acids to about 48 amino acids, about 24 amino acids to about 46 amino acids, about 24 amino acids to about 44 amino acids, about 24 amino acids to about 42 amino acids, about 24 amino acids to about 40 amino acids, about 24 amino acids to about 38 amino acids, about 24 amino acids to about 36 amino acids, about 24 amino acids to about 34 amino acids, about 24 amino acids to about 32 amino acids, about 24 amino acids to about 30 amino acids, about 24 amino acids to about 28 amino acids, about 24 amino acids to about 26 amino acids, about 26 amino acids to about 50 amino acids, about 26 amino acids to about 48 amino acids, about 26 amino acids to about 46 amino acids, about 26 amino acids to about 44 amino acids, about 26 amino acids to about 42 amino acids, about 26 amino acids to about 40 amino acids, about 26 amino acids to about 38 amino acids, about 26 amino acids to about 36 amino acids, about 26 amino acids to about 34 amino acids, about 26 amino acids to about 32 amino acids, about 26 amino acids to about 30 amino acids, about 26 amino acids to about 28 amino acids, about 28 amino acids to about 50 amino acids, about 28 amino acids to about 48 amino acids, about 28 amino acids to about 46 amino acids, about 28 amino acids to about 44 amino acids, about 28 amino acids to about 42 amino acids, about 28 amino acids to about 40 amino acids, about 28 amino acids to about 38 amino acids, about 28 amino acids to about 36 amino acids, about 28 amino acids to about 34 amino acids, about 28 amino acids to about 32 amino acids, about 28 amino acids to about 30 amino acids, about 30 amino acids to about 50 amino acids, about 30 amino acids to about 48 amino acids, about 30 amino acids to about 46 amino acids, about 30 amino acids to about 44 amino acids, about 30 amino acids to about 42 amino acids, about 30 amino acids to about 40 amino acids, about 30 amino acids to about 38 amino acids, about 30 amino acids to about 36 amino acids, about 30 amino acids to about 34 amino acids, about 30 amino acids to about 32 amino acids, about 32 amino acids to about 50 amino acids, about 32 amino acids to about 48 amino acids, about 32 amino acids to about 46 amino acids, about 32 amino acids to about 44 amino acids, about 32 amino acids to about 42 amino acids, about 32 amino acids to about 40 amino acids, about 32 amino acids to about 38 amino acids, about 32 amino acids to about 36 amino acids, about 32 amino acids to about 34 amino acids, about 34 amino acids to about 50 amino acids, about 34 amino acids to about 48 amino acids, about 34 amino acids to about 46 amino acids, about 34 amino acids to about 44 amino acids, about 34 amino acids to about 42 amino acids, about 34 amino acids to about 40 amino acids, about 34 amino acids to about 38 amino acids, about 34 amino acids to about 36 amino acids, about 36 amino acids to about 50 amino acids, about 36 amino acids to about 48 amino acids, about 36 amino acids to about 46 amino acids, about 36 amino acids to about 44 amino acids, about 36 amino acids to about 42 amino acids, about 36 amino acids to about 40 amino acids, about 36 amino acids to about 38 amino acids, about 38 amino acids to about 50 amino acids, about 38 amino acids to about 48 amino acids, about 38 amino acids to about 46 amino acids, about 38 amino acids to about 44 amino acids, about 38 amino acids to about 42 amino acids, about 38 amino acids to about 40 amino acids, about 40 amino acids to about 50 amino acids, about 40 amino acids to about 48 amino acids, about 40 amino acids to about 46 amino acids, about 40 amino acids to about 44 amino acids, about 40 amino acids to about 42 amino acids, about 42 amino acids to about 50 amino acids, about 42 amino acids to about 48 amino acids, about 42 amino acids to about 46 amino acids, about 42 amino acids to about 44 amino acids, about 44 amino acids to about 50 amino acids, about 44 amino acids to about 48 amino acids, about 44 amino acids to about 46 amino acids, about 46 amino acids to about 50 amino acids, about 46 amino acids to about 48 amino acids, or about 48 amino acids to about 50 amino acids.

In some embodiments, the first scFv linker and the second scFv linker can each independently be or comprise a sequence of (SG)$_n$, where n can be 1, 2, 3, 4, 5, 6, 7, 8, 9, 10, 11, 12, 13, 14, 15, 16, 17, 18, 19, 20, 21, 22, 23, 24, or 25. In some embodiments, the first scFv linker and the second scFv linker can each independently be or comprise a sequence of (GS)$_n$, where n can be 1, 2, 3, 4, 5, 6, 7, 8, 9, 10, 11, 12, 13, 14, 15, 16, 17, 18, 19, 20, 21, 22, 23, 24, or 25.

In some embodiments, the first scFv linker and the second scFv linker can each independently be or comprise a sequence of (SGGS)$_n$, where n can be 1, 2, 3, 4, 5, 6, 7, 8, 9, 10, 11, 12, or 13. In some embodiments, the first scFv linker and the second scFv linker can each independently be or comprise a sequence of (SGGGS)$_n$, where n can be 1, 2, 3, 4, 5, 6, 7, 8, 9, or 10. In some embodiments, the first scFv linker and the second scFv linker can each independently be or comprise a sequence of (SGGGGS)$_n$, where n can be 1, 2, 3, 4, 5, 6, 7, 8, or 9.

In some embodiments, the first scFv linker and/or the second scFv linker can be or include the sequence of SGGGGSGGGGSGGGG (SEQ ID NO: 21).

In some embodiments, the first scFv linker and/or the second scFv linker can be or include the sequence of ASTKGPSVFPLAPSSSGSG (SEQ ID NO: 22).

In some embodiments, the first scFv linker and/or the second scFv linker can be or include the sequence of GGGGSGGGGSGGGGS (SEQ ID NO: 23).

In some embodiments, the first scFv linker and/or the second scFv linker can be a Whitlow linker. In some embodiments, the Whitlow linker has the amino acid sequence of GSTSGSGKPGSGEGSTKG (SEQ ID NO: 100) or the nucleotide sequence encoding the Whitlow linker sequence is (SEQ ID NO: 24)
ggcagcaccagcggcagcggcaaaccgggcagcggcgaaggcagcacca aaggc.

In some embodiments, the first scFv linker and/or the second scFv linker can be a (G$_4$S)$_5$ linker. In some embodiments, the (G$_4$S)$_5$ linker has the amino acid sequence of GGGGSGGGGSGGGGSGGGGSGGGGS (SEQ ID NO: 25) or the nucleotide sequence encoding the (G$_4$S)$_5$ linker sequence of (SEQ ID NO: 26)
ggcggtggtggttctggaggcggtggcagcggtggaggtggctcaggagg aggaggtagcggcggcggaggagt.

In some embodiments, the first scFv linker and the second scFv linker can be or include the same sequence. In some embodiments, the first scFv linker and the second scFv linker can be or include different sequences.

Additional aspects and examples of first scFv linkers and second scFv linkers are known in the art.

Linkers

In some embodiments, the linker between the first antigen-binding domain and the second antigen-binding domain can be 1 amino acid to about 250 amino acids, 1 amino acid to about 240 amino acids, 1 amino acid to about 230 amino acids, 1 amino acid to about 220 amino acids, 1 amino acid to about 210 amino acids, 1 amino acid to about 200 amino acids, 1 amino acid to about 190 amino acids, 1 amino acid to about 180 amino acids, 1 amino acid to about 170 amino acids, 1 amino acid to about 160 amino acids, 1 amino acid to about 150 amino acids, 1 amino acid to about 140 amino acids, 1 amino acid to about 130 amino acids, 1 amino acid to about 120 amino acids, 1 amino acid to about 110 amino acids, 1 amino acid to about 100 amino acids, 1 amino acid to about 95 amino acids, 1 amino acid to about 90 amino acids, 1 amino acid to about 85 amino acids, 1 amino acid to about 80 amino acids, 1 amino acid to about 75 amino acids, 1 amino acid to about 70 amino acids, 1 amino acid to about 65 amino acids, 1 amino acid to about 60 amino acids, 1 amino acid to about 55 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 20 amino acids, 1 amino acid to about 15 amino acids, 1 amino acid to about 10 amino acids, 1 amino acid to about 5 amino acids, about 5 amino acids to about 250 amino acids, about 5 amino acids to about 240 amino acids, about 5 amino acids to about 230 amino acids, about 5 amino acids to about 220 amino acids, about 5 amino acids to about 210 amino acids, about 5 amino acids to about 200 amino acids, about 5 amino acids to about 190 amino acids, about 5 amino acids to about 180 amino acids, about 5 amino acids to about 170 amino acids, about 5 amino acids to about 160 amino acids, about 5 amino acids to about 150 amino acids, about 5 amino acids to about 140 amino acids, about 5 amino acids to about 130 amino acids, about 5 amino acids to about 120 amino acids, about 5 amino acids to about 110 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 250 amino acids, about 10 amino acids to about 240 amino acids, about 10 amino acids to about 230 amino acids, about 10 amino acids to about 220 amino acids, about 10 amino acids to about 210 amino acids, about 10 amino acids to about 200 amino acids, about 10 amino acids to about 190 amino acids, about 10 amino acids to about 180 amino acids, about 10 amino acids to about 170 amino acids, about 10 amino acids to about 160 amino acids, about 10 amino acids to about 150 amino acids, about 10 amino acids to about 140 amino acids, about 10 amino acids to about 130 amino acids, about 10 amino acids to about 120 amino acids, about 10 amino acids to about 110 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 250 amino acids, about 15 amino acids to about 240 amino acids, about 15 amino acids to about 230 amino acids, about 15 amino acids to about 220 amino acids, about 15 amino acids to about 210 amino acids, about 15 amino acids to about 200 amino acids, about 15 amino acids to about 190 amino acids, about 15 amino acids to about 180 amino acids, about 15 amino acids to about 170 amino acids, about 15 amino acids to about 160 amino acids, about 15 amino acids to about 150 amino acids, about 15 amino acids to about 140 amino acids, about 15 amino acids to about 130 amino acids, about 15 amino acids to about 120 amino acids, about 15 amino acids to about 110 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 250 amino acids, about 20 amino acids to about 240 amino acids, about 20 amino acids to about 230 amino acids, about 20 amino acids to 220 amino acids, about 20 amino acids to about 210 amino acids, about 20 amino acids to about 200 amino acids, about 20 amino acids to about 190 amino acids, about 20 amino acids to about 180 amino acids, about 20 amino acids to about 170 amino acids, about 20 amino acids to about 160 amino acids, about 20 amino acids to about 150 amino acids, about 20 amino acids to about 140 amino acids, about 20 amino acids to about 130 amino acids, about 20 amino acids to about 120 amino acids, about 20 amino acids to about 110 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 250 amino acids, about 25 amino acids to about 240 amino acids, about 25 amino acids to about 230 amino acids, about 25 amino acids to about 220 amino acids, about 25 amino acids to about 210 amino acids, about 25 amino acids to about 200 amino acids, about 25 amino acids to about 190 amino acids, about 25 amino acids to about 180 amino acids, about 25 amino acids to about 170 amino acids, about 25 amino acids to about 160 amino acids, about 25 amino acids to about 150 amino acids, about 25 amino acids to about 140 amino acids, about 25 amino acids to about 130 amino acids, about 25 amino acids to about 120 amino acids, about 25 amino acids to about 110 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 250 amino acids, about 30 amino acids to about 240 amino acids, about 30 amino acids to about 230 amino acids, about 30 amino acids to about 220 amino acids, about 30 amino acids to about 210 amino acids, about 30 amino acids to about 200 amino acids, about 30 amino acids to about 190 amino acids, about 30 amino acids to about 180 amino acids, about 30 amino acids to about 170 amino acids, about 30 amino acids to about 160 amino acids, about 30 amino acids to about 150 amino acids, about 30 amino acids to about 140 amino acids, about 30 amino acids to about 130 amino acids, about 30 amino acids to about 120 amino acids, about 30 amino acids to about 110 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 250 amino acids, about 35 amino acids to about 240 amino acids, about 35 amino acids to about 230 amino acids, about 35 amino acids to about 220 amino acids, about 35 amino acids to about 210 amino acids, about 35 amino acids to about 200 amino acids, about 35 amino acids to about 190 amino acids, about 35 amino acids to about 180 amino acids, about 35 amino acids to about 170 amino acids, about 35 amino acids to about 160 amino acids, about 35 amino acids to about 150 amino acids, about 35 amino acids to about 140 amino acids, about 35 amino acids to about 130 amino acids, about 35 amino acids to about 120 amino acids, about 35 amino acids to about 110 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 250 amino acids, about 40 amino acids to about 240 amino acids, about 40 amino acids to about 230 amino acids, about 40 amino acids to about 220 amino acids, about 40 amino acids to about 210 amino acids, about 40 amino acids to about 200 amino acids, about 40 amino acids to about 190 amino acids, about 40 amino acids to about 180 amino acids, about 40 amino acids to about 170 amino acids, about 40 amino acids to about 160 amino acids, about 40 amino acids to about 150 amino acids, about 40 amino acids to about 140 amino acids, about 40 amino acids to about 130 amino acids, about 40 amino acids to about 120 amino acids, about 40 amino acids to about 110 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 250 amino acids, about 45 amino acids to about 240 amino acids, about 45 amino acids to about 230 amino acids, about 45 amino acids to about 220 amino acids, about 45 amino acids to about 210 amino acids, about 45 amino acids to about 200 amino acids, about 45 amino acids to about 190 amino acids, about 45 amino acids to about 180 amino acids, about 45 amino acids to about 170 amino acids, about 45 amino acids to about 160 amino acids, about 45 amino acids to about 150 amino acids, about 45 amino acids to about 140 amino acids, about 45 amino acids to about 130 amino acids, about 45 amino acids to about 120 amino acids, about 45 amino acids to about 110 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 250 amino acids, about 50 amino acids to about 240 amino acids, about 50 amino acids to about 230 amino acids, about 50 amino acids to about 220 amino acids, about 50 amino acids to about 210 amino acids, about 50 amino acids to about 200 amino acids, about 50 amino acids to about 190 amino acids, about 50 amino acids to about 180 amino acids, about 50 amino acids to about 170 amino acids, about 50 amino acids to about 160 amino acids, about 50 amino acids to about 150 amino acids, about 50 amino acids to about 140 amino acids, about 50 amino acids to about 130 amino acids, about 50 amino acids to about 120 amino acids, about 50 amino acids to about 110 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 250 amino acids, about 55 amino acids to about 240 amino acids, about 55 amino acids to about 230 amino acids, about 55 amino acids to about 220 amino acids, about 55 amino acids to about 210 amino acids, about 55 amino acids to about 200 amino acids, about 55 amino acids to about 190 amino acids, about 55 amino acids to about 180 amino acids, about 55 amino acids to about 170 amino acids, about 55 amino acids to about 160 amino acids, about 55 amino acids to about 150 amino acids, about 55 amino acids to about 140 amino acids, about 55 amino acids to about 130 amino acids, about 55 amino acids to about 120 amino acids, about 55 amino acids to about 110 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 250 amino acids, about 60 amino acids to about 240 amino acids, about 60 amino acids to about 230 amino acids, about 60 amino acids to about 220 amino acids, about 60 amino acids to about 210 amino acids, about 60 amino acids to about 200 amino acids, about 60 amino acids to about 190 amino acids, about 60 amino acids to about 180 amino acids, about 60 amino acids to about 170 amino acids, about 60 amino acids to about 160 amino acids, about 60 amino acids to about 150 amino acids, about 60 amino acids to about 140 amino acids, about 60 amino acids to about 130 amino acids, about 60 amino acids to about 120 amino acids, about 60 amino acids to about 110 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 250 amino acids, about 65 amino acids to about 240 amino acids, about 65 amino acids to about 230 amino acids, about 65 amino acids to about 220 amino acids, about 65 amino acids to about 210 amino acids, about 65 amino acids to about 200 amino acids, about 65 amino acids to about 190 amino acids, about 65 amino acids to about 180 amino acids, about 65 amino acids to about 170 amino acids, about 65 amino acids to about 160 amino acids, about 65 amino acids to about 150 amino acids, about 65 amino acids to about 140 amino acids, about 65 amino acids to about 130 amino acids, about 65 amino acids to about 120 amino acids, about 65 amino acids to about 110 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 250 amino acids, about 70 amino acids to about 240 amino acids, about 70 amino acids to about 230 amino acids, about 70 amino acids to about 220 amino acids, about 70 amino acids to about 210 amino acids, about 70 amino acids to about 200 amino acids, about 70 amino acids to about 190 amino acids, about 70 amino acids to about 180 amino acids, about 70 amino acids to about 170 amino acids, about 70 amino acids to about 160 amino acids, about 70 amino acids to about 150 amino acids, about 70 amino acids to about 140 amino acids, about 70 amino acids to about 130 amino acids, about 70 amino acids to about 120 amino acids, about 70 amino acids to about 110 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 250 amino acids, about 75 amino acids to about 240 amino acids, about 75 amino acids to about 230 amino acids, about 75 amino acids to about 220 amino acids, about 75 amino acids to about 210 amino acids, about 75 amino acids to about 200 amino acids, about 75 amino acids to about 190 amino acids, about 75 amino acids to about 180 amino acids, about 75 amino acids to about 170 amino acids, about 75 amino acids to about 160 amino acids, about 75 amino acids to about 150 amino acids, about 75 amino acids to about 140 amino acids, about 75 amino acids to about 130 amino acids, about 75 amino acids to about 120 amino acids, about 75 amino acids to about 110 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 250 amino acids, about 80 amino acids to about 240 amino acids, about 80 amino acids to about 230 amino acids, about 80 amino acids to about 220 amino acids, about 80 amino acids to about 210 amino acids, about 80 amino acids to about 200 amino acids, about 80 amino acids to about 190 amino acids, about 80 amino acids to about 180 amino acids, about 80 amino acids to about 170 amino acids, about 80 amino acids to about 160 amino acids, about 80 amino acids to about 150 amino acids, about 80 amino acids to about 140 amino acids, about 80 amino acids to about 130 amino acids, about 80 amino acids to about 120 amino acids, about 80 amino acids to about 110 amino acids, about 80 amino acids to about 100 amino acids, about 80 amino acids to about 95 amino acids, about 80 amino acids to about 90 amino acids, about 80 amino acids to about 85 amino acids, about 85 amino acids to about 250 amino acids, about 85 amino acids to about 240 amino acids, about 85 amino acids to about 230 amino acids, about 85 amino acids to about 220 amino acids, about 85 amino acids to about 210 amino acids, about 85 amino acids to about 200 amino acids, about 85 amino acids to about 190 amino acids, about 85 amino acids to about 180 amino acids, about 85 amino acids to about 170 amino acids, about 85 amino acids to about 160 amino acids, about 85 amino acids to about 150 amino acids, about 85 amino acids to about 140 amino acids, about 85 amino acids to about 130 amino acids, about 85 amino acids to about 120 amino acids, about 85 amino acids to about 110 amino acids, about 85 amino acids to about 100 amino acids, about 85 amino acids to about 95 amino acids, about 85 amino acids to about 90 amino acids, about 90 amino acids to about 250 amino acids, about 90 amino acids to about 240 amino acids, about 90 amino acids to about 230 amino acids, about 90 amino acids to about 220 amino acids, about 90 amino acids to about 210 amino acids, about 90 amino acids to about 200 amino acids, about 90 amino acids to about 190 amino acids, about 90 amino acids to about 180 amino acids, about 90 amino acids to about 170 amino acids, about 90 amino acids to about 160 amino acids, about 90 amino acids to about 150 amino acids, about 90 amino acids to about 140 amino acids, about 90 amino acids to about 130 amino acids, about 90 amino acids to about 120 amino acids, about 90 amino acids to about 110 amino acids, about 90 amino acids to about 100 amino acids, about 90 amino acids to about 95 amino acids, about 95 amino acids to about 250 amino acids, about 95 amino acids to about 240 amino acids, about 95 amino acids to about 230 amino acids, about 95 amino acids to about 220 amino acids, about 95 amino acids to about 210 amino acids, about 95 amino acids to about 200 amino acids, about 95 amino acids to about 190 amino acids, about 95 amino acids to about 180 amino acids, about 95 amino acids to about 170 amino acids, about 95 amino acids to about 160 amino acids, about 95 amino acids to about 150 amino acids, about 95 amino acids to about 140 amino acids, about 95 amino acids to about 130 amino acids, about 95 amino acids to about 120 amino acids, about 95 amino acids to about 110 amino acids, about 95 amino acids to about 100 amino acids, about 100 amino acids to about 250 amino acids, about 100 amino acids to about 240 amino acids, about 100 amino acids to about 230 amino acids, about 100 amino acids to about 220 amino acids, about 100 amino acids to about 210 amino acids, about 100 amino acids to about 200 amino acids, about 100 amino acids to about 190 amino acids, about 100 amino acids to about 180 amino acids, about 100 amino acids to about 170 amino acids, about 100 amino acids to about 160 amino acids, about 100 amino acids to about 150 amino acids, about 100 amino acids to about 140 amino acids, about 100 amino acids to about 130 amino acids, about 100 amino acids to about 120 amino acids, about 100 amino acids to about 110 amino acids, about 120 amino acids to about 250 amino acids, about 120 amino acids to about 240 amino acids, about 120 amino acids to about 230 amino acids, about 120 amino acids to about 220 amino acids, about 120 amino acids to about 210 amino acids, about 120 amino acids to about 200 amino acids, about 120 amino acids to about 190 amino acids, about 120 amino acids to about 180 amino acids, about 120 amino acids to about 170 amino acids, about 120 amino acids to about 160 amino acids, about 120 amino acids to about 150 amino acids, about 120 amino acids to about 140 amino acids, about 120 amino acids to about 130 amino acids, about 130 amino acids to about 250 amino acids, about 130 amino acids to about 240 amino acids, about 130 amino acids to about 230 amino acids, about 130 amino acids to about 220 amino acids, about 130 amino acids to about 210 amino acids, about 130 amino acids to about 200 amino acids, about 130 amino acids to about 190 amino acids, about 130 amino acids to about 180 amino acids, about 130 amino acids to about 170 amino acids, about 130 amino acids to about 160 amino acids, about 130 amino acids to about 150 amino acids, about 130 amino acids to about 140 amino acids, about 140 amino acids to about 250 amino acids, about 140 amino acids to about 240 amino acids, about 140 amino acids to about 230 amino acids, about 140 amino acids to about 220 amino acids, about 140 amino acids to about 210 amino acids, about 140 amino acids to about 200 amino acids, about 140 amino acids to about 190 amino acids, about 140 amino acids to about 180 amino acids, about 140 amino acids to about 170 amino acids, about 140 amino acids to about 160 amino acids, about 140 amino acids to about 150 amino acids, about 150 amino acids to about 250 amino acids, about 150 amino acids to about 240 amino acids, about 150 amino acids to about 230 amino acids, about 150 amino acids to about 220 amino acids, about 150 amino acids to about 210 amino acids, about 150 amino acids to about 200 amino acids, about 150 amino acids to about 190 amino acids, about 150 amino acids to about 180 amino acids, about 150 amino acids to about 170 amino acids, about 150 amino acids to about 160 amino acids, about 160 amino acids to about 250 amino acids, about 160 amino acids to about 240 amino acids, about 160 amino acids to about 230 amino acids, about 160 amino acids to about 220 amino acids, about 160 amino acids to about 210 amino acids, about 160 amino acids to about 200 amino acids, about 160 amino acids to about 190 amino acids, about 160 amino acids to about 180 amino acids, about 160 amino acids to about 170 amino acids, about 170 amino acids to about 250 amino acids, about 170 amino acids to about 240 amino acids, about 170 amino acids to about 230 amino acids, about 170 amino acids to about 220 amino acids, about 170 amino acids to about 210 amino acids, about 170 amino acids to about 200 amino acids, about 170 amino acids to about 190 amino acids, about 170 amino acids to about 180 amino acids, about 180 amino acids to about 250 amino acids, about 180 amino acids to about 240 amino acids, about 180 amino acids to about 230 amino acids, about 180 amino acids to about 220 amino acids, about 180 amino acids to about 210 amino acids, about 180 amino acids to about 200 amino acids, about 180 amino acids to about 190 amino acids, about 190 amino acids to about 250 amino acids, about 190 amino acids to about 240 amino acids, about 190 amino acids to about 230 amino acids, about 190 amino acids to about 220 amino acids, about 190 amino acids to about 210 amino acids, about 190 amino acids to about 200 amino acids, about 200 amino acids to about 250 amino acids, about 200 amino acids to about 240 amino acids, about 200 amino acids to about 230 amino acids, about 200 amino acids to 220 amino acids, about 200 amino acids to about 210 amino acids, about 210 amino acids to about 250 amino acids, about 210 amino acids to about 240 amino acids, about 210 amino acids to about 230 amino acids, about 210 amino acids to about 220 amino acids, about 220 amino acids to about 250 amino acids, about 220 amino acids to about 240 amino acids, about 220 amino acids to about 230 amino acids, about 230 amino acids to about 250 amino acids, about 230 amino acids to about 240 amino acids, or about 240 amino acids to about 250 amino acids.

In some embodiments, the linker can be or can include one or more of an IgG1, IgG2, IgG3, or IgG4 CH1, CH2, and CH3 domain. In some embodiments, the linker can be or can include CH2-CH3 human IgG1 domains. In some embodiments, the CH2-CH3 human IgG1 domains have a sequence of:

```
                                    (SEQ ID NO: 27)
AEPKSPDKTHTCPPCPAPPVAGPSVFLFPPKPKDTLMIARTPEVTCWVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGKKD.
```

In some embodiments, the linker can be or include a portion of the human CD8 extracellular sequence that is proximal to the human CD8 transmembrane domain. For example, the linker can be or include human CD8 sequence of

```
                                    (SEQ ID NO: 28)
   TTTPAPRPPTPAPTIASQPLSLRPEACRPAAGGAVHTRGLDFACDI.
```

In some embodiments, the linker can be or include a human IgG1 hinge sequence. In some embodiments, the human IgG1 hinge sequence is

```
                                    (SEQ ID NO: 29)
              AEPKSPDKTHTCPPCPKDPK.
```

In some embodiments, the linker is or includes a GS connector. An example of a GS connector is a $(G_4S)5$ linker. In some embodiments, the $(G_4S)_5$ linker amino acid sequence is (SEQ ID NO: 25), or the nucleic acid encoding a (G4S)5 linker (SEQ ID NO: 26).

In some embodiments, the linker has an alpha helix structure. In some embodiments, the linker is a coiled coil domain. Additional aspects and examples of linkers are known in the art.

BCMA

As used herein "B-cell maturation protein (BCMA)", "tumor necrosis factor receptor superfamily member 17 (TNFRSF17)" and "CD269" are interchangeable. The BCMA gene encodes a TNF superfamily receptor, a protein that is expressed in, e.g., mature B lymphocytes and plasma cells (see, e.g., Laabi et al., *Nucleic Acid Res.* 22:1147-1154, 1994; and O'Connor et al., *J. Exp. Med.* 199: 91-97, 2004). BCMA binds to B-cell activating factor (BAF) and to a proliferation inducing ligand (APRIL) (see, e.g., Kalled, *Immunol. Rev.* 204: 43-54, 2005; Mackay et al., *Ann. Rev. Immunol.* 231-264, 2003). BCMA is over-expressed in various cancer, including multiple myeloma (Novak et al., *Blood* 103(2): 689-694, 2004), glioblastoma (Deshayes et al., *Oncogene* 23(17):3005-3012, 2004), chronic lymphocytic leukemia (Novak et al., *Blood* 100(8): 2973-2979, 2002) and Hodgkin lymphoma (Chiu et al., *Blood* 109(2): 729-739, 2007).

Exemplary sequences of BCMA and exemplary sequences of nucleic acids encoding BCMA are provided below.

Human BCMA. Extracellular domain shown in bold.
(SEQ ID NO: 30)

1 **mlqmagqcsq neyfdsllha cipcqlrcss ntppltcqry cnasvtnsvk
    gtna**ilwtcl 61 glsliislav fvlmfllrki nse-
    plkdefk ntgsgllgma nidleksrtg deiilprgle 121 ytveectced cikskpkvds dhcfplpame egatilvttk tndyckslpa
    alsateieks 181 isar cDNA encoding Human BCMA. Sequence encoding
extracellular domain shown in bold.
(SEQ ID NO: 31)

1 aagactcaaa cttagaaact tgaattagat gtggtattca aatccttagc
    tgccgcgaag 61 acacagacag cccccgtaag aacccacgaa gcaggcgaag ttcattgttc
    tcaacattct 121 agctgctctt gctgcatttg ctctggaatt cttgtagaga tattacttgt
    ccttccaggc 181 tgttctttct gtagctccct gttttctttt tgtgatcat gttgcagatg
    gctgggcagt 241 gctcccaaaa tgaatatttt gacagtttgt tgcatgcttg cataccttgt
    caacttcgat 301 gttcttctaa tactcctcct ctaacatgtc agcgttattg taatgcaagt
    gtgaccaatt 361 cagtgaaagg aacgaatgcg **attctctgga cctgtttggg actgagctta
    ataatttctt**

421 **tggcagtttt cgtgctaatg ttttttgctaa ggaagataaa ctctgaacca
    ttaaaggacg**

481 agtttaaaaa cacaggatca ggtctcctgg gcatggctaa cattgacctg
    gaaaagagca 541 ggactggtga tgaaattatt cttccgagag gcctcgagta cacggtggaa
    gaatgcacct 601 gtgaagactg catcaagagc aaaccgaagg tcgactctga ccattgcttt
    ccactcccag 661 ctatggagga aggcgcaacc attcttgtca ccacgaaaac gaatgactat
    tgcaagagcc 721 tgccagctgc tttgagtgct acggagatag agaaatcaat ttctgctagg
    taattaacca 781 tttcgactcg agcagtgcca ctttaaaaat cttttgtcag aatagatgat
    gtgtcagatc 841 tctttaggat gactgtamttt ttcagttgcc gatacagctt tttgtcctct
    aactgtggaa 901 actctttatg ttagatatat ttctctaggt tactgttggg agcttaatgg
    tagaaacttc 961 cttggtttca tgattaaact ctttttttc ctga Human BCMA Transcript Variant 4
(SEQ ID NO: 32)

1 mlqmagqcsq neyfdsllha cipcqlrcss ntppltcqry cnarsgllgm
    anidleksrt 61 gdeiilprgl eytveectce dcikskpkvd sdhcfplpam eegatilvtt
    ktndyckslp 121 aalsateiek sisar cDNA Encoding Human BCMA Transcript Variant 4
(SEQ ID NO: 33)

```
  1 gttctcaaca ttctagctgc tcttgctgca tttgctctgg aattcttgta
    gagatattac 61 ttgtccttcc aggctgttct ttctgtagct cccttgtttt cttttgtga
    tcatgttgca 121 gatggctggg cagtgctccc aaaatgaata ttttgacagt ttgttgcatg
    cttgcatacc 181 ttgtcaactt cgatgttctt ctaatactcc tcctctaaca tgtcagcgtt
    attgtaatgc 241 aagatcaggt ctcctgggca tggctaacat tgacctggaa aagagcagga
    ctggtgatga 301 aattattctt ccgagaggcc tcgagtacac ggtggaagaa tgcacctgtg
    aagactgcat 361 caagagcaaa ccgaaggtcg actctgacca ttgctttcca ctcccagcta
    tggaggaagg 421 cgcaaccatt cttgtcacca cgaaaacgaa tgactattgc aagagcctgc
    cagctgcttt 481 gagtgctacg gagatagaga aatcaatttc tgctaggtaa ttaaccattt
    cgactcgagc 541 agtgccactt taaaaatctt ttgtcagaat agatgatgtg tcagatctct
    ttaggatgac 601 tgtattttc  agttgccgat acagcttttt gtcctctaac tgtggaaact
    ctttatgtta 661 gatatatt
```

CD307e

As used herein the terms "Fc receptor-like protein 5 (FCRL5)", "CD307", "CD307e", "10A8", "1G7", "FcRH5" and "Immunoglobulin superfamily receptor translocation associated 2 (IRTA2)" are interchangeable. The FCRL5 gene encodes a member of the immunoglobulin receptor superfamily and the Fc-receptor like family, a protein that is expressed, e.g., in B cells and plasma cells (see, e.g. Li et al., *J. Immunol.* 196(10): 4064-4074, 2016). FCRL5 has been associated with diseases, e.g., multiple myeloma (Ise et al., *Leukemia* 21:169-174, 2007; and Elkins et al., *Mol. Cancer Ther.* 11:2222-2232, 2012), hairy cell leukemia (Janik, *Leuk. Lymphoma* 52:69-71, 2011) and Burkitt lymphoma (Mohan et al., *Blood* 107(11):4433-4439, 2006).

Exemplary sequences of CD307e and exemplary sequences of nucleic acids encoding CD307e are provided below.

Human CD307e Isoform 1 Precursor Protein (SEQ ID NO: 34).

The signal sequence is underlined. The extracellular domain present in mature protein in shown in bold.

```
  1 mllwvillvl apvsgqfart prpiiflqpp wttvfqgerv tltckgfrfy
    spqktkwyhr 61 ylgkeilret pdnilevqes geyrcqaqgs plsspvhldf ssaslilqap
    lsvfegdsvv 121 lrcrakaevt lnntiykndn vlaflnkrtd fhiphaclkd ngayrctgyk
    esccpvssnt 181 vkiqvqepft rpvlrassfq pisgnpvtlt cetqlslers dvplrfrffr
    ddqtlglgws 241 lspnfqitam wskdsgfywc kaatmpysvi sdsprswiqv qipashpvlt
    lspekalnfe 301 gtkvtlhcet qedslrtlyr fyhegvplrh ksvrcergas isfslttens
    gnyyctadng 361 lgakpskavs lsvtvpvshp vlnlsspedl ifegakvtlh ceaqrgslpi
    lyqfhhegaa 421 lerrsansag gvaisfslta ehsgnyycta dngfgpqrsk avslsvtvpv
    shpvltlssa 481 ealtfegatv tlhcevqrgs pqilyqfyhe dmplwssstp svgrvsfsfs
    lteghsgnyy
```

-continued

```
541 ctadngfgpq rsevvslfvt vpvsrpiltl rvpraqavvg dllelhceap
    rgsppilywf 601 yhedvtlgss sapsggeasf nlsltaehsg nysceanngl vaqhsdtisl
    svivpvsrpi 661 ltfrapraqa vvgdllelhc ealrgsspil ywfyhedvtl gkisapsggg
    asfnlsltte 721 hsgiyscead ngleaqrsem vtlkvavpvs rpvltlrapg thaavgdlle
    lhcealrgsp 781 lilyrffhed vtlgnrssps ggaslnlslt aehsgnysce adnglgaqrs
    etvtlyitgl 841 tanrsgpfat gvaggllsia glaagallly cwlsrkagrk pasdparsps
    dsdsqeptyh 901 nvpaweelqp vytnanprge nvvysevrii qekkkhavas dprhlrnkgs
    piiysevkva 961 stpvsgslfl assaphr
``` cDNA Encoding Human CD307e Isoform 1 Precursor Protein (SEQ ID NO: 35).

Sequence encoding the signal sequence is underlined. The sequence encoding the extracellular domain present in mature protein in shown in bold.

```
  1 aattcactaa tgcattctgc tcttttttgag agcacagctt ctcagatgtg
    ctccttggag 61 ctggtgtgca gtgtcctgac tgtaagatca agtccaaacc tgttttggaa
    ttgaggaaac 121 ttctcttttg atctcagccc ttggtggtcc aggtcttcat gctgctgtgg
    gtgatattac 181 tggtcctggc tcctgtcagt ggacagtttg caaggacacc caggcccatt
    attttcctcc 241 agcctccatg gaccacagtc ttccaaggag agagagtgac cctcacttgc
    aagggatttc 301 gcttctactc accacagaaa acaaaatggt accatcggta ccttgggaaa
    gaaatactaa 361 gagaaacccc agacaatatc cttgaggttc aggaatctgg agagtacaga
    tgccaggccc 421 agggctcccc tctcagtagc cctgtgcact tggatttttc ttcagcttcg
    ctgatcctgc 481 aagctccact ttctgtgttt gaaggagact ctgtggttct gaggtgccgg
    gcaaaggcgg 541 aagtaacact gaataatact atttacaaga atgataatgt cctggcattc
    cttaataaaa 601 gaactgactt ccatattcct catgcatgtc tcaaggacaa tggtgcatat
    cgctgtactg 661 gatataagga aagttgttgc cctgtttctt ccaatacagt caaaatccaa
    gtccaagagc 721 catttacacg tccagtgctg agagccagct ccttccagcc catcagcggg
    aacccagtga 781 ccctgacctg tgagacccag ctctctctag agaggtcaga tgtcccgctc
    cggttccgct 841 tcttcagaga tgaccagacc ctgggattag ctggagtct ctccccgaat
    ttccagatta 901 ctgccatgtg gagtaaagat tcagggttct actggtgtaa ggcagcaaca
    atgccttaca
```

-continued

```
 961 gcgtcatatc tgacagcccg agatcctgga tacaggtgca gatccctgca
     tctcatcctg 1021 tcctcactct cagccctgaa aaggctctga attttgaggg aaccaaggtg
     acacttcact 1081 gtgaaaccca ggaagattct ctgcgcactt tgtacaggtt ttatcatgag
     ggtgtccccc 1141 tgaggcacaa gtcagtccgc tgtgaaaggg gagcatccat cagcttctca
     ctgactacag 1201 agaattcagg gaactactac tgcacagctg acaatggcct tggcgccaag
     cccagtaagg 1261 ctgtgagcct ctcagtcact gttcccgtgt ctcatcctgt cctcaacctc
     agctctcctg 1321 aggacctgat ttttgaggga gccaaggtga cacttcactg tgaagcccag
     agaggttcac 1381 tccccatcct gtaccagttt catcatgagg gtgctgccct ggagcgtagg
     tcggccaact 1441 ctgcaggagg agtggccatc agcttctctc tgactgcaga gcattcaggg
     aactactact 1501 gcacagctga caatggcttt ggcccccagc gcagtaaggc ggtgagcctc
     tccgtcactg 1561 tccctgtgtc tcatcctgtc ctcaccctca gctctgctga ggccctgact
     tttgaaggag 1621 ccactgtgac acttcactgt gaagtccaga gaggttcccc acaaatccta
     taccagtttt 1681 atcatgagga catgccctg tggagcagct caacaccctc tgtgggaaga
     gtgtccttca 1741 gcttctctct gactgaagga cattcaggga attactactg cacagctgac
     aatggctttg 1801 gtccccagcg cagtgaagtg gtgagccttt ttgtcactgt tccagtgtct
     cgccccatcc 1861 tcaccctcag ggttcccagg gcccaggctg tggtggggga cctgctggag
     cttcactgtg 1921 aggccccgag aggctctccc ccaatcctgt actggtttta tcatgaggat
     gtcaccctgg 1981 ggagcagctc agcccctct ggaggagaag cttctttcaa cctctctctg
     actgcagaac 2041 attctggaaa ctactcatgt gaggccaaca atggcctagt ggcccagcac
     agtgacacaa 2101 tatcactcag tgttatagtt ccagtatctc gtcccatcct caccttcagg
     gctcccaggg 2161 cccaggctgt ggtgggggac ctgctggagc ttcactgtga ggccctgaga
     ggctcctccc 2221 caatcctgta ctggttttat catgaagatg tcaccctggg taagatctca
     gcccctctg 2281 gaggagggc ctccttcaac ctctctctga ctacagaaca ttctggaatc
     tactcctgtg 2341 aggcagacaa tggtctggag gcccagcgca gtgagatggt gacactgaaa
     gttgcagttc 2401 cggtgtctcg cccggtcctc accctcaggg ctcccgggac ccatgctgcg
     gtggggacc 2461 tgctggagct tcactgtgag gccctgagag gctctcccct gatcctgtac
     cggttttttc 2521 atgaggatgt caccctagga aataggtcgt cccctctgg aggagcgtcc
     ttaaacctct
```

```
2581 ctctgactgc agagcactct ggaaactact cctgtgaggc cgacaatggc
     ctcggggccc 2641 agcgcagtga gacagtgaca ctttatatca cagggctgac cgcgaacaga
     agtggccctt 2701 ttgccacagg agtcgccggg ggcctgctca gcatagcagg ccttgctgcg
     ggggcactgc 2761 tgctctactg ctggctctcg agaaaagcag ggagaaagcc tgcctctgac
     cccgccagga 2821 gcccttcaga ctcggactcc caagagccca cctatcacaa tgtaccagcc
     tgggaagagc 2881 tgcaaccagt gtacactaat gcaaatccta gaggagaaaa tgtggtttac
     tcagaagtac 2941 ggatcatcca agagaaaaag aaacatgcag tggcctctga ccccaggcat
     ctcaggaaca 3001 agggttcccc tatcatctac tctgaagtta aggtggcgtc aaccccggtt
     tccggatccc 3061 tgttcttggc ttcctcagct cctcacagat gagtccacac gtctctccaa
     ctgctgtttc 3121 agcctctgca ccccaaagtt ccccttgggg gagaagcagc attgaagtgg
     gaagatttag 3181 gctgccccag accatatcta ctggcctttg tttcacatgt cctcattctc
     agtctgacca 3241 gaatgcaggg ccctgctgga ctgtcacctg tttcccagtt aaagccctga
     ctggcaggtt 3301 ttttaatcca gtggcaaggt gctcccactc cagggcccag cacatctcct
     ggattcctta 3361 gtgggcttca gctgtggttg ctgttctgag tactgctctc atcacacccc
     cacagagggg 3421 gtcttaccac acaaagggag agtgggcctt caggagatgc cgggctggcc
     taacagctca 3481 ggtgctccta aactccgaca cagagttcct gctttgggtg gatgcatttc
     tcaattgtca 3541 tcagcctggt ggggctactg cagtgtgctg ccaaatggga cagcacacag
     cctgtgcaca 3601 tgggacatgt gatgggtctc cccacggggg ctgcatttca cactcctcca
     cctgtctcaa 3661 actctaaggt cggcacttga caccaaggta acttctctcc tgctcatgtg
     tcagtgtcta 3721 cctgcccaag taagtggctt tcatacacca agtcccaagt tcttcccatc
     ctaacagaag 3781 taacccagca agtcaaggcc aggaggacca ggggtgcaga cagaacacat
     actggaacac 3841 aggaggtgct caattactat ttgactgact gactgaatga atgaatgaat
     gaggaagaaa 3901 actgtgggta atcaaactgg cataaaatcc agtgcactcc ctaggaaatc
     cgggaggtat 3961 tctggcttcc ctaagaaaca atggaagaga aggagcttgg atgaggaaac
     tgttcagcaa 4021 gaggaagggc ttctcacact ttcatgtgct tgtggatcac ctgaggatcc
     tgtgaaaata 4081 cagatactga ttcagtgggt ctgcgtagag cctgagactg ccattctaac
     atgttcccag 4141 gggatgctga tgctgctggc cctgggactg cactgcatgc atgtgaagcc
     ctataggtct
```

```
-continued
4201 cagcagaggc ccatggagag ggaatgtgtg gctctggctg cccagggccc
     aactcggttc 4261 acacggatcg tgctgctccc tggccagcct ttggccacag caccaccagc
     tgctgttgct 4321 gagagagctt cttctctgtg acatgttggc tttcatcagc caccctggga
     agcggaaagt 4381 agctgccact atctttgttt ccccacctca ggcctcacac tttcccatga
     aaagggtgaa 4441 tgtatataac ctgagccctc tccattcaga gttgttctcc catctctgag
     caatgggatg 4501 ttctgttccg cttttatgat atccatcaca tcttatcttg atctttgctc
     ccagtggatt 4561 gtacagtgat gacttttaag ccccacggcc ctgaaataaa atccttccaa
     gggcattgga 4621 agctcactcc acctgaacca tggcttttca tgcttccaag tgtcagggcc
     ttgcccagat 4681 agacagggct ggctctgctg ccccaacctt tcaaggagga aaccagacac
     ctgagacagg 4741 agcctgtatg cagcccagtg cagccttgca gaggacaagg ctggaggcat
     ttgtcatcac 4801 tacagatatg caactaaaat agacgtggag caagagaaat gcattcccac
     cgaggccgct 4861 tttttaggcc tagttgaaag tcaagaagga cagcagcaag cataggctca
     ggattaaaga 4921 aaaaaatctg ctcacagtct gttctggagg tcacatcacc aacaaagctc
     acgccctatg 4981 cagttctgag aaggtggagg caccaggctc aaaagaggaa atttagaatt
     tctcattggg 5041 agagtaaggt accccatcc cagaatgata actgcacagt ggcagaacaa
     actccaccct 5101 aatgtgggtg gaccccgtcc agtctgttga aggcctgaat gtaacaaaag
     ggcttattct 5161 tcctcaagta aggggaact cctgctttgg gctgggacat aagtttttct
     gctttcagac 5221 gcaaactgaa aaatggctct tcttgggtct tgagcttgct ggcatatgga
     ctgaaagaaa 5281 ctatgctatt ggatctcctg gatctccagc ttgctgactg cagatcttga
     gatatgtcag 5341 cctctacagt cacaagagct aattcattct aataaaccaa tctttctgta aaaaa
```

Human CD307e Isoform 2 Precursor Protein (SEQ ID NO: 36).

The signal sequence is underlined. The extracellular domain present in mature protein in shown in bold.

```
  1 mllwvillvl apvsgqfart prpiiflqpp wttvfqgerv
    tltckgfrfy spqktkwyhr 61 ylgkeilret pdnilevqes geyrcqaqgs plsspvhldf
    ssaslilqap lsvfegdsvv 121 lrcrakaevt lnntiykndn vlaflnkrtd fhiphaclkd
    ngayrctgyk esccpvssnt 181 vkiqvqepft rpvlrassfq pisgnpvtlt cetqlslers
    dvplrfrffr ddqtlglgws 241 lspnfqitam wskdsgfywc kaatmpysvi sdsprswiqv
    qipashpvlt lspekalnfe 301 gtkvtlhcet qedslrtlyr fyhegvplrh ksvrcergas
    isfslttens gnyyctadng 361 lgakpskavs lsvtvpvshp vlnlsspedl ifegakvtlh
    ceaqrgslpi lyqfhhegaa 421 lerrsansag gvaisfslta ehsgnyycta dngfgpqrsk
    avslsvtvpv shpvltlssa 481 ealtfegatv tlhcevqrgs pqilyqfyhe dmplwssstp
    svgrvsfsfs lteghsgnyy 541 ctadngfgpq rsevvslfvt vpvsrpiltl rvpraqavvg
    dllelhceap rgsppilywf
```

601 yhedvtlgss sapsggeasf nlsltaehsg nysceanngl
    vaqhsdtisl svivpvsrpi 661 ltfrapraqa vvgdllelhc ealrgsspil ywfyhedvtl
    gkisapsggg asfnlsltte 721 hsgiyscead ngleaqrsem vtlkvavpvs rpvltlrapg
    thaavgdlle lhcealrgsp 781 lilyrffhed vtlgnrssps ggaslnlslt aehsgnysce
    adnglgaqrs etvtlyitgl 841 tanrsgpfat gvaggllsia glaagallly cwlsrkagrk
    pasdparsps dsdsqeptyh 901 nvpaweelqp vytneekmwf tqkygsskrk rnmqwpltpg
    isgtrvplss tlklrwrqpr 961 fpdpcswlpq lltdestrls nccfslctpk fplgekqh cDNA Encoding Human CD307e Isoform 2 Precursor Protein (SEQ ID NO: 37).

Sequence encoding the signal sequence is underlined. The sequence encoding the extracellular domain present in mature protein in shown in bold.

```
   1 aattcactaa tgcattctgc tcttttgag agcacagctt ctcagatgtg ctccttggag
  61 ctggtgtgca gtgtcctgac tgtaagatca agtccaaacc tgttttggaa ttgaggaaac
 121 ttctcttttg atctcagccc ttggtggtcc aggtcttcat gctgctgtgg gtgatattac
 181 tggtcctggc tcctgtcagt ggacagtttg caaggacacc caggcccatt attttcctcc
 241 agcctccatg gaccacagtc ttccaaggag agagagtgac cctcacttgc aagggatttc
 301 gcttctactc accacagaaa acaaaatggt accatcggta ccttgggaaa gaaatactaa
 361 gagaaacccc agacaatatc cttgaggttc aggaatctgg agagtacaga tgccaggccc
 421 agggctcccc tctcagtagc cctgtgcact ggattttttc ttcagcttcg ctgatcctgc
 481 aagctccact ttctgtgttt gaaggagact ctgtggttct gaggtgccgg gcaaaggcgg
 541 aagtaacact gaataatact atttacaaga atgataatgt cctggcattc cttaataaaa
 601 gaactgactt ccatattcct catgcatgtc tcaaggacaa tggtgcatat cgctgtactg
 661 gatataagga agttgttgc cctgtttctt ccaatacagt caaaatccaa gtccaagagc
 721 catttacacg tccagtgctg agagccagct ccttccagcc catcagcggg aacccagtga
 781 ccctgacctg tgagacccag ctctctctag agaggtcaga tgtcccgctc cggttccgct
 841 tcttcagaga tgaccagacc ctgggattag gctggagtct ctccccgaat ttccagatta
 901 ctgccatgtg gagtaaagat tcagggttct actggtgtaa ggcagcaaca atgccttaca
 961 gcgtcatatc tgacagcccg agatcctgga tacaggtgca gatccctgca tctcatcctg
1021 tcctcactct cagccctgaa aaggctctga attttgaggg aaccaaggtg acacttcact
1081 gtgaaaccca ggaagattct ctgcgcactt tgtacaggtt ttatcatgag ggtgtccccc
1141 tgaggcacaa gtcagtccgc tgtgaaaggg gagcatccat cagcttctca ctgactacag
1201 agaattcagg gaactactac tgcacagctg acaatggcct tggcgccaag cccagtaagg
1261 ctgtgagcct ctcagtcact gttcccgtgt ctcatcctgt cctcaacctc agctctcctg
1321 aggacctgat ttttgaggga gccaaggtga cacttcactg tgaagcccag agaggttcac
1381 tccccatcct gtaccagttt catcatgagg gtgctgccct ggagcgtagg tcggccaact
1441 ctgcaggagg agtggccatc agcttctctc tgactgcaga gcattcaggg aactactact
1501 gcacagctga caatggcttt ggcccccagc gcagtaaggc ggtgagcctc tccgtcactg
1561 tccctgtgtc tcatcctgtc ctcaccctca gctctgctga ggccctgact tttgaaggag
1621 ccactgtgac acttcactgt gaagtccaga gaggttcccc acaaatccta taccagtttt
1681 atcatgagga catgcccctg tggagcagct caacaccctc tgtgggaaga gtgtccttca
1741 gcttctctct gactgaagga cattcaggga attactactg cacagctgac aatggctttg
1801 gtccccagcg cagtgaagtg gtgagccttt tgtcactgt tccagtgtct cgccccatcc
1861 tcaccctcag ggttcccagg gcccaggctg tggtggggga cctgctggag cttcactgtg
```

-continued

```
1921 aggccccgag aggctctccc ccaatcctgt actggtttta tcatgaggat gtcaccctgg
1981 ggagcagctc agcccctct ggaggagaag cttctttcaa cctctctctg actgcagaac
2041 attctggaaa ctactcatgt gaggccaaca atggcctagt ggcccagcac agtgacacaa
2101 tatcactcag tgttatagtt ccagtatctc gtcccatcct caccttcagg gctcccaggg
2161 cccaggctgt ggtgggggac ctgctggagc ttcactgtga ggccctgaga ggctcctccc
2221 caatcctgta ctggttttat catgaagatg tcaccctggg taagatctca gccccctctg
2281 gaggaggggc ctccttcaac ctctctctga ctacagaaca ttctggaatc tactcctgtg
2341 aggcagacaa tggtctggag gcccagcgca gtgagatggt gacactgaaa gttgcagttc
2401 cggtgtctcg cccggtcctc accctcaggg ctcccgggac ccatgctgcg gtgggggacc
2461 tgctggagct tcactgtgag gccctgagag gctctcccct gatcctgtac cggttttttc
2521 atgaggatgt caccctagga aataggtcgt cccctctgg aggagcgtcc ttaaacctct
2581 ctctgactgc agagcactct ggaaactact cctgtgaggc cgacaatggc ctcggggccc
2641 agcgcagtga gacagtgaca ctttatatca cagggctgac cgcgaacaga gtggcccttt
2701 ttgccacagg agtcgccggg ggcctgctca gcatagcagg ccttgctgcg ggggcactgc
2761 tgctctactg ctggctctcg agaaaagcag ggagaaagcc tgcctctgac cccgccagga
2821 gcccttcaga ctcggactcc caagagccca cctatcacaa tgtaccagcc tgggaagagc
2881 tgcaaccagt gtacactaat gaggagaaaa tgtggtttac tcagaagtac ggatcatcca
2941 agagaaaaag aaacatgcag tggcctctga ccccaggcat ctcaggaaca agggttcccc
3001 tatcatctac tctgaagtta aggtggcgtc aaccccggtt tccggatccc tgttcttggc
3061 ttcctcagct cctcacagat gagtccacac gtctctccaa ctgctgtttc agcctctgca
3121 ccccaaagtt cccttgggg gagaagcagc attgaagtgg gaagatttag gctgcccag
3181 accatatcta ctggcctttg tttcacatgt cctcattctc agtctgacca gaatgcaggg
3241 ccctgctgga ctgtcacctg tttcccagtt aaagccctga ctggcaggtt ttttaatcca
3301 gtggcaaggt gctcccactc cagggcccag cacatctcct ggattcctta gtgggcttca
3361 gctgtggttg ctgttctgag tactgctctc atcacacccc cacagagggg gtcttaccac
3421 acaaagggag agtgggcctt caggagatgc cgggctggcc taacagctca ggtgctccta
3481 aactccgaca cagagttcct gctttgggtg gatgcatttc tcaattgtca tcagcctggt
3541 ggggctactg cagtgtgctg ccaaatggga cagcacacag cctgtgcaca tgggacatgt
3601 gatgggtctc cccacgggg ctgcatttca cactcctcca cctgtctcaa actctaaggt
3661 cggcacttga caccaaggta acttctctcc tgctcatgtg tcagtgtcta cctgcccaag
3721 taagtggctt tcatacacca agtcccaagt tcttcccatc ctaacagaag taacccagca
3781 agtcaaggcc aggaggacca ggggtgcaga cagaacacat actggaacac aggaggtgct
3841 caattactat ttgactgact gactgaatga atgaatgaat gaggaagaaa actgtgggta
3901 atcaaactgg cataaaatcc agtgcactcc ctaggaaatc cggaggtat tctggcttcc
3961 ctaagaaaca atgaagaga aggagcttgg atgaggaaac tgttcagcaa gaggaagggc
4021 ttctcacact ttcatgtgct tgtggatcac ctgaggatcc tgtgaaaata cagatactga
4081 ttcagtgggt ctgcgtagag cctgagactg ccattctaac atgttcccag ggatgctga
4141 tgctgctggc cctgggactg cactgcatgc atgtgaagcc ctataggtct cagcagaggc
4201 ccatggagag ggaatgtgtg gctctggctg cccagggccc aactcggttc acacggatcg
4261 tgctgctccc tggccagcct ttggccacag caccaccagc tgctgttgct gagagagctt
```

```
-continued
4321 cttctctgtg acatgttggc tttcatcagc caccctggga agcggaaagt agctgccact 4381 atctttgttt ccccacctca ggcctcacac tttcccatga aaagggtgaa tgtatataac 4441 ctgagccctc tccattcaga gttgttctcc catctctgag caatgggatg ttctgttccg 4501 cttttatgat atccatcaca tcttatcttg atctttgctc ccagtggatt gtacagtgat 4561 gacttttaag ccccacggcc ctgaaataaa atccttccaa gggcattgga agctcactcc 4621 acctgaacca tggcttttca tgcttccaag tgtcagggcc ttgcccagat agacagggct 4681 ggctctgctg ccccaacctt tcaaggagga aaccagacag ctgagacagg agcctgtatg 4741 cagcccagtg cagccttgca gaggacaagg ctggaggcat ttgtcatcac tacagatatg 4801 caactaaaat agacgtggag caagagaaat gcattcccac cgaggccgct tttttaggcc 4861 tagttgaaag tcaagaagga cagcagcaag cataggctca ggattaaaga aaaaaatctg 4921 ctcacagtct gttctggagg tcacatcacc aacaaagctc acgccctatg cagttctgag 4981 aaggtggagg caccaggctc aaaagaggaa atttagaatt tctcattggg agagtaaggt 5041 accccatcc cagaatgata actgcacagt ggcagaacaa actccaccct aatgtgggtg 5101 gaccccgtcc agtctgttga aggcctgaat gtaacaaaag ggcttattct tcctcaagta 5161 aggggaact cctgctttgg gctgggacat aagttttct gctttcagac gcaaactgaa 5221 aaatggctct tcttgggtct tgagcttgct ggcatatgga ctgaaagaaa ctatgctatt 5281 ggatctcctg gatctccagc ttgctgactg cagatcttga gatatgtcag cctctacagt 5341 cacaagagct aattcattct aataaaccaa tctttctgta
```

Transmembrane Domains

In some embodiments of any of the CARs described herein, the transmembrane domain is or comprises the transmembrane domain of CD28, CD3 epsilon, CD4, CD5, CD6, CD8a, CD9, CD16, CD22, CD33, CD37, CD45, CD64, CD80, CD86, CD134, CD137, GITR, NGFR, or CD154. Additional examples of suitable transmembrane domains are known in the art.

In some embodiments, the transmembrane domain is a single-pass transmembrane domain. In some embodiments, the transmembrane domain forms an alpha-helix. In some embodiments, the transmembrane domain forms a beta barrel. In some embodiments, the transmembrane domain is about 15 amino acids to about 200 amino acids, about 15 amino acids to about 180 amino acids, about 15 amino acids to about 160 amino acids, about 15 amino acids to about 140 amino acids, about 15 amino acids to about 120 amino acids, about 15 amino acids to about 100 amino acids, about 15 amino acids to about 80 amino acids, about 15 amino acids to about 60 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 22 amino acids, about 15 amino acids to about 20 amino acids, about 15 amino acids to about 18 amino acids, about 18 amino acids to about 200 amino acids, about 18 amino acids to about 180 amino acids, about 18 amino acids to about 160 amino acids, about 18 amino acids to about 140 amino acids, about 18 amino acids to about 120 amino acids, about 18 amino acids to about 100 amino acids, about 18 amino acids to about 80 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 22 amino acids, about 18 amino acids to about 20 amino acids, about 20 amino acids to about 200 amino acids, about 20 amino acids to about 180 amino acids, about 20 amino acids to about 160 amino acids, about 20 amino acids to about 140 amino acids, about 20 amino acids to about 120 amino acids, about 20 amino acids to about 100 amino acids, about 20 amino acids to about 80 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 22 amino acids, about 22 amino acids to about 200 amino acids, about 22 amino acids to about 180 amino acids, about 22 amino acids to about 160 amino acids, about 22 amino acids to about 140 amino acids, about 22 amino acids to about 120 amino acids, about 22 amino acids to about 100 amino acids, about 22 amino acids to about 80 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 25 amino acids to about 200 amino acids, about 25 amino acids to about 180 amino acids, about 25 amino acids to about 160 amino acids, about 25 amino acids to about 140 amino acids, about 25 amino acids to about 120 amino acids, about 25 amino acids to about 100 amino acids, about 25 amino acids to about 80 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 200 amino acids, about 30 amino acids to about 180 amino acids, about 30 amino acids to about 160 amino acids, about 30 amino acids to about 140 amino acids, about 30 amino acids to about 120 amino acids, about 30 amino acids to about 100 amino acids, about 30 amino acids to about 80 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 200 amino acids, about 35 amino acids to about 180 amino acids, about 35 amino acids to about 160 amino acids, about 35 amino acids to about 140 amino acids, about 35 amino acids to about 120 amino acids, about 35 amino acids to about 100 amino acids, about 35 amino acids to about 80 amino acids, about 35 amino acids to about 60 amino acids, about 35 amino acids to about 50 amino acids, about 35 amino acids to about 45 amino acids, about 35 amino acids to about 40 amino acids, about 40 amino acids to about 200 amino acids, about 40 amino acids to about 180 amino acids, about 40 amino acids to about 160 amino acids, about 40 amino acids to about 140 amino acids, about 40 amino acids to about 120 amino acids, about 40 amino acids to about 100 amino acids, about 40 amino acids to about 80 amino acids, about 40 amino acids to about 60 amino acids, about 40 amino acids to about 50 amino acids, about 40 amino acids to about 45 amino acids, about 45 amino acids to about 200 amino acids, about 45 amino acids to about 180 amino acids, about 45 amino acids to about 160 amino acids, about 45 amino acids to about 140 amino acids, about 45 amino acids to about 120 amino acids, about 45 amino acids to about 100 amino acids, about 45 amino acids to about 80 amino acids, about 45 amino acids to about 60 amino acids, about 45 amino acids to about 50 amino acids, about 50 amino acids to about 200 amino acids, about 50 amino acids to about 180 amino acids, about 50 amino acids to about 160 amino acids, about 50 amino acids to about 140 amino acids, about 50 amino acids to about 120 amino acids, about 50 amino acids to about 100 amino acids, about 50 amino acids to about 80 amino acids, about 50 amino acids to about 60 amino acids, about 60 amino acids to about 200 amino acids, about 60 amino acids to about 180 amino acids, about 60 amino acids to about 160 amino acids, about 60 amino acids to about 140 amino acids, about 60 amino acids to about 120 amino acids, about 60 amino acids to about 100 amino acids, about 60 amino acids to about 80 amino acids, about 80 amino acids to about 200 amino acids, about 80 amino acids to about 180 amino acids, about 80 amino acids to about 160 amino acids, about 80 amino acids to about 140 amino acids, about 80 amino acids to about 120 amino acids, about 80 amino acids to about 100 amino acids, about 100 amino acids to about 200 amino acids, about 100 amino acids to about 180 amino acids, about 100 amino acids to about 160 amino acids, about 100 amino acids to about 140 amino acids, about 100 amino acids to about 120 amino acids, about 120 amino acids to about 200 amino acids, about 120 amino acids to about 180 amino acids, about 120 amino acids to about 160 amino acids, about 120 amino acids to about 140 amino acids, about 140 amino acids to about 200 amino acids, about 140 amino acids to about 180 amino acids, about 140 amino acids to about 160 amino acids, about 160 amino acids to about 200 amino acids, about 160 amino acids to about 180 amino acids, or about 180 amino acids to about 200 amino acids.

In some embodiments, the transmembrane domain is or comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, or at least 99% identical) to the transmembrane domain of CD28, CD3 epsilon, CD4, CD5, CD6, CD8a, CD9, CD16, CD22, CD33, CD37, CD45, CD64, CD80, CD86, CD134, 4-1BB, or CD154. In some embodiments, the transmembrane domain is or comprises a sequence that identical to the transmembrane domain of CD28, CD3 epsilon, CD4, CD5, CD6, CD8a, CD9, CD16, CD22, CD33, CD37, CD45, CD64, CD80, CD86, CD134, 4-1BB, or CD154, except that the sequence includes one, two, three, four, or five substitutions. In some embodiments, the transmembrane domain is or comprises a sequence that is identical to the transmembrane domain of CD28, CD3 epsilon, CD4, CD5, CD6, CD8a, CD9, CD16, CD22, CD33, CD37, CD45, CD64, CD80, CD86, CD134, 4-1BB, or CD154, except that is has one, two, three, four, or five amino acids deleted from its N-terminus and/or has one, two, three, four, or five amino acids deleted from its C-terminus. Exemplary sequences for the transmembrane domain of CD28, CD3 epsilon, CD4, CD5, CD6, CD8a, CD9, CD16, CD22, CD33, CD37, CD45, CD64, CD80, CD86, CD134, 4-1BB, and CD154 are shown below. Exemplary nucleic acids sequences encoding a transmembrane domain of CD28, CD3 epsilon, CD4, CD5, CD6, CD8a, CD9, CD16, CD22, CD33, CD37, CD45, CD64, CD80, CD86, CD134, 4-1BB, and CD154 are shown below.

```
Human CD28 Transmembrane Domain
                              (SEQ ID NO: 38)
fwvlvvvggvlacysllvtvafiifwv cDNA Encoding Human CD28 Transmembrane Domain
                              (SEQ ID NO: 39)
ttttgggtgctggtggtggttggtggagtcctggcttgctatagcttgct agtaacagtggcctttattattttctgggtg Human CD3 Epsilon Transmembrane Domain
                              (SEQ ID NO: 40)
vmsvativivdicitgglllllvyyws cDNA Encoding Human CD3 Epsilon Transmembrane
Domain
                              (SEQ ID NO: 41)
gtgatgtcggtggccacaattgtcatagtggacatctgcatcactgggg gcttgctgctgctggtttactactggagc Human CD4 Transmembrane Domain
                              (SEQ ID NO: 42)
malivlggvaglllfiglgiff cDNA Encoding Human CD4 Transmembrane Domain
                              (SEQ ID NO: 43)
atggccctgattgtgctgggggcgtcgccggcctcctgcttttcattgg gctaggcatcttcttc Human CD5 Transmembrane Domain
                              (SEQ ID NO: 44)
aglaagtvasiilalvllvvllvvcgplay cDNA Encoding Human CD5 Transmembrane Domain
                              (SEQ ID NO: 45)
gcaggcctggccgcaggcacggtggcaagcatcatcctggccctggtgc ggtggtgctgctggtcgtgtgcggcccccttgcctac
tcct
```

-continued

Human CD6 Transmembrane Domain
(SEQ ID NO: 46)
ipsivlgilllgslifiafil cDNA Encoding Human CD6 Transmembrane Domain
(SEQ ID NO: 47)
atccccctccatcgttctgggaattctcctccttggctccctcatcttcat agccttcatcctc Human CD8a Transmembrane Domain
(SEQ ID NO: 48)
iyiwaplagtcgvlllslvit cDNA Encoding Human CD8a Transmembrane Domain
Isoform 1
(SEQ ID NO: 49)
atctacatctgggcgcccttggccgggacttgtggggtccttctcctgt cactggttatcacc Human CD9 Transmembrane Domain Isoform 1
(SEQ ID NO: 50)
LLFGFNFIFWLAGIAVLAIGL cDNA Encoding Human CD9 Transmembrane Domain
(SEQ ID NO: 51)
CTGCTGTTCGGATTTAACTTCATCTTCTGGCTTGCCGGGATTGCTGTC

CTTGCCATTGGACTA

Human CD9 Transmembrane Domain Isoform 2
(SEQ ID NO: 52)
FYTGVYILIGAGALMMLVGFL cDNA Encoding Human CD9 Transmembrane Domain
Isoform 2
(SEQ ID NO: 53)
TTCTACACAGGAGTCTATATTCTGATCGGAGCCGGCGCCCTCATGAT

GCTGGTGGGCTTCCTG

Human CD9 Transmembrane Domain Isoform 3
(SEQ ID NO: 54)
MLGLFFGFLLVIFAIEIAAAIWGY cDNA Encoding Human CD9 Transmembrane Domain
Isoform 3
(SEQ ID NO: 55)
ATGCTGGGACTGTTCTTCGGCTTCCTCTTGGTGATATTCGCCATTGA

AATAGCTGCGGCCATCTGGGGATAT

Human CD9 Transmembrane Domain Isoform 4
(SEQ ID NO: 56)
IGAVGIGIAVVMIFGMIFSMILCCAI cDNA Encoding Human CD9 Transmembrane Domain
Isoform 4
(SEQ ID NO: 57)
ATCGGCGCAGTGGGCATCGGCATTGCCGTGGTCATGATATTTGGCAT

GATCTTCAGTATGATCTTGTGCTGTGCTATC

Human CD16 Transmembrane Domain
(SEQ ID NO: 58)
VSFCLVMVLLFAVDTGLYFSV

Human CD22 Transmembrane Domain
(SEQ ID NO: 59)
VAVGLGSCLAILILAICGL

Human CD33 Transmembrane Domain
(SEQ ID NO: 60)
GAIGGAGVTALLALCLCLIFFIV

Human CD37 Transmembrane Domain Isoform 1
(SEQ ID NO: 61)
VLAISGIFTMGIALL cDNA Encoding Human CD37 Transmembrane Domain
Isoform 1
(SEQ ID NO: 62)
GTCCTGGCCATCTCAGGAATCTTCACCATGGGCATCGCCCTCCTG Human CD37 Transmembrane Domain Isoform 2
(SEQ ID NO: 63)
LLGLYFGMLLLLFATQITLGILISTQ cDNA Encoding Human CD37 Transmembrane Domain
Isoform 2
(SEQ ID NO: 64)
CTCCTGGGCCTGTATTTTGGGATGCTGCTGCTCCTGTTTGCCACA

CAGATCACCCTGGGAATCCTCATCTCCACTCAG

Human CD37 Transmembrane Domain Isoform 3
(SEQ ID NO: 65)
LISIVGICLGVGLLELGFMTLSIFL cDNA Encoding Human CD37 Transmembrane Domain
Isoform 3
(SEQ ID NO: 66)
CTTATTTCCATAGTGGGCATTTGCCTGGGCGTCGGCCTACTCGAG

CTCGGGTTCATGACGCTCTCGATATTCCTG

Human CD37 Transmembrane Domain Isoform 4
(SEQ ID NO: 67)
FNLFFFVLGSLIFCFGIWILI cDNA Encoding Human CD37 Transmembrane Domain
Isoform 4
(SEQ ID NO: 68)
TTCAACCTCTTCTTCTTCGTCCTCGGCAGCCTGATCTTCTGCTTCGG

CATCTGGATCCTCATT

Human CD64 Transmembrane Domain
(SEQ ID NO: 69)
VLFYLAVGIMFLVNTVLWVTI cDNA Encoding Human CD64 Transmembrane Domain
(SEQ ID NO: 70)
GTCCTTTTCTATCTGGCAGTGGGAATAATGTTTTTAGTGAACACTGT

TCTCTGGGTGACAATA

Human CD80 Transmembrane Domain
(SEQ ID NO: 71)
LLPSWAITLISVNGIFVICCL cDNA Encoding Human CD80 Transmembrane Domain
(SEQ ID NO: 72)
CTGCTCCCATCCTGGGCCATTACCTTAATCTCAGTAAATGGAATTT

TTGTGATATGCTGCCTG

Human CD86 Transmembrane Domain
(SEQ ID NO: 73)
WITAVLPTVIICVMVFCLILW

Human CD134 Transmembrane Domain
(SEQ ID NO: 74)
VAAILGLGLVLGLLGPLAILL cDNA Encoding Human CD134 Transmembrane Domain
(SEQ ID NO: 75)
GTTGCCGCCATCCTGGGCCTGGGCCTGGTGCTGGGGCTGCTGGGCC

CCCTGGCCATCCTGCTG

Human 4-1BB Transmembrane Domain
(SEQ ID NO: 76)
IISFFLALTSTALLFLLFFLTLRFSVV cDNA Encoding Human 4-1BB Transmembrane Domain (SEQ ID NO: 77)
ATCATCTCCTTCTTTCTTGCGCTGACGTCGACTGCGTTGCTCTTCCTG

CTGTTCTTCCTCACGCTCCGTTTCTCTGTTGTT

Human CD154 Transmembrane Domain (SEQ ID NO: 78)
ifmylltvflitqmigsalfavyl cDNA Encoding Human CD154 Transmembrane Domain (SEQ ID NO: 79)
atttttatgtatttacttactgtttttcttatcacccagatgattgggt cagcactttttgctgtgtatctt In some embodiments of any of the CARs described herein, the transmembrane domain is or comprises the transmembrane domain of CD28 or the transmembrane domain of CD8a. In some embodiments of any of the CARs described herein, the transmembrane domain can include the transmembrane domain of any protein that has a transmembrane domain.

Hinge Sequences

In some embodiments, the linker between the first antigen-binding domain and the second antigen-binding domain can be 1 amino acid to about 250 amino acids (or any of the subranges of this range described herein). For example, a hinge sequence can include a portion of a transmembrane protein that is extracellular, but proximal to a transmembrane domain, and which does not specifically bind to a ligand or soluble protein. Non-limiting examples of a hinge sequence include an extracellular portion of human CD8a, an extracellular portion of human IgG4, or an extracellular portion of CD28.

In some embodiments, the hinge sequence is or includes the hinge of human CD28. An exemplary sequence of the hinge of CD28 is IEVMYPPPYLDNEKSNGTII HVKGKHLCPS PLFPGPSKP (SEQ ID NO: 80) or a fragment thereof (e.g., shortened by 1, 2, 3, 4, 5, 6, 7, 8, 9, 10, 11, 12, 13, 14, or 15 amino acids from its N-terminus and/or shortened by 1, 2, 3, 4, 5, 6, 7, 8, 9, 10, 11, 12, 13, 14, or 15 amino acids from its C-terminus). In some embodiments, the hinge sequence can be at least 80% (e.g., at least 82%, at least 84%, at least 86%, at least 88%, at least 90%, at least 92%, at least 94%, at least 96%, at least 98%, or at least 99%) identical to the sequence of the hinge of human CD28. In some embodiments, the hinge sequence is or include the hinge of human CD8a. An exemplary sequence of the hinge of human CD8a is:

TTTPAPRPPTPAPTIASQPLSLRPEACR-
PAAGGAVHTRGLDFACD (SEQ ID NO: 81) or a fragment thereof (e.g., shortened by 1, 2, 3, 4, 5, 6, 7, 8, 9, or 10 amino acids from its N-terminus and/or shortened by 1, 2, 3, 4, 5, 6, 7, 8, 9, or 10 amino acids from its C-terminus). In some embodiments, the hinge sequence can be at least 80% (e.g., at least 82%, at least 84%, at least 86%, at least 88%, at least 90%, at least 92%, at least 94%, at least 96%, at least 98%, or at least 99%) identical to the sequence of the hinge of human CD8a.

In some embodiments, the hinge of human CD8a is encoded by the sequence of:

(SEQ ID NO: 82)
ACCACGACGCCAGCGCCGCGACCACCAACACCGGCGCCCACCATCGC

GTCGCAGCCCCTGTCCCTGCGCCCAGAGGCGTGCCGGCCAGCGGCGGG

GGGCGCAGTGCACACGAGGGGGCTG GACTTCGCCTGTGAT.

In some embodiments, the hinge sequence is or include the hinge of human IgG4. An exemplary sequence of the hinge of human IgG4 is:

ESKYGPPCPPCPAPEFLGGPSVFLFPPKPKDTLMIS-
RTPEVTCVVVDVSQED PEVQFNWYVDGV-
EVHNAKTKPREEQFNSTYRVVSVLTVLHQDW-
LNGKE YKCKVSNKGLPSSIEKTISKAKGQPREP-
QVYTLPPSQEEMTKNQVSLTCLV KGFYPSDIA-
VEWESNGQPENNYKTTPPVLDSDGSFFLY-
SRLTVDKSRWQE GNVFSCSVMHEALHN-
HYTQKSLSLSLGKM (SEQ ID NO: 83), or a fragment thereof (e.g., shortened by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids from its N-terminus and/or shortened by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 from its C-terminus). In some embodiments, the hinge sequence can be at least 80% (e.g., at least 82%, at least 84%, at least 86%, at least 88%, at least 90%, at least 92%, at least 94%, at least 96%, at least 98%, or at least 99%) identical to the sequence of the hinge of human IgG4.

In some embodiments, the hinge of human IgG4 is encoded by the sequence of:

(SEQ ID NO: 84)
GAGAGCAAGTACGGCCCTCCCTGCCCCCCTTGCCCTGCCCCCGAGTTCCT

GGGCGGACCCAGCGTGTTCCTGTTCCCCCCCAAGCCCAAGGACACCCTGA

TGATCAGCCGGACCCCCGAGGTGACCTGTGTGGTGGTGGACGTGTCCCAG

GAGGACCCCGAGGTCCAGTTCAACTGGTACGTGGACGGCGTGGAGGTGC

ACAACGCCAAGACCAAGCCCCGGGAGGAGCAGTTCAATAGCACCTACCG

GGTGGTGTCCGTGCTGACCGTGCTGCACCAGGACTGGCTGAACGGCAAG

GAATACAAGTGTAAGGTGTCCAACAAGGGCCTGCCCAGCAGCATCGAGAA

AACCATCAGCAAGGCCAAGGGCCAGCCTCGGGAGCCCCAGGTGTACAC

CCTGCCCCCTAGCCAAGAGGAGATGACCAAGAACCAGGTGTCCCTGACC

TGCCTGGTGAAGGGCTTCTACCCCAGCGACATCGCCGTGGAGTGGGAGA

GCAACGGCCAGCCCGAGAACAACTACAAGACCACCCCCCCTGTGCTGGA

CAGCGACGGCAGCTTCTTCCTGTACAGCCGGCTGACCGTGGACAAGAGCC

```
GGTGGCAGGAGGGCAACGTCTTTAGCTGCTCCGTGATGCACGAGGCCCTG

CACAACCACTACACCCAGAAGAG CCTGAGCCTGTCCCTGGGCAAGATG
```

Intracellular Signaling Domains

In some embodiments, the intracellular signaling domain includes 20 amino acids to about 250 amino acids (or any subrange of this range described herein). In some embodiments of any of the CARs described herein, the intracellular signaling domain is the intracellular signaling domain of human 4-1BB, human CD28, human CD3zeta, human CD5, human CD22, human CD79, human DAP-10, or human DAP-12.

In some embodiments, the intracellular signaling sequence is or includes the intracellular signaling sequence of human CD3 zeta. An exemplary sequence of the human CD3 zeta intracellular signaling sequence is:

RVKFSRSADAPAYQQGQNQLYNELNLGRREEY-DVLDKRRGRDPEMGGK PRRKNPQEGLY-NELQKDKMAEAYSEIGMKGERRRGKGHDG-LYQGLSTA TKDTYDALHMQALPPR (SEQ ID NO: 85) or a fragment thereof (e.g., shortened by 1, 2, 3, 4, 5, 6, 7, 8, 9, 10, 12, 13, 14, 15, 16, 17, 18, 19, 20, 21, 22, 23, 24, 25, 26, 27, 28, 29, or 30 amino acids from its N-terminus and/or shortened by 11, 2, 3, 4, 5, 6, 7, 8, 9, 10, 12, 13, 14, 15, 16, 17, 18, 19, 20, 21, 22, 23, 24, 25, 26, 27, 28, 29, or 30 amino acids from its C-terminus). In some embodiments, the intracellular signaling sequence can be at least 80% (e.g., at least 82%, at least 84%, at least 86%, at least 88%, at least 90%, at least 92%, at least 94%, at least 96%, at least 98%, or at least 99%) identical to the sequence of the intracellular signaling sequence of human CD3 zeta. In some embodiments, the intracellular signaling sequence is at least 50 contiguous amino acids, at least 55 contiguous amino acids, at least 60 contiguous amino acids, at least 65 contiguous amino acids, at least 70 contiguous amino acids, at least 75 contiguous amino acids, at least 80 contiguous amino acids, at least 85 contiguous amino acids, at least 90 contiguous amino acids, at least 95 contiguous amino acids, or at least 100 contiguous amino acids of the intracellular signaling sequence of human CD3 zeta.

In some embodiments, the intracellular signaling sequence is or includes the intracellular signaling sequence of human 4-1BB. An exemplary sequence of the human 4-1BB intracellular signaling sequence is:

KRGRKKLLY-IFKQPFMRPVQTTQEEDGCSCRFPEEEEGGCEL (SEQ ID NO: 86) or a fragment thereof (e.g., shortened by 1, 2, 3, 4, 5, 6, 7, 8, 9, or 10 amino acids from its N-terminus and/or shortened by 1, 2, 3, 4, 5, 6, 7, 8, 9, or 10 amino acids from its C-terminus). In some embodiments, the intracellular signaling sequence can be at least 80% (e.g., at least 82%, at least 84%, at least 86%, at least 88%, at least 90%, at least 92%, at least 94%, at least 96%, at least 98%, or at least 99%) identical to the sequence of the intracellular signaling sequence of human 4-1BB. In some embodiments, the intracellular signaling sequence is at least 10 contiguous amino acids, at least 15 contiguous amino acids, at least 20 contiguous amino acids, at least 25 contiguous amino acids, at least 35 contiguous amino acids, or at least 40 contiguous amino acids of the intracellular signaling sequence of human 4-1BB. In some embodiments, a human 4-1BB intracellular signaling sequence is encoded by:

```
                                    (SEQ ID NO: 87)
AAACGGGGCAGAAAGAAACTCCTGTATATATTCAAACAACCATTTATG

AGACCAGTACAAACTACTCAAGAGGAAGATGGCTGTAGCTGCCGATTT

CCAGAAGAAGAAGAAGGAGGATGT GAACTG.
```

In some embodiments, the intracellular signaling sequence is or includes the intracellular signaling sequence of human CD28. An exemplary sequence of the human CD28 intracellular signaling sequence is:

RSKRSRLLHSDYMNMTPRRPGPTRKHYQPYAP-PRDFAAYRS (SEQ ID NO: 88) or a fragment thereof (e.g., shortened by 1, 2, 3, 4, 5, 6, 7, 8, 9, or 10 amino acids from its N-terminus and/or shortened by 1, 2, 3, 4, 5, 6, 7, 8, 9, or 10 amino acids from its C-terminus). In some embodiments, the intracellular signaling sequence can be at least 80% (e.g., at least 82%, at least 84%, at least 86%, at least 88%, at least 90%, at least 92%, at least 94%, at least 96%, at least 98%, or at least 99%) identical to the sequence of the intracellular signaling sequence of human CD28. In some embodiments, the intracellular signaling sequence is at least 10 contiguous amino acids, at least 15 contiguous amino acids, at least 20 contiguous amino acids, at least 25 contiguous amino acids, or at least 35 contiguous amino acids of the intracellular signaling sequence of human CD28.

In some embodiments, the intracellular signaling sequence is or includes the intracellular signaling sequence of human CD5. An exemplary sequence of the human CD5 intracellular signaling sequence is:

KKLVKKFRQKKQRQWIGPTGMNQNMSFHRNHT-ATVRSHAENPTASHVD NEYSQPPRNSHLSAYPA-LEGALHRSSMQPDNSSDSDYDLHGAQRL (SEQ ID NO: 89) or a fragment thereof (e.g., shortened by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acids from its N-terminus and/or shortened by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acids from its C-terminus). In some embodiments, the intracellular signaling sequence can be at least 80% (e.g., at least 82%, at least 84%, at least 86%, at least 88%, at least 90%, at least 92%, at least 94%, at least 96%, at least 98%, or at least 99%) identical to the sequence of the intracellular signaling sequence of human CD5. In some embodiments, the intracellular signaling sequence is at least 10 contiguous amino acids, at least 15 contiguous amino acids, at least 20 contiguous amino acids, at least 25 contiguous amino acids, or at least 35 contiguous amino acids, at least 40 contiguous amino acids, at least 45 contiguous amino acids, at least 50 contiguous amino acids, at least 55 contiguous amino acids, at least 60 contiguous amino acids, at least 65 contiguous amino acids, at least 70 contiguous amino acids, at least 75 contiguous amino acids, at least 80 contiguous amino acids, at least 85 contiguous amino acids, or at least 90 contiguous amino acids of the intracellular signaling sequence of human CD28.

In some embodiments, the intracellular signaling sequence is or includes the intracellular signaling sequence of human CD22. An exemplary sequence of the human CD22 intracellular signaling sequence is:

KLQRRWKRTQSQQGLQENSSGQSFFVRNKKVR-RAPLSEGPHSLGCYNPM MEDGISYTTLRFPEM-NIPRTGDAESSEMQRPPPDCDDTVTYSALH-KRQVG DYENVIPDFPEDEGIHYSELIQFGVGER-PQAQENVDYVILKH (SEQ ID NO: 90) or a fragment thereof (e.g., shortened by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids from its N-terminus and/or shortened by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids from its C-terminus). In some embodiments, the intracellular signaling sequence can be at least 80% (e.g., at least 82%, at least 84%, at least 86%, at least 88%, at least 90%, at least 92%, at least 94%, at least 96%, at least 98%, or at least 99%) identical to the sequence of the intracellular signaling sequence of human CD22. In some embodiments, the intracellular signaling sequence is at least 10 contiguous amino acids, at least 15 contiguous amino acids, at least 20 contiguous amino acids, at least 25 contiguous amino acids, or at least 35 contiguous amino acids, at least 40 contiguous amino acids, at least 45 contiguous amino acids, at least 50 contiguous amino acids, at least 55 contiguous amino acids, at least 60 contiguous amino acids, at least 65 contiguous amino acids, at least 70 contiguous amino acids, at least 75 contiguous amino acids, at least 80 contiguous amino acids, at least 85 contiguous amino acids, at least 90 contiguous amino acids, at least 95 contiguous amino acids, at least 100 contiguous amino acids, at least 105 contiguous amino acids, at least 110 contiguous amino acids, at least 115 contiguous amino acids, at least 120 contiguous amino acids, at least 125 contiguous amino acids, at least 130 contiguous amino acids, or at least 135 contiguous amino acids of the intracellular signaling sequence of human CD22.

In some embodiments, the intracellular signaling sequence is or includes the intracellular signaling sequence of human CD79. An exemplary sequence of the human CD79 intracellular signaling sequence is:

RKRWQNEKLGLDAGDEYEDENLYEGLNL-DDCSMYEDISRGLQGTYQDV GSLNIGDVQLEKP (SEQ ID NO: 91) or a fragment thereof (e.g., shortened by 1, 2, 3, 4, 5, 6, 7, 8, 9, 10, 11, 12, 13, 14, 15, 16, 17, 18, 19, or 20 amino acids from its N-terminus and/or shortened by 1, 2, 3, 4, 5, 6, 7, 8, 9, 10, 11, 12, 13, 14, 15, 16, 17, 18, 19, or 20 amino acids from its C-terminus). In some embodiments, the intracellular signaling sequence can be at least 80% (e.g., at least 82%, at least 84%, at least 86%, at least 88%, at least 90%, at least 92%, at least 94%, at least 96%, at least 98%, or at least 99%) identical to the sequence of the intracellular signaling sequence of human CD79. In some embodiments, the intracellular signaling sequence is at least 10 contiguous amino acids, at least 15 contiguous amino acids, at least 20 contiguous amino acids, at least 25 contiguous amino acids, or at least 35 contiguous amino acids, at least 40 contiguous amino acids, at least 45 contiguous amino acids, at least 50 contiguous amino acids, or at least 55 contiguous amino acids of the intracellular signaling sequence of human CD79.

Additional aspects and examples of intracellular signaling sequences are known in the art.

Co-Stimulatory Domains

In some embodiments, a co-stimulatory domain can include a sequence of 20 amino acids to 250 amino acids (or any subranges of this range described herein).

In some embodiments of any of the CARs described herein, the co-stimulatory domain is the co-stimulatory domain of 4-1BB, CD28, CD2, CD4, CD27, CD8, or CD137.

In some embodiments, the costimulatory domain is or includes the costimulatory domain of human 4-1BB. An exemplary sequence of the human 4-1BB costimulatory domain is:

KRGRKKLLYIFKQPFMRPVQTTQEEDGCSCRFP-EEEEGGCEL (SEQ ID NO: 92) or a fragment thereof (e.g., shortened by 1, 2, 3, 4, 5, 6, 7, 8, 9, or 10 amino acids from its N-terminus and/or shortened by 1, 2, 3, 4, 5, 6, 7, 8, 9, or 10 amino acids from its C-terminus). In some embodiments, the costimulatory domain can be at least 80% (e.g., at least 82%, at least 84%, at least 86%, at least 88%, at least 90%, at least 92%, at least 94%, at least 96%, at least 98%, or at least 99%) identical to the sequence of the co-stimulatory domain of human 4-1BB. In some embodiments, the co-stimulatory domain is at least 10 contiguous amino acids, at least 15 contiguous amino acids, at least 20 contiguous amino acids, at least 25 contiguous amino acids, at least 30 contiguous amino acids, or at least 35 contiguous amino acids of the co-stimulatory domain of human 4-1BB.

In some embodiments, the costimulatory domain is or includes the costimulatory domain of human CD28. An exemplary sequence of the human 4-1BB costimulatory domain is:

RSKRSRLLHSDYMNMTPRRPGPTRKHYQPYAPPRD-FAAYRS (SEQ ID NO: 93) or a fragment thereof (e.g., shortened by 1, 2, 3, 4, 5, 6, 7, 8, 9, or 10 amino acids from its N-terminus and/or shortened by 1, 2, 3, 4, 5, 6, 7, 8, 9, or 10 amino acids from its C-terminus). In some embodiments, the costimulatory domain can be at least 80% (e.g., at least 82%, at least 84%, at least 86%, at least 88%, at least 90%, at least 92%, at least 94%, at least 96%, at least 98%, or at least 99%) identical to the sequence of the co-stimulatory domain of human CD28. In some embodiments, the co-stimulatory domain is at least 10 contiguous amino acids, at least 15 contiguous amino acids, at least 20 contiguous amino acids, at least 25 contiguous amino acids, at least 30 contiguous amino acids, or at least 35 contiguous amino acids of the co-stimulatory domain of human CD28.

In some embodiments, the costimulatory domain is or includes the costimulatory domain of human CD4. An exemplary sequence of the human CD4 costimulatory domain is:

CVRCRHRRRQAERMSQIKRLLSEKKTCQCPHRFQ-KTCSPI (SEQ ID NO: 94) or a fragment thereof (e.g., shortened by 1, 2, 3, 4, 5, 6, 7, 8, 9, or 10 amino acids from its N-terminus and/or shortened by 1, 2, 3, 4, 5, 6, 7, 8, 9, or 10 amino acids from its C-terminus). In some embodiments, the costimulatory domain can be at least 80% (e.g., at least 82%, at least 84%, at least 86%, at least 88%, at least 90%, at least 92%, at least 94%, at least 96%, at least 98%, or at least 99%) identical to the sequence of the co-stimulatory domain of human CD4. In some embodiments, the co-stimulatory domain is at least 10 contiguous amino acids, at least 15 contiguous amino acids, at least 20 contiguous amino acids, at least 25 contiguous amino acids, at least 30 contiguous amino acids, or at least 35 contiguous amino acids of the co-stimulatory domain of human CD4.

In some embodiments, the costimulatory domain is or includes the costimulatory domain of human CD27. An exemplary sequence of the human CD27 costimulatory domain is:
QRRKYRSNKGESPVEPAEPCHYSCPREEEGSTIP-IQEDYRKPEPACSP (SEQ ID NO: 95) or a fragment thereof (e.g., shortened by 1, 2, 3, 4, 5, 6, 7, 8, 9, 10, 11, 12, 13, or 14 amino acids from its N-terminus and/or shortened by 1, 2, 3, 4, 5, 6, 7, 8, 9, 10, 11, 12, 13, or 14 amino acids from its C-terminus). In some embodiments, the costimulatory domain can be at least 80% (e.g., at least 82%, at least 84%, at least 86%, at least 88%, at least 90%, at least 92%, at least 94%, at least 96%, at least 98%, or at least 99%) identical to the sequence of the co-stimulatory domain of human CD27. In some embodiments, the co-stimulatory domain is at least 10 contiguous amino acids, at least 15 contiguous amino acids, at least 20 contiguous amino acids, at least 25 contiguous amino acids, at least 30 contiguous amino acids, at least 35 contiguous amino acids, or at least 40 contiguous amino acids of the co-stimulatory domain of human CD27.

In some embodiments, the costimulatory domain is or includes the costimulatory domain of human CD8. An exemplary sequence of the human CD8 costimulatory domain is: LYCNHRNRRRVCKCPRPVVKSGDKPSL-SARYV (SEQ ID NO: 96) or a fragment thereof (e.g., shortened by 1, 2, 3, 4, or 5 amino acids from its N-terminus and/or shortened by 1, 2, 3, 4, or 5 amino acids from its C-terminus). In some embodiments, the costimulatory domain can be at least 80% (e.g., at least 82%, at least 84%, at least 86%, at least 88%, at least 90%, at least 92%, at least 94%, at least 96%, at least 98%, or at least 99%) identical to the sequence of the co-stimulatory domain of human CD8. In some embodiments, the co-stimulatory domain is at least 10 contiguous amino acids, at least 15 contiguous amino acids, at least 20 contiguous amino acids, at least 25 contiguous amino acids, or at least 30 contiguous amino acids of the co-stimulatory domain of human CD8.

In some embodiments, the costimulatory domain is or includes the costimulatory domain of human CD2. An exemplary sequence of the human CD2 costimulatory domain is:
KRKKQRSRRNDEELETRAHRVATEERGRKPHQI-PASTPQNPATSQHPPPPP GHRSQAPSHRPPPPGHR-VQHQPQKRPPAPSGTQVHQQKGPPLPRPRVQPK PPHGAAENSLSPSSN (SEQ ID NO: 97) or a fragment thereof (e.g., shortened by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 55 amino acids from its N-terminus and/or shortened by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 55 amino acids from its C-terminus). In some embodiments, the costimulatory domain can be at least 80% (e.g., at least 82%, at least 84%, at least 86%, at least 88%, at least 90%, at least 92%, at least 94%, at least 96%, at least 98%, or at least 99%) identical to the sequence of the co-stimulatory domain of human CD2. In some embodiments, the co-stimulatory domain is at least 10 contiguous amino acids, at least 15 contiguous amino acids, at least 20 contiguous amino acids, at least 25 contiguous amino acids, at least 30 contiguous amino acids, at least 35 contiguous amino acids, at least 40 contiguous amino acids, at least 45 contiguous amino acids, at least 50 contiguous amino acids, at least 55 contiguous amino acids, at least 60 contiguous amino acids, at least 65 contiguous amino acids, at least 70 contiguous amino acids, at least 75 contiguous amino acids, at least 80 contiguous amino acids, at least 85 contiguous amino acids, at least 90 contiguous amino acids, at least 95 contiguous amino acids, at least 100 contiguous amino acids, at least 105 contiguous amino acids, or at least 110 contiguous amino acids of the co-stimulatory domain of human CD2.

In some embodiments, the costimulatory domain is or includes the costimulatory domain of human CD137. An exemplary sequence of the human CD137 costimulatory domain is:
KRGRKKLLYIFKQPFMRPVQTTQEEDGCSCRF-PEEEEGGCEL (SEQ ID NO: 98) or a fragment thereof (e.g., shortened by 1, 2, 3, 4, 5, 6, 7, 8, 9, or 10 amino acids from its N-terminus and/or shortened by 1, 2, 3, 4, 5, 6, 7, 8, 9, or 10 amino acids from its C-terminus). In some embodiments, the costimulatory domain can be at least 80% (e.g., at least 82%, at least 84%, at least 86%, at least 88%, at least 90%, at least 92%, at least 94%, at least 96%, at least 98%, or at least 99%) identical to the sequence of the co-stimulatory domain of human CD137. In some embodiments, the co-stimulatory domain is at least 10 contiguous amino acids, at least 15 contiguous amino acids, at least 20 contiguous amino acids, at least 25 contiguous amino acids, at least 30 contiguous amino acids, or at least 35 contiguous amino acids of the co-stimulatory domain of human CD137. An exemplary CD137 co-stimulatory domain is encoded by the nucleic acid sequence of:

```
                                    (SEQ ID NO: 99)
AAACGGGGCAGAAAGAAACTCCTGTATATATTCAAACAACCATTTATG

AGACCAGTACAAACTACTCAAGAGGAAGATGGCTGTAGCTGCCGATTT

CCAG AAGAAGAAGAAGGAGGATGTGAACTG.
```

Additional aspects and examples of costimulatory domains are known in the art.

Method of Generating a Chimeric Antigen Receptor (CAR)-Expressing Cell

Also provided herein are methods of generating a chimeric antigen receptor (CAR)-expressing cell that include introducing into a cell (e.g., any of the cells described herein) any of the nucleic acids encoding any of the CARs described herein or any of the vectors described herein. In some examples, the cell can be a eukaryotic cell. In some examples, the eukaryotic cell can be mammalian cell (e.g., a human cell). In some embodiments of any of the methods described herein, the mammalian cell can be, e.g., a T-cell (CD4+ T-cell, a CD8+ T-cell, a TH1 cell, a TH2 cell, or a Treg cell), a B-cell (e.g., a memory B cell), a NK cell, a neutrophil, a macrophage, or a monocyte. In some embodiments of any of the methods described herein, the mammalian cell is chronic myelogenous leukemia (CML) K-562 cell (ATCCR CCL-243™).

Non-limiting methods for introducing a nucleic acid or vector described herein into a cell are described herein. Additional methods for introducing a nucleic acid or vector into a cell are known in the art.

In some embodiments of any of the methods described herein, the mammalian cell can be a cell obtained from a subject (e.g., a human subject). In some examples, the subject (e.g., a human) has been diagnosed or identified as having a cancer (e.g., a cancer characterized by cancer cells that express one or both of BCMA and CD307e). Some embodiments of any of the methods described herein can further include, before the introducing step, obtaining a cell from a subject (e.g., any of the subjects described herein).

Some embodiments of any of these methods can further include, after the introducing step, a step of culturing the cell in a liquid culture medium (e.g., under conditions that allow the cells to proliferate). Liquid culture media that can be used in the culturing of these cells are known in the art.

Eukaryotic Cells

The methods and compositions described herein can involve the use of, or comprise, eukaryotic cells. Non-limiting examples of eukaryotic cells include mammalian cells (e.g., mouse cells, rat cells, hamster cells, rabbit cells, canine cells, feline cells, monkey cells, or human cells). In some embodiments of any of the methods described herein, the mammalian cell can be, e.g., a T-cell (CD4+ T-cell, a CD8+ T-cell, a TH1 cell, a TH2 cell, or a Treg cell), a B-cell (e.g., a memory B cell), a NK cell, a neutrophil, a macrophage, or a monocyte.

In some examples of any of the cells described herein, the cell can be obtained from a subject (e.g., and optionally, later administered back to the same subject after introduction of a nucleic acid encoding any of the CARs described herein, or any of the vectors described herein). In such embodiments, the subject can be a subject diagnosed or identified as having a cancer (e.g., a cancer characterized by cancer cells that express one or both of BCMA and CD307e).

Methods of culturing mammalian cells are well known in the art. Mammalian cells can be maintained in vitro under conditions that allow for proliferation, differentiation, and/or growth. Briefly, mammalian cells can be cultured by contacting a cell (e.g., any cell) with a cell culture medium that includes the necessary growth factors and supplements to support cell viability and growth.

Methods of introducing nucleic acids and vectors into a cell (e.g., a eukaryotic cell) are known in the art. Non-limiting examples of methods that can be used to introduce a nucleic acid or vector into a cell include lipofection, transfection, electroporation, microinjection, calcium phosphate transfection, dendrimer-based transfection, cationic polymer transfection, cell squeezing, sonoporation, optical transfection, impalection, hydrodynamic delivery, magneto-fection, viral transduction (e.g., adenoviral and lentiviral transduction), and nanoparticle transfection.

Methods of Treatment

Also provided herein are methods of treating a cancer in a subject that include: administering a therapeutically effective amount of any of the cells described herein (e.g., any cells expressing any of the CARs described herein). In some embodiments of any of the methods described herein, the cancer is characterized by cancer cells that express one or both of BCMA and CD307e. In some embodiments of any of the methods described herein, the cancer is a carcinoma, a sarcoma (e.g., Ewing sarcoma, Kaposi sarcoma, osteosarcoma, and soft tissue sarcoma), a myeloma (e.g., multiple myeloma), a leukemia (e.g., a B-cell leukemia, e.g., chronic lymphocytic leukemia (CLL), acute lymphoblastic leukemia, B-cell prolymphocytic leukemia, precursor B lymphoblastic leukemia, and hairy cell leukemia, acute myeloid leukemia (AML), chronic myelogenous leukemia (CML)), or a lymphoma (e.g., a B-cell lymphoma, e.g., small lymphocytic lymphoma, Burkitt lymphoma, cutaneous T-cell lymphoma, Hodgkin's lymphoma, non-Hodgkin's lymphoma, primary central nervous system lymphoma, or T-cell lymphoma). In some embodiments, the cancer is a carcinoma, a sarcoma, a myeloma, a leukemia, or a lymphoma that is characterized by cancer cells that express one or both of BCMA and CD307e. Methods for detecting cancer cell expression of BCMA and CD307e can be performed using methods known in the art (e.g., staining, sorting, or imaging cancer cells from the subject with a labeled antibody that binds to BCMA and a labeled antibody that binds specifically to CD307e).

In some embodiments of any of the methods described herein, the subject has been diagnosed or identified as having the cancer. Some embodiments of the methods described herein further include diagnosing or identifying the subject as having the cancer. Some embodiments of the methods described herein can further include selecting a subject having a cancer for treatment using any of the methods described herein.

In some embodiments of any of the methods described herein, the method further includes, prior to the administering step: obtaining an initial cell from the subject (e.g., any of the exemplary types of mammalian cells described herein); and introducing a nucleic acid (e.g., any of the nucleic acids encoding any of the CARs described herein) or a vector (e.g., any of the vectors described herein) into the initial cell, to yield the cell that is administered to the subject. In some embodiments of any of the methods described herein, the method further includes between the introducing step and the administering step, a step of culturing the cell that is administered to the subject in a liquid culture medium (e.g., under conditions that allow for proliferation).

Also provided herein are methods of treating multiple myeloma in a subject that include: administering to a subject a therapeutically effective amount of any of the cells described herein (e.g., any of the cells expressing any of the CARs described herein) to the subject. In some embodiments of any of the methods described herein, the subject has been diagnosed or identified as having multiple myeloma. In some embodiments, the subject has been identified as having multiple myeloma characterized by cancer cells that express one or both of BCMA and CD307e.

Some embodiments of the methods described herein further include diagnosing or identifying the subject as having multiple myeloma. Some embodiments of the methods described herein can further include selecting a subject having multiple myeloma for treatment using any of the methods described herein.

In some embodiments of any of the methods described herein, the method further includes, prior to the administering step: obtaining an initial cell from the subject having multiple myeloma (e.g., any of the exemplary types of mammalian cells described herein); and introducing a nucleic acid (e.g., any of the nucleic acids encoding any of the CARs described herein) or a vector (e.g., any of the vectors described herein) into the initial cell, to yield the cell that is administered to the subject. In some embodiments of any of the methods described herein, the method further includes between the introducing step and the administering step, a step of culturing the cell that is administered to the subject in a liquid culture medium (e.g., under conditions that allow for proliferation). In any of the methods described herein, the initial cell, as described herein, is not a cancer cell. In some embodiments of any of the methods described herein, the subject is human. The term "subject" refers to any mammal, e.g., a dog, feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject may be a non-human mammal, especially mammals that are conventionally used as models for demonstrating therapeutic efficacy in humans (e.g., murine, lapine, porcine, canine or primate animals) may be employed. For example, the non-human mammal may be an animal cancer model (e.g., an animal cancer model of any of the specific types of cancer described herein).

In some embodiments of any of the methods described herein, the cancer is a solid cancer. In some embodiments of any of the methods described herein, the cancer is a non-metastatic cancer. In some embodiments of any of the methods described herein, the cancer is a metastatic cancer.

Some embodiments of any of the methods described herein further include administering to the subject one or more additional anti-cancer therapies. In some embodiments of any of the methods described herein, the one or more additional anti-cancer therapies is selected from the group consisting of chemotherapy, immunotherapy, surgical resection, and radiation therapy.

In some embodiments of any of the methods described herein, the subject has previously been administered another anti-cancer therapy, and the anti-cancer therapy was unsuccessful.

Compositions and Kits

Also provided herein are compositions (e.g., pharmaceutical compositions) that include at least one of any of the cells described herein (e.g., any of the cells described herein that express a CAR described herein) and a pharmaceutically acceptable carrier. Examples of pharmaceutically acceptable carriers are known in the art and include, e.g., phosphate buffered saline, saline, and Ringer's solution. Also provided herein are compositions that include at least one of any of the cells described herein (e.g., any of the cells described herein that express a CAR described herein) and a cell freezing medium or storage. Examples of cell-freezing medium are known in the art, and can include one or more of, e.g., dimethyl sulfoxide (DMSO), carboxymethylcellulose sodium, and glycerol. Non-limiting examples of storage media can include one or more of, e.g., a buffered isotonic solution, a buffered solution, a culture medium, and serum (e.g., human serum). In some embodiments of these compositions, the compositions described herein are frozen or thawed. In some embodiments of these compositions, the compositions are not frozen.

In some embodiments, the compositions are formulated for intravenous administration. The compositions can be provided in a dosage form that includes a sufficient quantity of the cells effective to treat a disease (e.g., cancer) in a subject.

Also provided are compositions that include any of the nucleic acids encoding any of the CARs described herein, or any of the vectors described herein and, optionally, a pharmaceutically acceptable carrier.

Also provided herein are kits that include any of the compositions (e.g., pharmaceutical compositions) described herein. In some embodiments, the kits can further include instructions for performing any of the methods described herein. In some embodiments, the kits can include at least one dose of any of the compositions described herein. In some embodiments, the kits can further include a cell culture medium useful for propagating the cells. In some embodiments, the kit can further include a sterile containing, wherein the cells are disposed in the sterile container. In some embodiments, the kit can include one or more agents useful for introducing a nucleic acid or a vector in a mammalian cell.

EXAMPLES

The invention is further described in the following examples, which do not limit the scope of the invention described in the claims.

Example 1. Exemplary CARs

Figure 2:
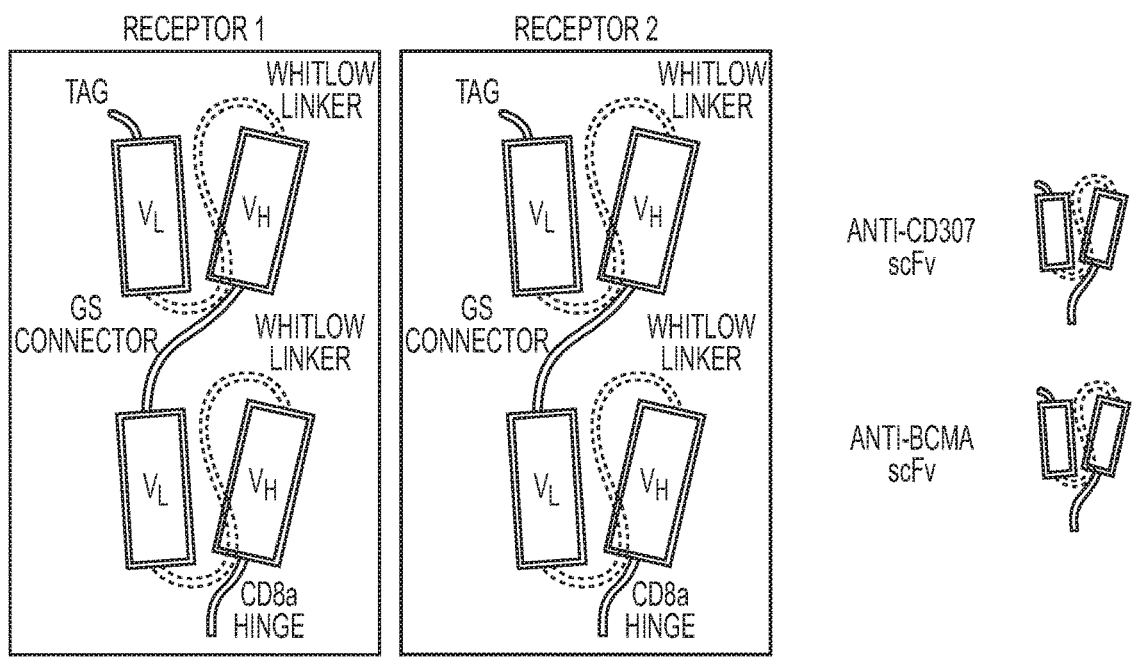
FIG. 2 is a schematic representation of two embodiments of the extracellular portion of a bi-specific CAR.
Figure 3:
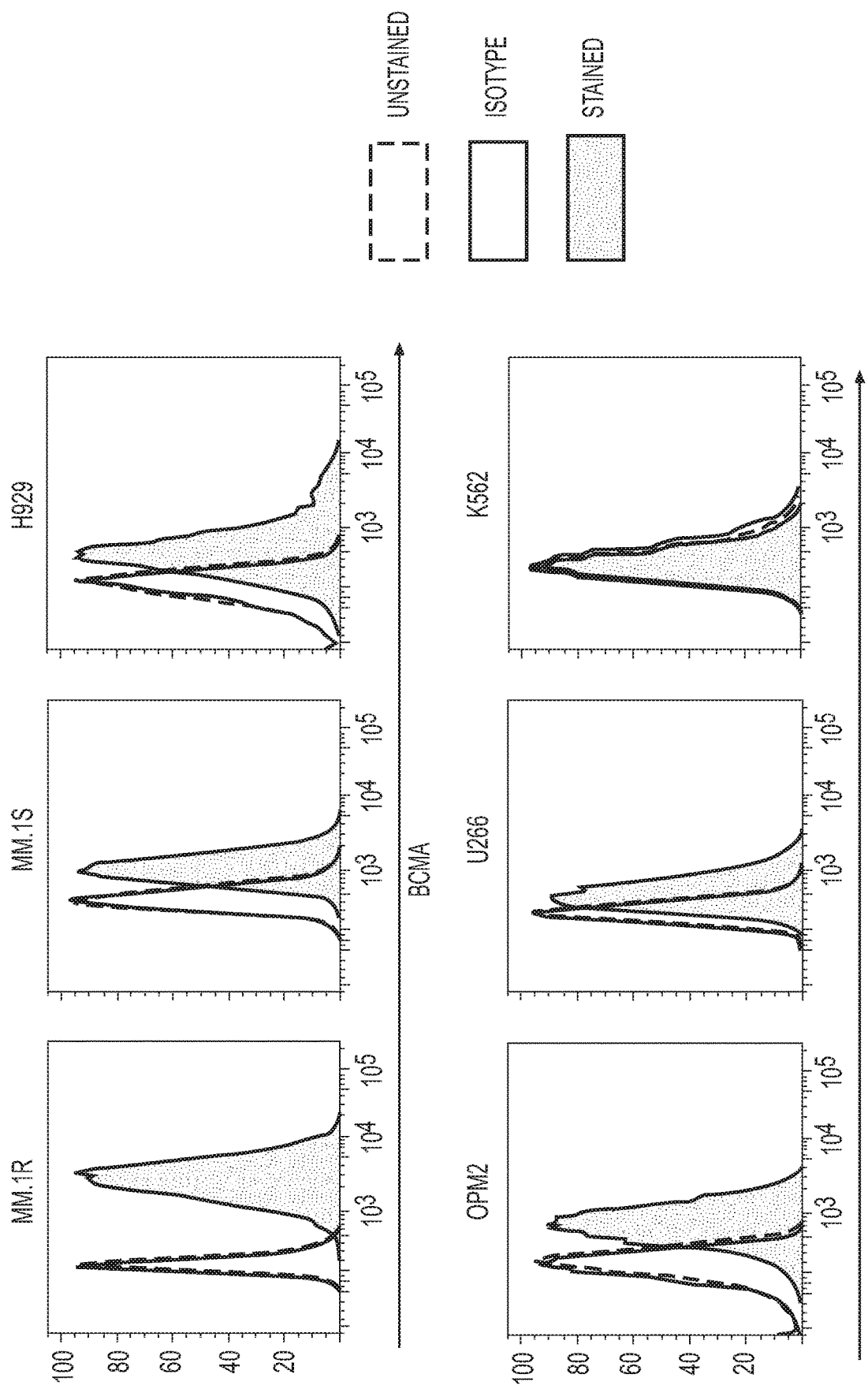
FIG. 3 shows representative FACS histogram plots for BCMA staining on immortalized cancer cell lines derived from patients with multiple myeloma (MM. 1R, MM. 1S, H929, OPM2, U266) and negative control cells (K562), unstained cells, and isotope control.
Figure 4:
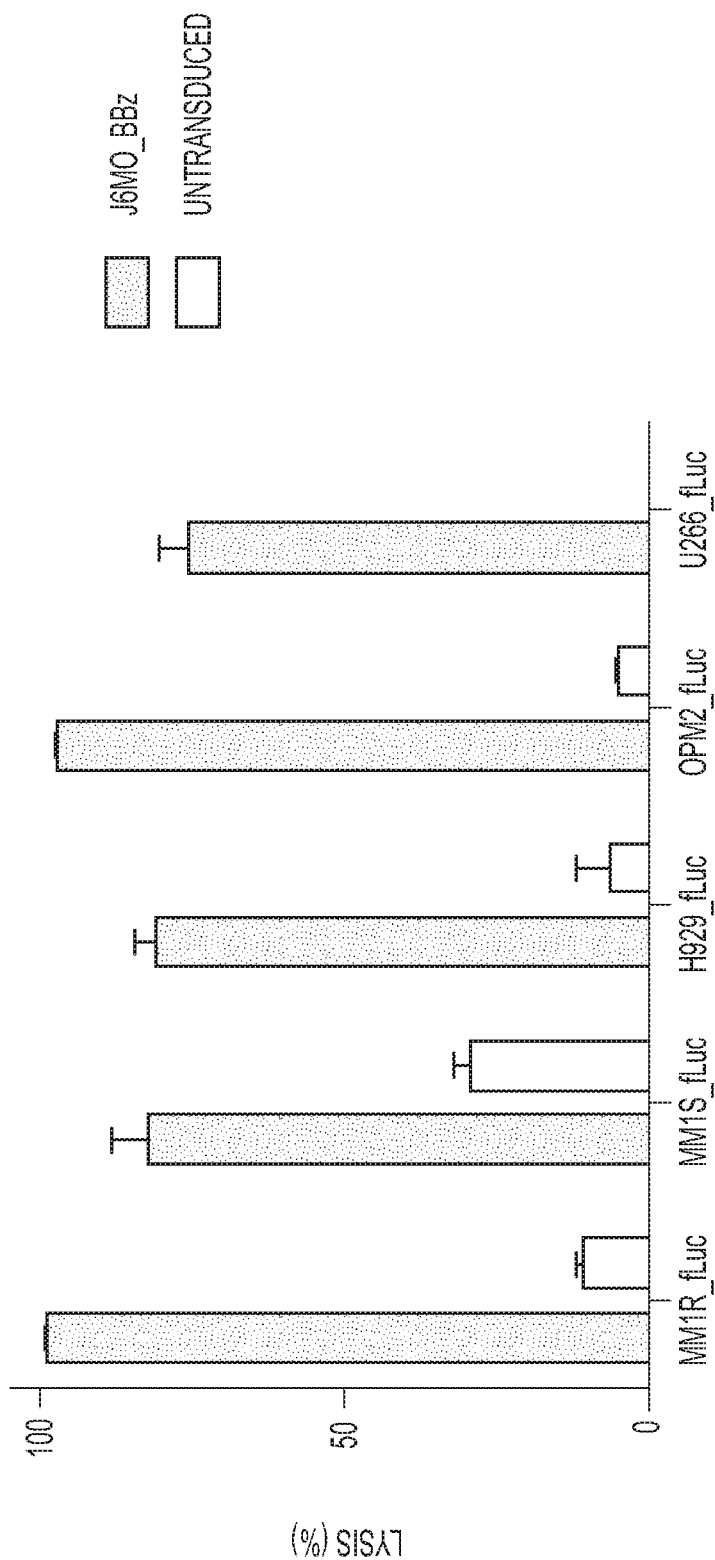
FIG. 4 is a representative graph showing the ability of the J6M0 scFv based CAR (J6M0_BBz) to kill multiple BCMA positive cell lines (MM. 1R, MM.1 S, H929, OPM2, U266), compared to untransduced T cells as a negative control. The effector to target (E:T) ratio used was 1:1.
Figure 5:
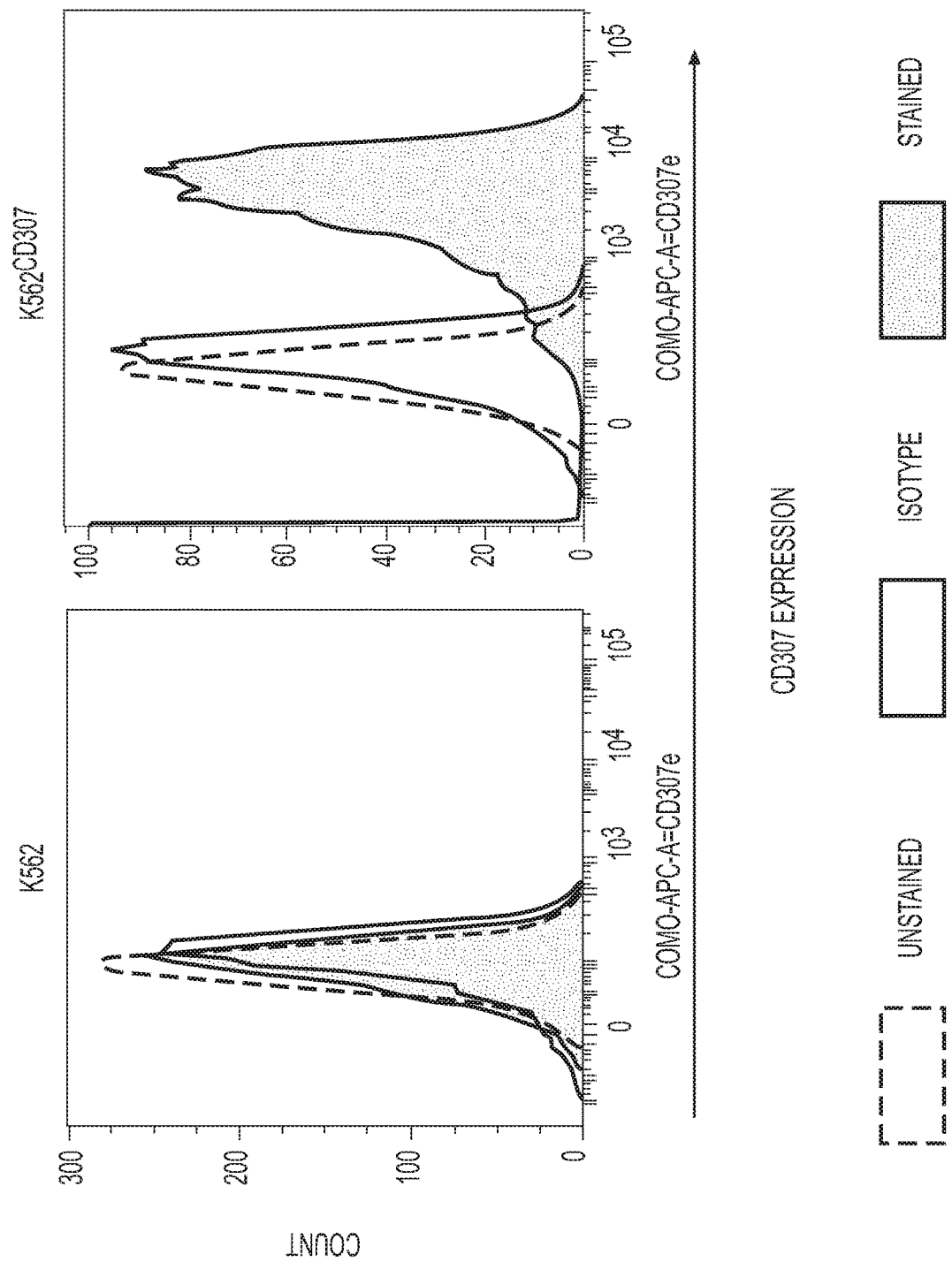
FIG. 5 is a representative FACS histogram plot showing CD307e expression on K562 tumor cells that have been engineered to exogenously express CD307 and the parental negative control K562 cells that do not naturally express CD307, unstained cells, and isotope control.

Without wishing to be bound by theory, the present inventors generated various embodiments of bispecific chimeric antigen receptors (CARs) that can bind specifically to both BCMA and CD307e (FIGS. 1-2 and Table 1). An example of a tandem CAR is provided in FIG. 1. In some embodiments, a bispecific CAR is a single polypeptide chain in which the first antigen-binding domain is a single-chain variable fragments (scFv) that binds to CD307 (10A8) and the second antigen-binding domain is a scFV that binds to BCMA (J6M0), the co-stimulatory binding domain is 4-1BB (CD137), and the intracellular signaling domain is CD3 zeta. In some embodiments of any of the CARs described herein, the first and second antigen-binding domains are linked by a GS connector (FIG. 2). In some embodiments, the first antigen-binding domain includes a light chain variable domain ($V_L$) and a heavy chain variable domain ($V_H$) that are connected via a first scFv linker. In some embodiments, the second antigen-binding domain includes a light chain variable domain (VL) and a heavy chain variable domain (VH). In some embodiments, the VL and VH domain of the second antigen-binding domain are connected via a second scFv linker. In some embodiments, a variable domain (VH or VL) of the first or second antigen-binding domain is linked to a hinge sequence (e.g., a CD8a hinge sequence).

TABLE 1

Summary of Exemplary CARs

| | CAR | | | | |
|---|---|---|---|---|---|
| | J6M0 | m10A8 | 10A8 | 1G7.v85 | 1G7v.93 |
| Antigen | BCMA | CD307 | CD307 | CD307 | CD307 |
| $V_L$ Domain | SEQ ID NO: 1 | SEQ ID NO: 9 | SEQ ID NO: 5 | SEQ ID NO: 13 | SEQ ID NO: 17 |
| Linker | (SEQ ID NO: 100) | | | | |
| $V_H$ Domain | SEQ ID NO: 2 | SEQ ID NO: 10 | SEQ ID NO: 6 | SEQ ID NO: 14 | SEQ ID NO: 18 |
| Hinge | CD8α (SEQ ID NO: 81) | | | | |
| Transmembrane Domain | CD8α (SEQ ID NO: 48) | | | | |
| Co-stimulatory Domain | 4-1BB (SEQ ID NO: 93) | | | | |
| Intracellular-Signaling Domain | CD3ζ (SEQ ID NO: 85) | | | | |

Example 2. Tandem CARs

Multiple myeloma is an incurable plasma cell malignancy. While cell-based CAR therapies produce dramatic remissions, antigen negative escape variants have been detected in some multiple myeloma patients whom relapse. Without wishing to be bound by theory, the present inventors have discovered that targeting two disease-associated antigens may reduce the risk of antigen escape. BCMA and FCRL5 (CD307e) are lineage-specific markers that are highly expressed in multiple myeloma. Table 2 provides a summary of the generated Tandem CARs.

TABLE 2

Summary of Exemplary Tandem CARs

| | Tandem CAR | | | | |
|---|---|---|---|---|---|
| | J6M0/m10A8 (TanCAR1) | J6M0/10A8 (TanCAR2) | 10A8/J6M0 (TanCAR3) | J6M0/ 1G7.v85 Tandem | J6M0/ 1G7v.93 Tandem |
| First $V_L$ Domain | SEQ ID NO: 1 | SEQ ID NO: 1 | SEQ ID NO: 5 | SEQ ID NO: 1 | SEQ ID NO: 1 |
| Linker | | Whitlow Linker (SEQ ID NO: 12) | | | |
| First $V_H$ Domain | SEQ ID NO: 2 | SEQ ID NO: 2 | SEQ ID NO: 6 | SEQ ID NO: 2 | SEQ ID NO: 2 |
| Connector | | $(G_4S)5$ connector (SEQ ID NO: 25) | | | |
| Second $V_L$ Domain | SEQ ID NO: 9 | SEQ ID NO: 5 | SEQ ID NO: 1 | SEQ ID NO: 13 | SEQ ID NO: 17 |
| Linker | | Whitlow Linker (SEQ ID NO: 12) | | | |
| Second $V_H$ Domain | SEQ ID NO: 10 | SEQ ID NO: 6 | SEQ ID NO: 2 | SEQ ID NO: 14 | SEQ ID NO: 18 |
| Hinge | | CD8α (SEQ ID NO: 81) | | | |
| Transmembrane Domain | | CD8α (SEQ ID NO: 48) | | | |
| Co-stimulatory Domain | | 4-1BB (SEQ ID NO: 93) | | | |
| Intracellular-Signaling Domain | | CD3ζ (SEQ ID NO: 85) | | | |

Figure 6:
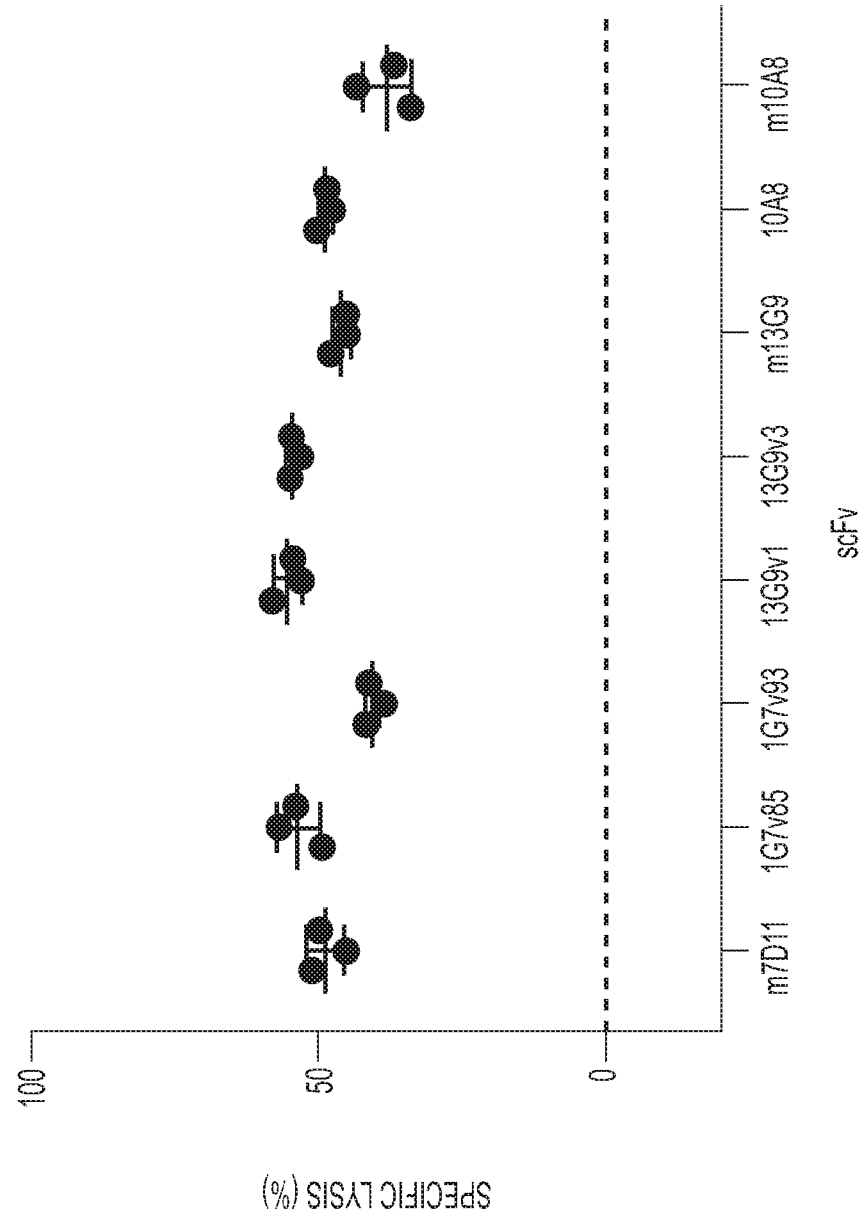
FIG. 6 is a representative scatter plot of targeted cell lysis of K562$^{CD307}$ cells following incubation with m7D11, 1G7v85, 1G7v93, 13G9v1, 13G9v3, m13G9, 10A8, or m10A8.
Figure 7A:
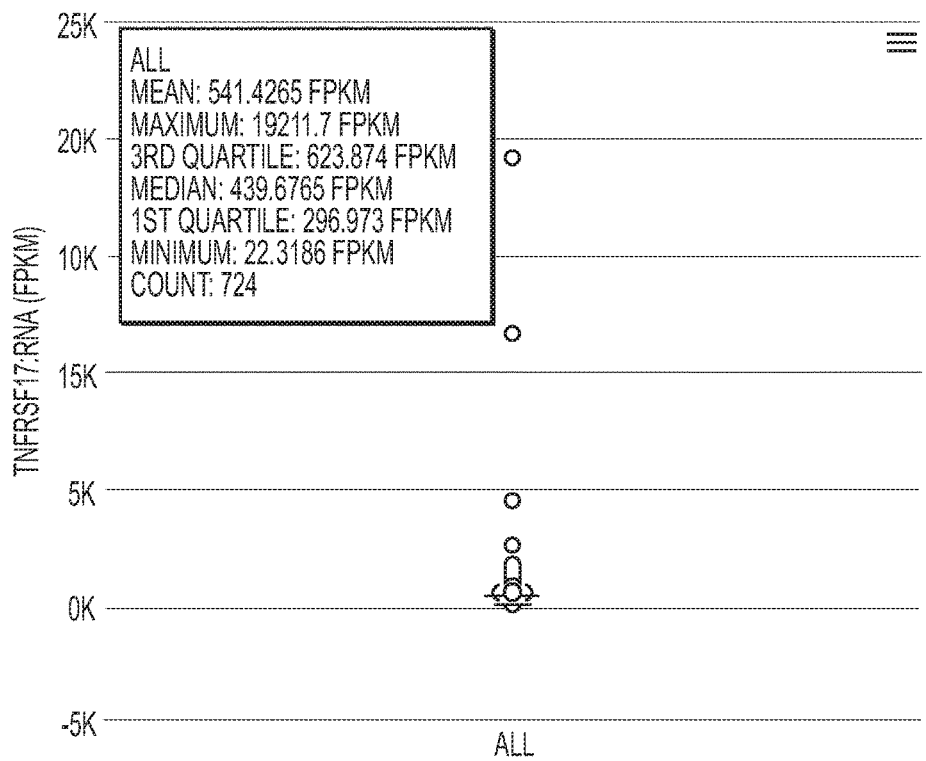
FIG. 7A is a representative plot of fragments per kilobase of transcript per million mapped reads (FPKM) of BCMA obtained from the CoMMpass™ study.
Figure 7B:
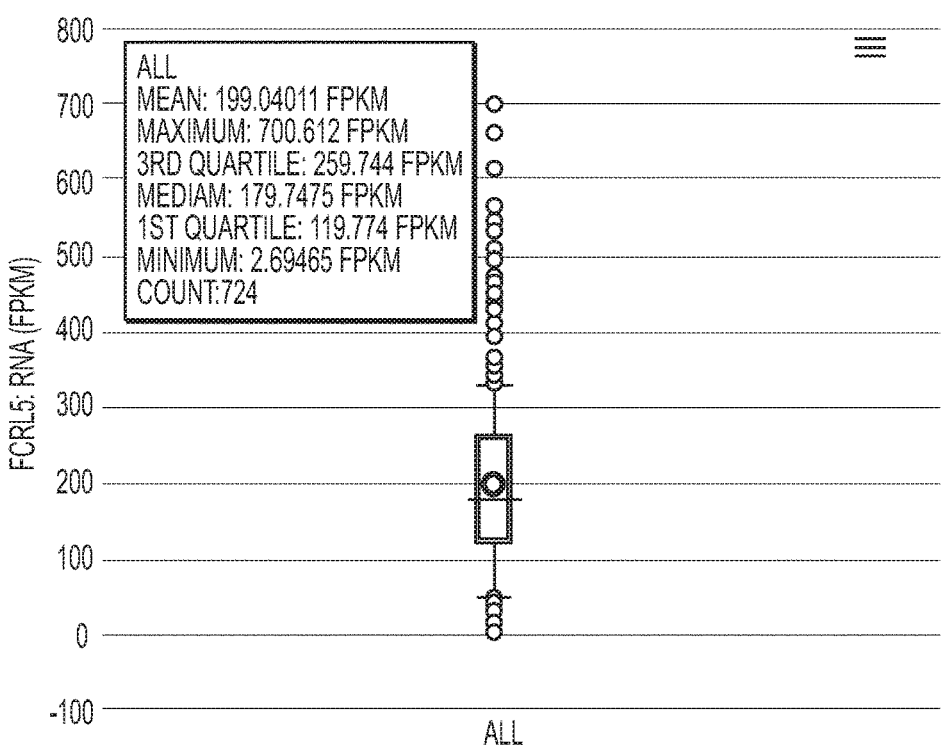
FIG. 7B is a representative plot of FPKM of FCRL5 (CD307e) obtained from the CoMMpass™ study.
Figure 8A:
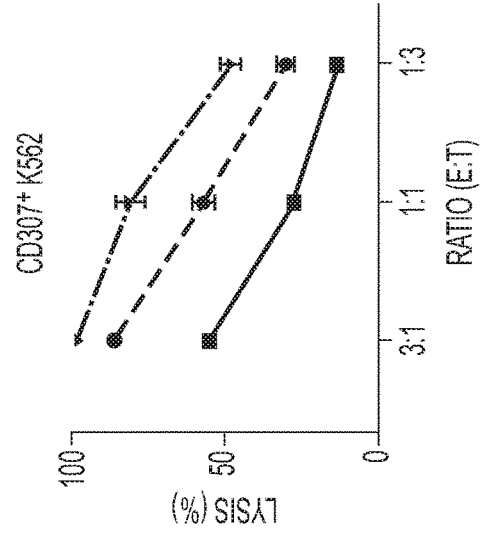
FIG. 8A is a representative graph of CD307 antigen negative K562 tumor cell lysis at effector to target ratios (E:T) of 3:1, 1:1 and 1:3 using a humanized 10A8 scFv, a murine m10A8 scFv (m10A8), or untransduced (UNTR) control T cells.
Figure 8B:
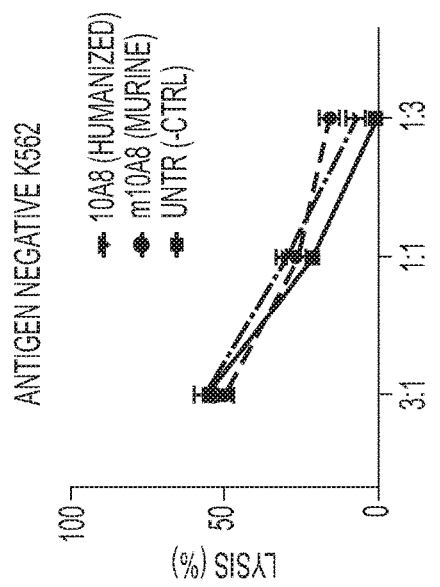
FIG. 8B is a representative graph of CD307$^+$ K562 tumor cell lysis at ratios (E:T) of 3:1, 1:1 and 1:3 using a humanized 10A8 scFv, a murine m10A8 scFv (m10A8), or untransduced (UNTR) control T cells.
Figure 9A:
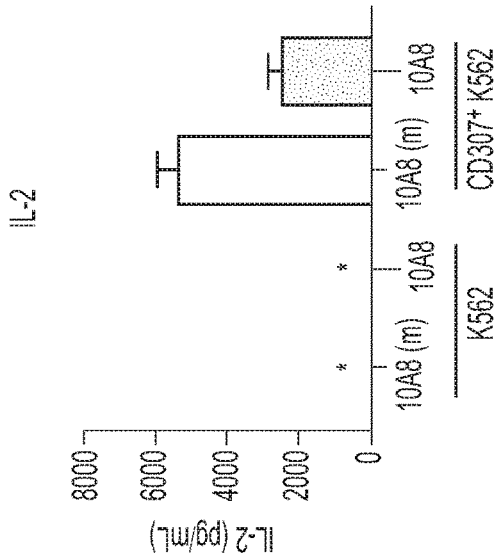
FIG. 9A is a representative graph of IFNγ levels following incubation of CD307 antigen-negative K562 tumor cells and CD307$^+$ K562 tumor cells with murine 10A8 (m10A8) or humanized 10A8 (10A8). * represents undetectable levels.
Figure 9B:
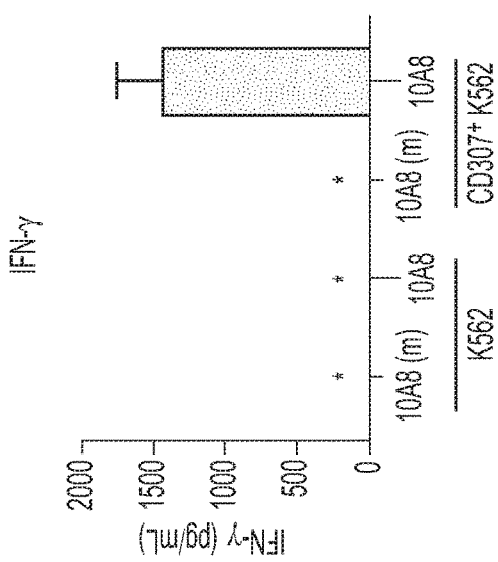
FIG. 9B is a representative graph of IL-2 levels following incubation of antigen negative K562 tumor cells and CD307$^+$ K562 tumor cells with murine 10A8 (m10A8) or humanized 10A8 (10A8). * represents undetectable levels.
Figure 10:
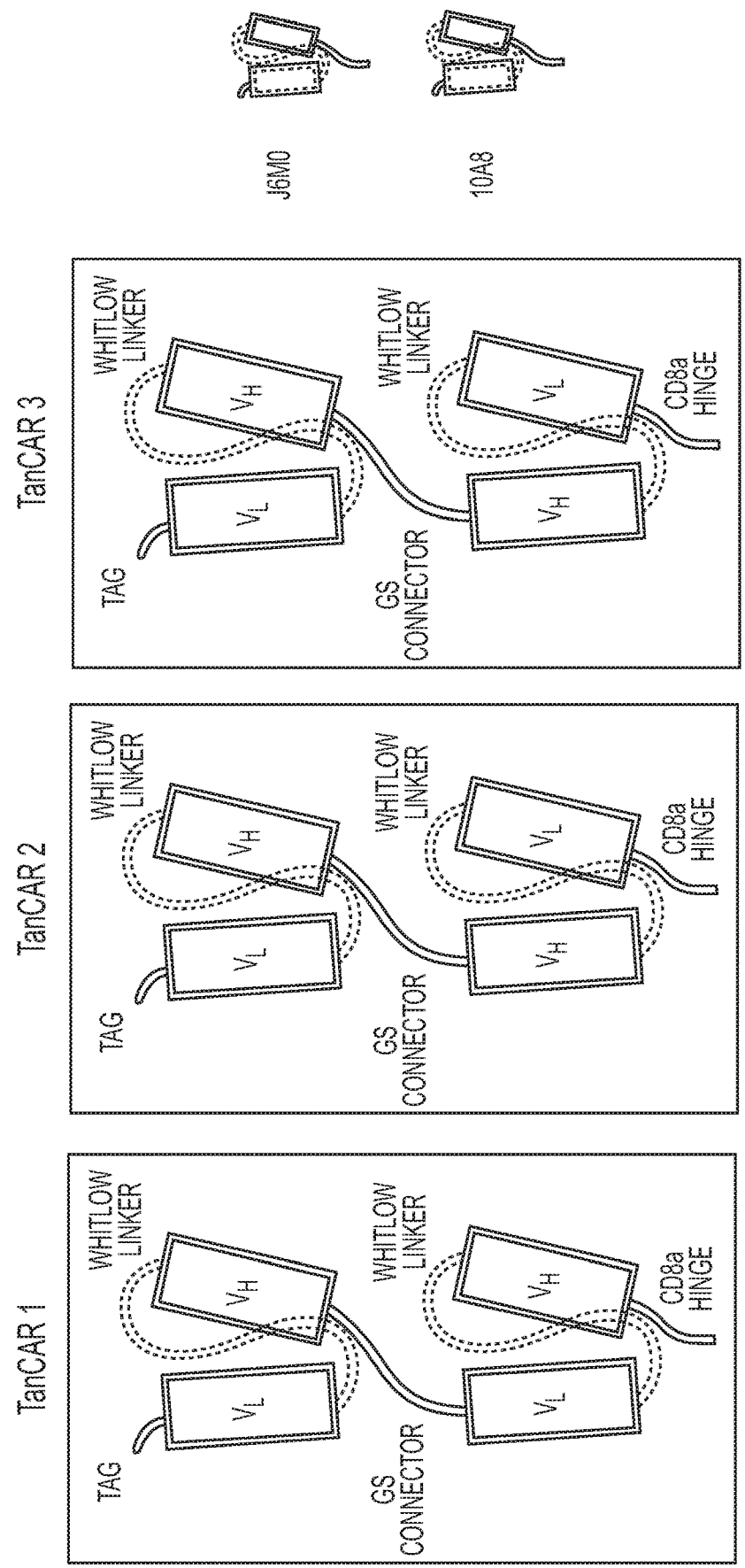
FIG. 10 is a schematic representation of three embodiments of the extracellular portion of a series of tandem CAR including J6M0/10A8 (TanCAR1), J6M0/10A8 (TanCAR2) and 10A8/J6M0 (TanCAR3).
Figure 11:
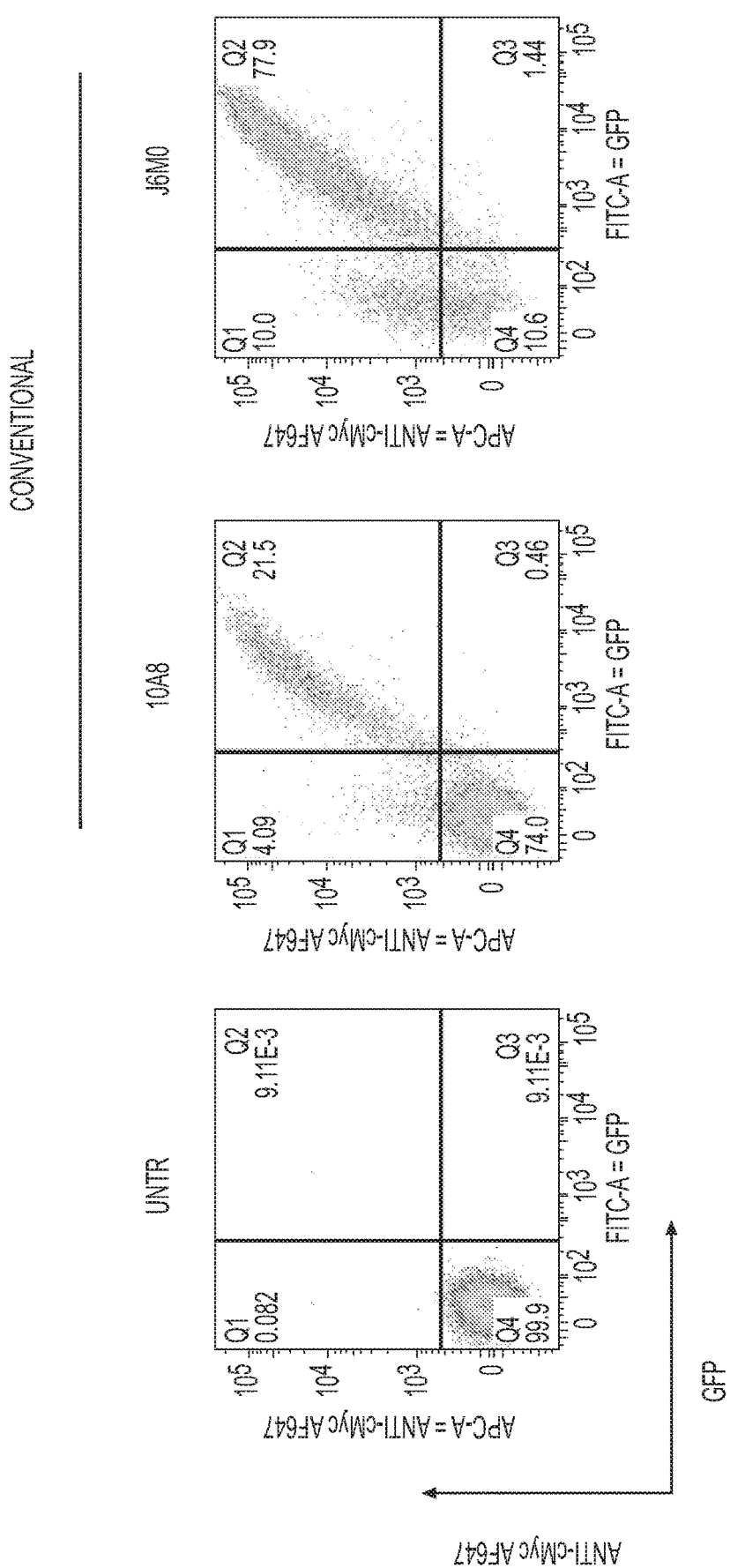
FIG. 11 is representative FACS dot plots of untransduced (UNTR), anti-CD307 (10A8), and anti-BCMA (J6M0) expression in primary human T cells expressing conventional CARs.
Figure 12:
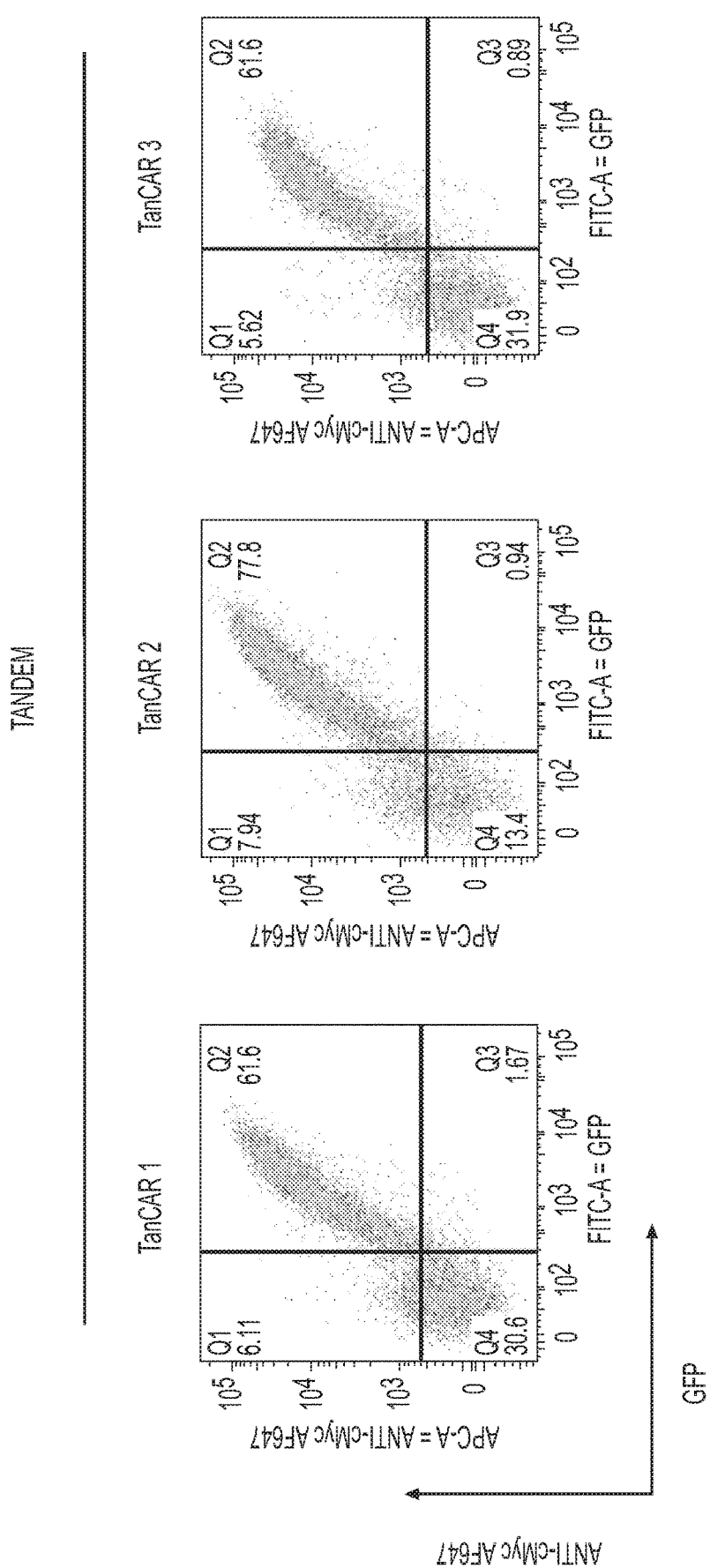
FIG. 12 is representative FACS dot plots of tandem CARs carrying anti-CD307 (10A8) and anti-BCMA (J6M0) scFvs, expressed in primary human T cells.
Figure 13A:
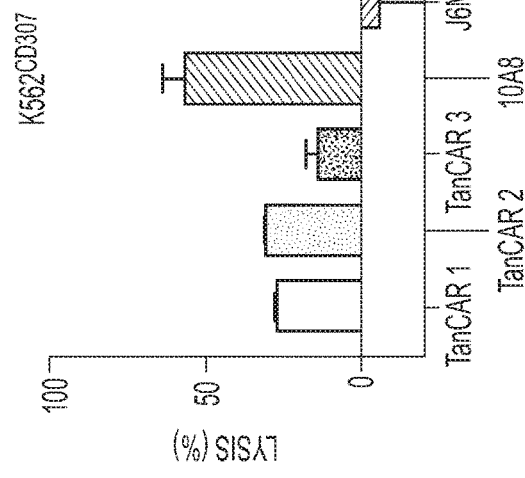
FIG. 13A is a representative graph of antigen negative K562 tumor cell lysis following incubation with TanCAR1, TanCAR2, TanCAR3, 10A8, J6M0, negative control, or untransduced (UNTR) control T cells.
Figure 13B:
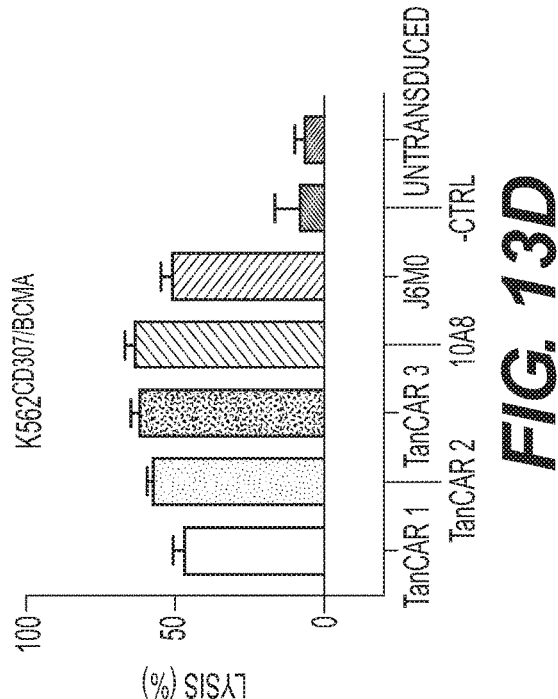
FIG. 13B is a representative graph of K562$^{CD307}$ tumor cell lysis following incubation with TanCAR1, TanCAR2, TanCAR3, 10A8, J6M0, negative control, or untransduced (UNTR) control T cells.
Figure 13C:
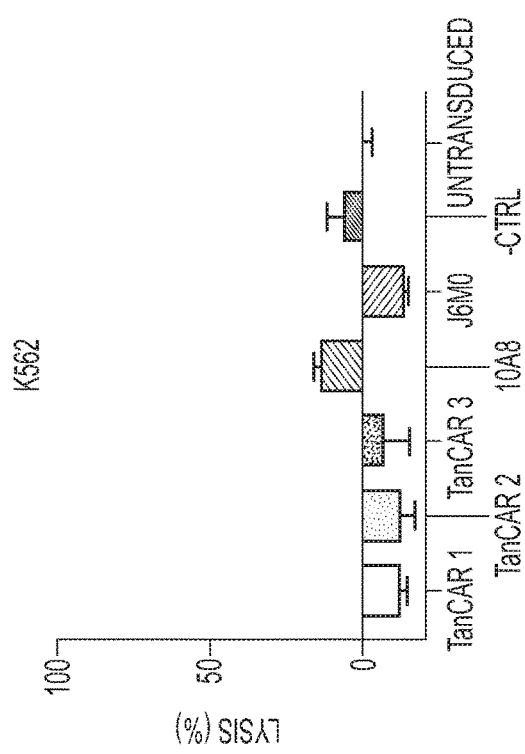
FIG. 13C is a representative graph of K562$^{BCMA}$ tumor cell lysis following incubation with TanCAR1, TanCAR2, TanCAR3, 10A8, J6M0, negative control, or untransduced (UNTR) control T cells.
Figure 13D:
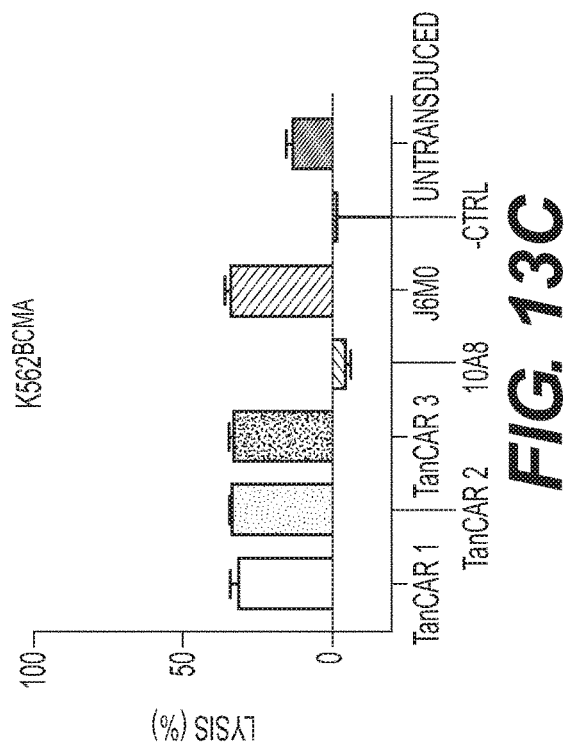
FIG. 13D is a representative graph of K562$^{CD307/BCMA}$ tumor cell lysis following incubation with TanCAR1, TanCAR2, TanCAR3, 10A8, J6M0, negative control, or untransduced (UNTR) control T cells.

As shown in FIGS. 3, 7A-B, and 16, BCMA and CD307 are ubiquitously expressed by patient-derived multiple myeloma tumor cells. FIGS. 6 and 8B show that over 50% of cell lysis was seen in CD307+ K562 cells following incubation with a murine 10A8 scFv CAR and a humanized 10A8 scFv CAR. FIG. 9A showed that high IFNγ levels were detected in CD307+ K562 cells following incubation with human 10A8 scFv CAR, while IFNγ was undetected in antigen-negative K562 cells. FIG. 9B showed that high IL-2 levels were detected in CD307+ K562 cells following incubation with human 10A8 scFv CAR and murine 10A8 scFv CAR, while IL-2 was undetected in antigen-negative K562 cells. FIGS. 13A-D showed cell lysis using 10A8 scFv/ J6M0 scFv bispecific CARs expressing either CD307, BCMA, or both. Expression of conventional (mono-specific) CARs and bispecific CARs against BCMA and CD307 in primary T cells was assessed (FIGS. 11 and 12).

Example 3. Optimization Studies

Figure 14:
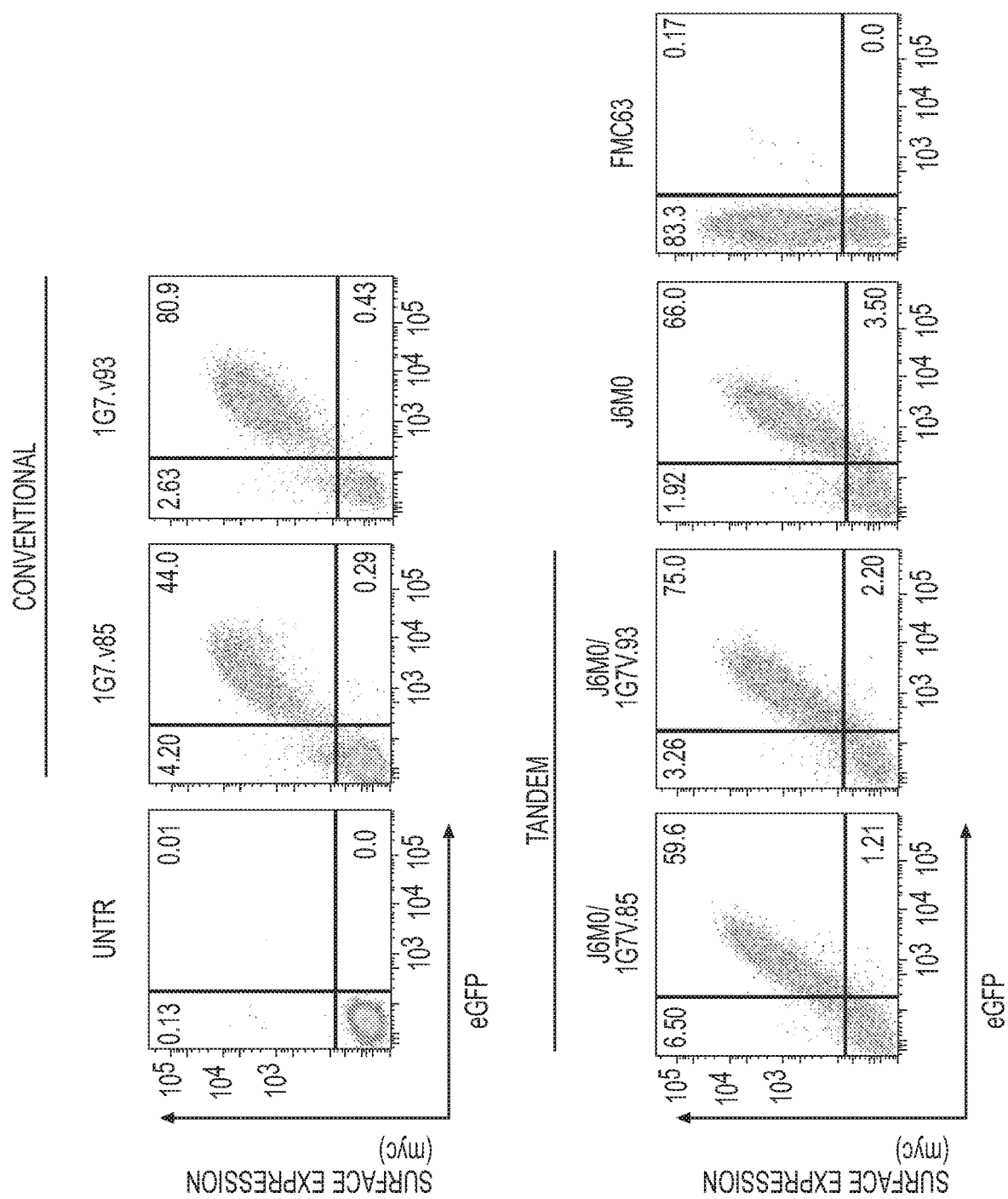
FIG. 14 is representative FACS dot plots of anti-CD307 and anti-BCMA CAR expression in primary human T cells expressing conventional CARs against CD307 (1G7.v85 and 1G7.v93), tandem CARs against BCMA and CD307 (J6M0/1G7v.85 and J6M0/1G7v.93), conventional CAR against BCMA (J6M0), or conventional CAR against CD19 (FMC63).
Figure 16:
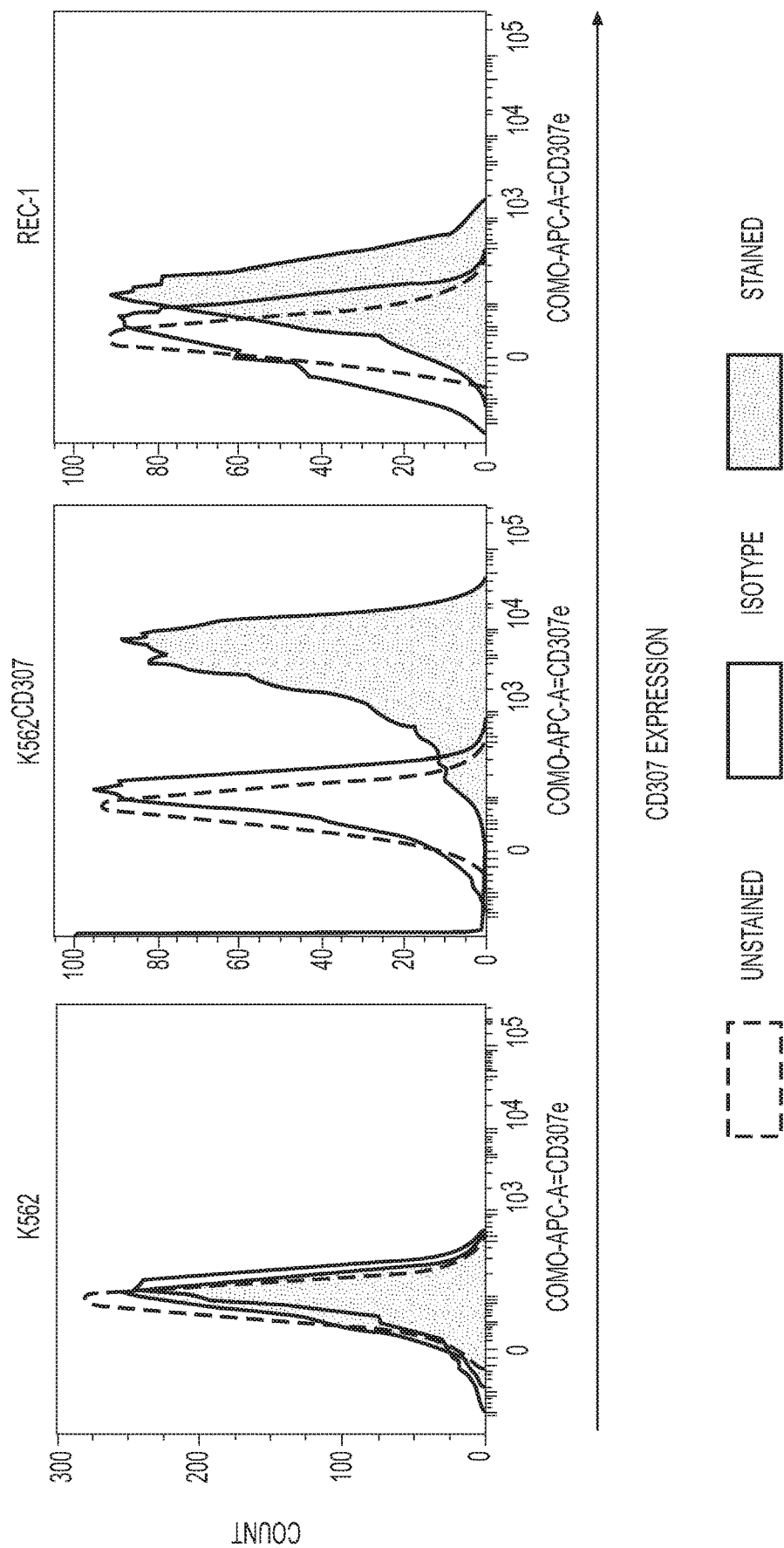
FIG. 16 is a representative FACS histogram plot showing CD307 expression in antigen negative K-562 tumor cells, K562$^{CD307}$ tumor cells, REC-1 tumor cells, unstained cells, and isotype controls.
Figure 17B:
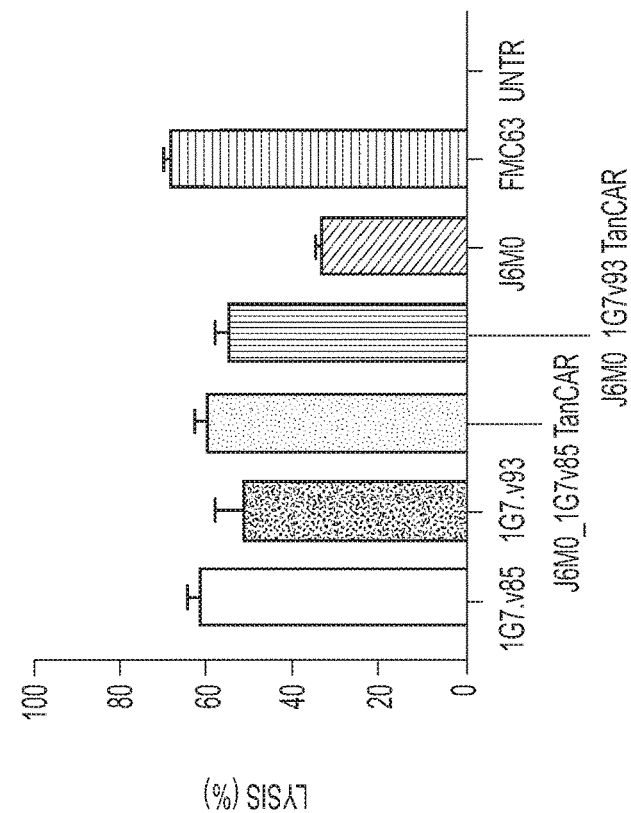
FIG. 17B is a representative graph of REC-1 tumor cell lysis following incubation with 1G7.v85, 1G7.v93, J6M0_1G7v85 TanCAR, J6M0_1G7v93 TanCAR, J6M0, FMC63 control, or untransduced (UNTR) T cells. The effector to target (E:T) ratio used was 1:1.
Figure 17A:
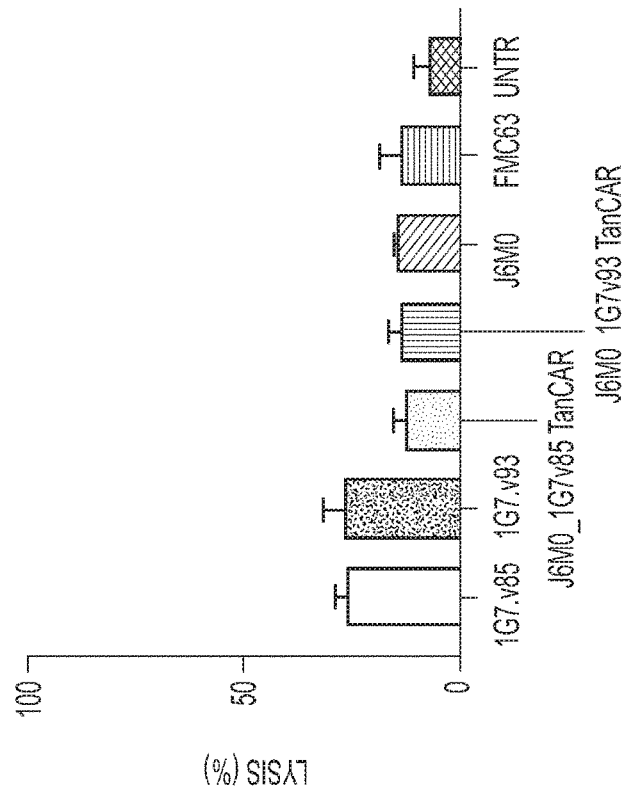
FIG. 17A is a representative graph of antigen negative K562 tumor cell lysis following incubation with 1G7.v85, 1G7.v93, J6M0_1G7v85 TanCAR, J6M0_1G7v93 TanCAR, J6M0, FMC63 control, or untransduced (UNTR) T cells. The effector to target (E:T) ratio used was 1:1.
Figure 18:
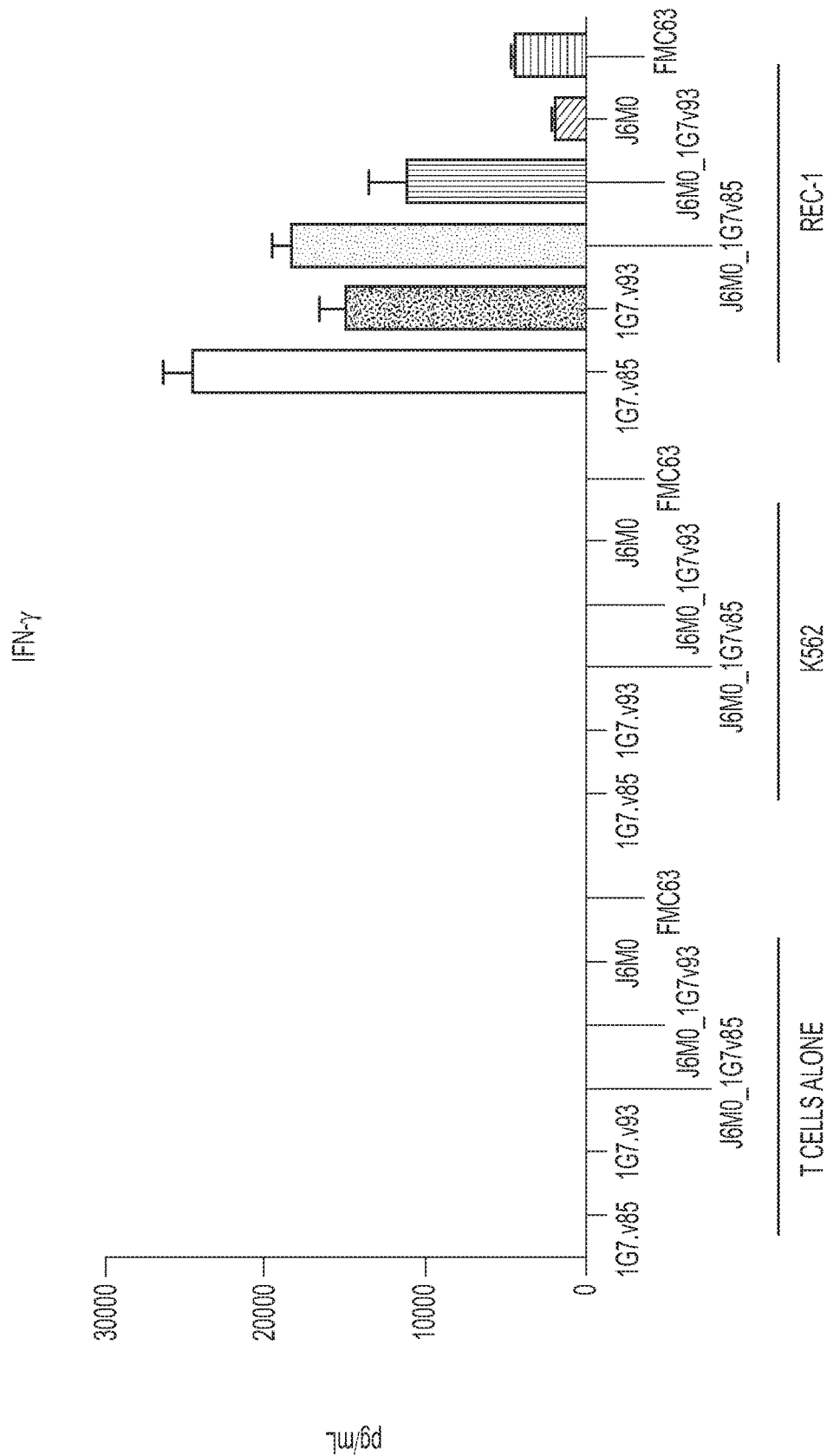
FIG. 18 is a representative graph of IFNγ levels following incubation of T cells alone, antigen-negative K562 tumor cells and REC-1 tumor cells with 1G7.v85, 1G7.v93, J6M0_1G7v85 TanCAR, J6M0_1G7v93 TanCAR, J6M0, or FMC63 control T cells.

Without wishing to be bound by theory, optimization strategies were developed to allow for incorporation of multiple dual-targeting approaches. FIGS. 17A, 17B, & 18 showed that 1G7 recognized endogenous levels of CD307 and generated high levels of IFNγ, however, high background cytotoxicity was also detected (data not shown). FIG. 14 showed expression of 1G7 tandem CARs in primary human T cells. Next, cell lysis was determined in K562 cells following incubation with 1G7 tandem CARs (FIGS. 15A-D and Table 2). To further test the sensitivity of 1 G7 tandem CARs, the effect of 1 G7 tandem CARs in cells expressing endogenous levels of CD307e was tested. As shown in FIG. 16, CD307e+ K562 cells express much higher levels of CD307e as compared to REC-1 cells, which express endogenous levels of CD307e. The 1G7 based tandem CAR was shown to be capable of killing the REC-1 cells (FIG. 17 A-B) and produced cytokine in response to CD307 presented on this target cell line (FIG. 18). In addition, the moderate background cytotoxicity observed from the conventional CAR was abrogated when the 1G7 scFv was included in the tandem CAR design (FIG. 17A).

The following materials and methods were used in the experiments described below.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A chimeric antigen receptor (CAR) comprising:
    a first antigen-binding domain that binds specifically to B-cell maturation antigen (BCMA), the first antigen binding domain comprising a VL CDR1 comprising the amino acid sequence of SEQ ID NO: 101, a VL CDR2 comprising the amino acid sequence of SEQ ID NO: 102, a VL CDR3 comprising the amino acid sequence of SEQ ID NO: 103, VH CDR1 comprising the amino acid sequence of SEQ ID NO: 104, a VL VH CDR2 comprising the amino acid sequence of SEQ ID NO: 105, a VH CDR3 comprising the amino acid sequence of SEQ ID NO: 106;
    a second antigen-binding domain that binds specifically to CD307e, the second antigen binding domain comprising a first set of CDRs, a second set of CDRs, or a third set of CDRs, wherein,
    the first set of CDRs comprises a VL CDR1 comprising the amino acid sequence of SEQ ID NO: 107, a VL CDR2 comprising the amino acid sequence of SEQ ID NO: 108, a VL CDR3 comprising the amino acid sequence of SEQ ID NO: 109, a VH CDR1 comprising the amino acid sequence of SEQ ID NO: 110, a VH CDR2 comprising the amino acid sequence of SEQ ID NO: 111, and a VH CDR3 comprising the amino acid sequence of SEQ ID NO: 112;
    the second set of CDRs comprises a VL CDR1 comprising the amino acid sequence of SEQ ID NO: 119, a VL CDR2 comprising the amino acid sequence of SEQ ID NO: 120, a VL CDR3 comprising the amino acid sequence of SEQ ID NO: 121, a VH CDR1 comprising the amino acid sequence of SEQ ID NO: 122, a VH CDR2 comprising the amino acid sequence of SEQ ID NO: 123, and a VH CDR3 comprising the amino acid sequence of SEQ ID NO: 124; and
    the third set of CDRs comprises a VL CDR1 comprising the amino acid sequence of SEQ ID NO: 125, a VL CDR2 comprising the amino acid sequence of SEQ ID NO: 126, a VL CDR3 comprising the amino acid sequence of SEQ ID NO: 127, a VH CDR1 comprising the amino acid sequence of SEQ ID NO: 128, a VH CDR2 comprising the amino acid sequence of SEQ ID NO: 129, a VH CDR3 comprising the amino acid sequence of SEQ ID NO: 130;
    a linker that is positioned between the first antigen-binding domain and the second antigen-binding domain;
    a transmembrane domain comprising the amino acid sequence of SEQ ID NO: 48;
    a hinge sequence that is positioned between the first antigen-binding domain and the transmembrane domain comprising the amino acid sequence of SEQ ID NO: 81;
    a co-stimulatory domain comprising the amino acid sequence of SEQ ID NO: 93; and
    an intracellular signaling domain comprising the amino acid sequence of SEQ ID NO: 85.

2. The CAR of claim 1, wherein one or both of the first antigen-binding domain and the second antigen-binding domain is a single-chain variable fragment (scFv).

3. The CAR of claim 1, wherein the first antigen binding domain comprises SEQ ID NO: 1 and SEQ ID NO: 2.

4. The CAR of claim 3, wherein the second antigen binding domain comprises SEQ ID NO: 5 and SEQ ID NO: 6.

5. The CAR of claim 3, wherein the second antigen binding domain comprises SEQ ID NO: 13 and SEQ ID NO: 14.

6. The CAR of claim 3, wherein the second antigen binding domain comprises SEQ ID NO: 17 and SEQ ID NO: 18.

7. The CAR of claim 3, wherein the second antigen binding domain comprises SEQ ID NO: 9 and SEQ ID NO: 10.

8. The CAR of claim 1, wherein the second antigen binding domain comprises SEQ ID NO: 5 and SEQ ID NO: 6.

9. The CAR of claim 1, wherein the second antigen binding domain comprises SEQ ID NO: 13 and SEQ ID NO: 14.

10. The CAR of claim 1, wherein the second antigen binding domain comprises SEQ ID NO: 17 and SEQ ID NO: 18.

11. The CAR of claim 1, wherein the second antigen binding domain comprises SEQ ID NO: 9 and SEQ ID NO: 10.

* * * * *

SEQUENCE LISTING

```
<160> NUMBER OF SEQ ID NOS: 130

<210> SEQ ID NO 1
<211> LENGTH: 108
<212> TYPE: PRT
<213> ORGANISM: Artificial
<220> FEATURE:
<223> OTHER INFORMATION: J6M0 Light Chain Variable

<400> SEQUENCE: 1

Asp Ile Gln Met Thr Gln Ser Pro Ser Ser Leu Ser Ala Ser Val Gly
```

```
              1               5                  10                 15
            Asp Arg Val Thr Ile Thr Cys Ser Ala Ser Gln Asp Ile Ser Asn Tyr
                              20                 25                 30

Leu Asn Trp Tyr Gln Gln Lys Pro Gly Lys Ala Pro Lys Leu Leu Ile
                    35                 40                 45

Tyr Tyr Thr Ser Asn Leu His Ser Gly Val Pro Ser Arg Phe Ser Gly
                50                 55                 60

Ser Gly Ser Gly Thr Asp Phe Thr Leu Thr Ile Ser Ser Leu Gln Pro
            65                  70                 75                 80

Glu Asp Phe Ala Thr Tyr Tyr Cys Gln Gln Tyr Arg Lys Leu Pro Trp
                            85                 90                 95

Thr Phe Gly Gln Gly Thr Lys Leu Glu Ile Lys Arg
                        100                105
```

<210> SEQ ID NO 2
<211> LENGTH: 121
<212> TYPE: PRT
<213> ORGANISM: Artificial
<220> FEATURE:
<223> OTHER INFORMATION: J6M0 Heavy Chain Variable

<400> SEQUENCE: 2

```
            Gln Val Gln Leu Val Gln Ser Gly Ala Glu Val Lys Lys Pro Gly Ser
            1               5                  10                 15

Ser Val Lys Val Ser Cys Lys Ala Ser Gly Gly Thr Phe Ser Asn Tyr
                            20                 25                 30

Trp Met His Trp Val Arg Gln Ala Pro Gly Gln Gly Leu Glu Trp Met
                        35                 40                 45

Gly Ala Thr Tyr Arg Gly His Ser Asp Thr Tyr Tyr Asn Gln Lys Phe
                50                 55                 60

Lys Gly Arg Val Thr Ile Thr Ala Asp Lys Ser Thr Ser Thr Ala Tyr
            65                  70                 75                 80

Met Glu Leu Ser Ser Leu Arg Ser Glu Asp Thr Ala Val Tyr Tyr Cys
                            85                 90                 95

Ala Arg Gly Ala Ile Tyr Asp Gly Tyr Asp Val Leu Asp Asn Trp Gly
                        100                105                110

Gln Gly Thr Leu Val Thr Val Ser Ser
                    115                120
```

<210> SEQ ID NO 3
<211> LENGTH: 324
<212> TYPE: DNA
<213> ORGANISM: Artificial
<220> FEATURE:
<223> OTHER INFORMATION: J6M0 Light Chain Variable Domain

<400> SEQUENCE: 3

```
gatatacaaa tgacccaaag cccaagctct ctgagtgcgt ccgtcgggga cagagtgaca        60
ataacatgta gtgcgtctca ggacatcagt aactacctga actggtacca gcaaaaacca       120
ggtaaggctc ccaagctgct tatttattat acctcaaatc tgcacagcgg cgttccatca       180
cgcttttctg gctctggcag tgggacggac ttcaccctca caatttctag ccttcaacca       240
gaagatttcg ccacttacta ctgtcaacag taccggaagc tgccctggac gttcgggcag       300
ggaacaaaac ttgaaatcaa gcgg                                              324
```

<210> SEQ ID NO 4
<211> LENGTH: 363

-continued

```
<212> TYPE: DNA
<213> ORGANISM: Artificial
<220> FEATURE:
<223> OTHER INFORMATION: J6M0 Heavy Chain Variable Domain

<400> SEQUENCE: 4
caagtccagc tggttcaatc cggagctgag gtgaaaaaac caggctcaag cgttaaggtt    60
tcttgcaagg ccagtggggg gactttctcc aactactgga tgcactgggt acggcaggcc   120
cccggtcaag gcttgaatg gatgggtgcc acgtacagag acactcaga cacatactat    180 aaccaaaaat tcaaggggcg agttactatt actgcagaca gtcaacttc tacagcctac   240 atggaattgt cctcccttag gtctgaagac acagcagtgt actattgcgc gcgggggccc   300
atatacgacg gatacgacgt gcttgataac tggggccagg gcaccctcgt gactgttagc   360
tcc                                                                 363

<210> SEQ ID NO 5
<211> LENGTH: 108
<212> TYPE: PRT
<213> ORGANISM: Artificial
<220> FEATURE:
<223> OTHER INFORMATION: 10A8 Human Light Chain Variable Domain

<400> SEQUENCE: 5

Asp Ile Gln Met Thr Gln Ser Pro Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Phe Ser Ser Pro Arg
                85                  90                  95

Thr Phe Gly Gln Gly Thr Lys Val Glu Ile Lys Arg
            100                 105

<210> SEQ ID NO 6
<211> LENGTH: 119
<212> TYPE: PRT
<213> ORGANISM: Artificial
<220> FEATURE:
<223> OTHER INFORMATION: 10A8 Human Heavy Chain Variable Domain

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Val Ser Trp Val Arg Gln Ala Pro Gly Lys Gly Leu Glu Trp Val
        35                  40                  45

Ala Thr Ile Ser Ser Gly Gly Ser Leu Thr Phe Tyr Leu Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Pro Ile Pro Asp Tyr Tyr Ala Leu Asp Tyr Trp Gly Gln Gly
            100                 105                 110

Thr Leu Val Thr Val Ser Ser
        115

<210> SEQ ID NO 7
<211> LENGTH: 324
<212> TYPE: DNA
<213> ORGANISM: Artificial
<220> FEATURE:
<223> OTHER INFORMATION: 10A8 Human Light Chain Variable Domain

<400> SEQUENCE: 7
gatatccaga tgacccagtc tcctagttcc ttgtccgcat cagtaggaga cagggtcacc      60
atcacctgca aggccagtca ggatgtgagt actgctgtag cctggtatca acagaaacca    120
ggaaaagctc ctaaactact gatttattcg gcatcctacc ggtacactgg agtcccttct    180
cgcttctctg gcagtggatc tgggacggat ttcactctca ccatcagcag tctgcagcct    240
gaagactttg caacttatta ctgtcagcaa cattttagta gtcctcggac gttcggtcaa    300
ggtaccaagg tggagatcaa acga                                           324

<210> SEQ ID NO 8
<211> LENGTH: 357
<212> TYPE: DNA
<213> ORGANISM: Artificial
<220> FEATURE:
<223> OTHER INFORMATION: 10A8 Human Heavy Chain Variable Domain

<400> SEQUENCE: 8
gaagtgcagt tggtggagtc tgggggaggc ttagtgcagc ctggagggtc cctgcgactc      60
tcctgtgcag cctctggatt cactttcagt agctatgccg tgtcttgggt tcgccaggct    120
ccggggaagg gactggagtg ggtcgctacc attagcagtg gtggtagttt gaccttctat    180
ttagacagtg tgaggggtcg attcaccatc tccagagaca atagcaagaa caccctgtac    240
ctgcaaatga atagtctgag ggctgaagac acggccgtgt attactgtgc aaggcccatt    300
ccggattact atgctttgga ctactggggt caaggaacct tagtcaccgt ctcctca       357

<210> SEQ ID NO 9
<211> LENGTH: 108
<212> TYPE: PRT
<213> ORGANISM: Artificial
<220> FEATURE:
<223> OTHER INFORMATION: 10A8 Mouse Light Chain Variable Domain

<400> SEQUENCE: 9

Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Phe Ser Ser Pro Arg
                85                  90                  95

Thr Phe Gly Gly Gly Thr Lys Val Glu Ile Lys Arg
        100                 105

<210> SEQ ID NO 10
<211> LENGTH: 119
<212> TYPE: PRT
<213> ORGANISM: Artificial
<220> FEATURE:
<223> OTHER INFORMATION: 10A8 Mouse Heavy Chain Variable Domain

<400> SEQUENCE: 10

Glu Val Gln Leu Val Glu Ser Gly Gly Gly Leu Val Lys Pro Gly Gly
1               5                   10                  15

Ser Leu Lys Ile Ser Cys Ala Ala Ser Gly Phe Thr Phe Ser Ser Tyr
            20                  25                  30

Ala Val Ser Trp Val Arg Gln Thr Pro Glu Lys Arg Leu Glu Trp Val
        35                  40                  45

Ala Thr Ile Ser Ser Gly Gly Ser Leu Thr Phe Tyr Leu Asp Ser Val
    50                  55                  60

Arg Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Pro Ile Pro Asp Tyr Tyr Ala Leu Asp Tyr Trp Gly Gln Gly
            100                 105                 110

Thr Ser Val Thr Val Ser Ser
        115

<210> SEQ ID NO 11
<211> LENGTH: 324
<212> TYPE: DNA
<213> ORGANISM: Artificial
<220> FEATURE:
<223> OTHER INFORMATION: 10A8 Mouse Light Chain Variable Domain

<400> SEQUENCE: 11
gatatcgtga tgacccagtc tcataaattc atgtccacat cagtaagaga cagggtcagc       60
atcacctgca aggccagtca ggatgtgagt actgctgtag cctggtatca acagaaacca      120
ggacaatctc ctaaactact gatttattcg gcatcctacc ggtacactgg agtccctgat      180
cgcttcactg gcagtggatc tgggacggat ttcactttca ccatcagcag tgtgcaggct      240
gaagacctgg cagtttatta ctgtcagcaa cattttagta gtcctcggac gttcggtgga      300
ggtaccaagg tggagatcaa acga                                             324

<210> SEQ ID NO 12
<211> LENGTH: 357
<212> TYPE: DNA
<213> ORGANISM: Artificial
<220> FEATURE:
<223> OTHER INFORMATION: 10A8 Mouse Heavy Chain Variable Domain

<400> SEQUENCE: 12
gaagtgcagt tggtggagtc tgggggaggc ttagtgaagc ctggagggtc cctgaaaatc       60
tcctgtgcag cctctggatt cactttcagt agctatgccg tgtcttgggt tcgccagact      120
ccggagaaga ggctggagtg gtcgctacc attagcagtg gtggtagttt gaccttctat       180
ttagacagtg tgaggggtcg attcaccatc tccagagaca tgccaagaa caccctgtac      240 ctgcaaatga gcagtctgag gtctgaagac acggccatgt attactgtgc aaggcccatt    300
ccggattact atgctttgga ctactggggt caaggaacct cagtcaccgt ctcctca        357

<210> SEQ ID NO 13
<211> LENGTH: 107
<212> TYPE: PRT
<213> ORGANISM: Artificial
<220> FEATURE:
<223> OTHER INFORMATION: 1G7.v85 Light Chain Variable Domain

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Leu
            20                  25                  30

Val Val Trp Phe Gln Gln Lys Pro Gly Lys Ala Pro Lys Leu Leu Ile
        35                  40                  45

Tyr Ser Gly Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Pro Pro Tyr
                85                  90                  95

Thr Phe Gly Gln Gly Thr Lys Val Glu Ile Lys
            100                 105

<210> SEQ ID NO 14
<211> LENGTH: 120
<212> TYPE: PRT
<213> ORGANISM: Artificial
<220> FEATURE:
<223> OTHER INFORMATION: 1G7.v85 Heavy Chain Variable Domain

<400> SEQUENCE: 14

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Arg Phe
            20                  25                  30

Gly Val His Trp Val Arg Gln Pro Pro Gly Lys Gly Leu Glu Trp Leu
        35                  40                  45

Gly Val Ile Trp Arg Gly Gly Ser Thr Asp Tyr Asn Ala Ala Phe Val
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Leu Val Thr Val Ser Ser
        115                 120

<210> SEQ ID NO 15
<211> LENGTH: 321
<212> TYPE: DNA
<213> ORGANISM: Artificial
<220> FEATURE:
<223> OTHER INFORMATION: 1G7.v85 Light Chain Variable Domain

<400> SEQUENCE: 15
gatattcaga tgacccagag cccgagcagc ctgagcgcga gcgtgggcga tcgcgtgacc        60

```
attacctgca aagcgagcca ggatgtgcgc aacctggtgg tgtggtttca gcagaaaccg      120
ggcaaagcgc cgaaactgct gatttatagc ggcagctatc gctatagcgg cgtgccgagc      180
cgctttagcg gcagcggcag cggcaccgat tttaccctga ccattagcag cctgcagccg      240
gaagattttg cgacctatta ttgccagcag cattatagcc gccgtatac ctttggccag       300 ggcaccaaag tggaaattaa a                                                321
```

<210> SEQ ID NO 16
<211> LENGTH: 360
<212> TYPE: DNA
<213> ORGANISM: Artificial
<220> FEATURE:
<223> OTHER INFORMATION: 1G7.v85 Heavy Chain Variable Domain

<400> SEQUENCE: 16

```
gaagtgcagc tggtggaaag cggcccaggc ctggtgaaac cgagcgaaac cctgagcctg       60
acctgcaccg tgagcggctt tagcctgacc cgctttggcg tgcattgggt gcgccagccg      120
ccgggcaaag gcctggaatg gctgggcgtg atttggcgcg gcggcagcac cgattataac      180
gcggcgtttg tgagccgcct gaccattagc aaagataaca gcaaaaacca ggtgagcctg      240
aaactgagca gcgtgaccgc ggcggatacc gcggtgtatt attgcagcaa ccattattat      300
ggcagcagcg attatgcgct ggataactgg ggccagggca ccctggtgac cgtgagcagc      360
```

<210> SEQ ID NO 17
<211> LENGTH: 107
<212> TYPE: PRT
<213> ORGANISM: Artificial
<220> FEATURE:
<223> OTHER INFORMATION: 1G7.v93 Light Chain Variable Domain

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Asn Leu
            20                  25                  30

Val Val Trp Phe Gln Gln Lys Pro Gly Lys Ala Pro Lys Leu Leu Ile
        35                  40                  45

Tyr Ser Gly Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Pro Pro Tyr
                85                  90                  95

Thr Phe Gly Gln Gly Thr Lys Val Glu Ile Lys
            100                 105
```

<210> SEQ ID NO 18
<211> LENGTH: 120
<212> TYPE: PRT
<213> ORGANISM: Artificial
<220> FEATURE:
<223> OTHER INFORMATION: 1G7.v93 Heavy Chain Variable Domain

<400> SEQUENCE: 18

```
Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Thr Thr Arg Phe
            20                  25                  30
```

```
Gly Val His Trp Val Arg Gln Pro Gly Lys Gly Leu Glu Trp Leu
         35                  40                  45

Gly Val Ile Trp Arg Gly Ser Thr Asp Tyr Asn Ala Ala Phe Val
     50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ser
                85                  90                  95

Asn His Tyr Tyr Gly Ser Pro Asp Tyr Ala Leu Asp Asn Trp Gly Gln
            100                 105                 110

Gly Thr Leu Val Thr Val Ser Ser
        115                 120
```

<210> SEQ ID NO 19
<211> LENGTH: 321
<212> TYPE: DNA
<213> ORGANISM: Artificial
<220> FEATURE:
<223> OTHER INFORMATION: 1G7.v93 Light Chain Variable Domain

<400> SEQUENCE: 19

```
gatattcaga tgacccagag cccgagcagc ctgagcgcga gcgtgggcga tcgcgtgacc      60
attacctgca aagcgagcca ggatgtgagc aacctggtgg tgtggtttca gcagaaaccg     120
ggcaaagcgc cgaaactgct gatttatagc ggcagctatc gctatagcgg cgtgccgagc     180
cgctttagcg gcagcggcag cggcaccgat tttaccctga ccattagcag cctgcagccg     240
gaagattttg cgacctatta ttgccagcag cattatagcc gccgtatac ctttggccag      300
ggcaccaaag tggaaattaa a                                                321
```

<210> SEQ ID NO 20
<211> LENGTH: 360
<212> TYPE: DNA
<213> ORGANISM: Artificial
<220> FEATURE:
<223> OTHER INFORMATION: 1G7.v93 Heavy Chain Variable Domain

<400> SEQUENCE: 20

```
gaagtgcagc tggtggaaag cggcccgggc ctggtgaaac cgagcgaaac cctgagcctg      60
acctgcaccg tgagcggctt tagcacgacc cgctttggcg tgcattgggt gcgccagccg     120
ccgggcaaag gcctggaatg gctgggcgtg atttggcgcg gcggcagcac cgattataac     180
gcggcgtttg tgagccgcct gaccattagc aaagataaca gcaaaaacca ggtgagcctg     240
aaactgagca gcgtgaccgc ggcggatacc gcggtgtatt attgcagcaa ccattattat     300
ggcagccccg attatgcgct ggataactgg ggccagggca ccctggtgac cgtgagcagc     360
```

<210> SEQ ID NO 21
<211> LENGTH: 15
<212> TYPE: PRT
<213> ORGANISM: Artificial
<220> FEATURE:
<223> OTHER INFORMATION: Linker

<400> SEQUENCE: 21

```
Ser Gly Gly Gly Gly Ser Gly Gly Gly Gly Ser Gly Gly Gly Gly
1               5                   10                  15
```

<210> SEQ ID NO 22
<211> LENGTH: 19
<212> TYPE: PRT

```
<213> ORGANISM: Artificial
<220> FEATURE:
<223> OTHER INFORMATION: Linker

<400> SEQUENCE: 22

Ala Ser Thr Lys Gly Pro Ser Val Phe Pro Leu Ala Pro Ser Ser
1               5                   10                  15

Gly Ser Gly

<210> SEQ ID NO 23
<211> LENGTH: 15
<212> TYPE: PRT
<213> ORGANISM: Artificial
<220> FEATURE:
<223> OTHER INFORMATION: Linker

<400> SEQUENCE: 23

Gly Gly Gly Gly Ser Gly Gly Gly Ser Gly Gly Gly Gly Ser
1               5                   10                  15

<210> SEQ ID NO 24
<211> LENGTH: 54
<212> TYPE: DNA
<213> ORGANISM: Artificial
<220> FEATURE:
<223> OTHER INFORMATION: Whitlow linker

<400> SEQUENCE: 24
ggcagcacca gcggcagcgg caaaccgggc agcggcgaag gcagcaccaa aggc         54

<210> SEQ ID NO 25
<211> LENGTH: 25
<212> TYPE: PRT
<213> ORGANISM: Artificial
<220> FEATURE:
<223> OTHER INFORMATION: (G4S)5 linker

<400> SEQUENCE: 25

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 26
<211> LENGTH: 75
<212> TYPE: DNA
<213> ORGANISM: Artificial
<220> FEATURE:
<223> OTHER INFORMATION: (G4S)5 linker

<400> SEQUENCE: 26
ggcggtggtg gttctggagg cggtggcagc ggtggaggtg gctcaggagg aggaggtagc    60
ggcggcggag ggagt                                                    75

<210> SEQ ID NO 27
<211> LENGTH: 233
<212> TYPE: PRT
<213> ORGANISM: Artificial
<220> FEATURE:
<223> OTHER INFORMATION: Human IgG1 CH2-CH3 domains

<400> SEQUENCE: 27

Ala Glu Pro Lys Ser Pro Asp Lys Thr His Thr Cys Pro Pro Cys Pro
1               5                   10                  15
```

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Trp Val
            35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
            130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
210                 215                 220

Leu Ser Leu Ser Pro Gly Lys Lys Asp
225                 230

<210> SEQ ID NO 28
<211> LENGTH: 46
<212> TYPE: PRT
<213> ORGANISM: Artificial
<220> FEATURE:
<223> OTHER INFORMATION: Human CD8 Sequence

<400> SEQUENCE: 28

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
            35                  40                  45

<210> SEQ ID NO 29
<211> LENGTH: 20
<212> TYPE: PRT
<213> ORGANISM: Artificial
<220> FEATURE:
<223> OTHER INFORMATION: Human IgG1 Hinge Sequence

<400> SEQUENCE: 29

Ala Glu Pro Lys Ser Pro Asp Lys Thr His Thr Cys Pro Pro Cys Pro
1               5                   10                  15

Lys Asp Pro Lys
            20

<210> SEQ ID NO 30

<211> LENGTH: 184
<212> TYPE: PRT
<213> ORGANISM: Homo sapiens

<400> SEQUENCE: 30

Met Leu Gln Met Ala Gly Gln Cys Ser Gln Asn Glu Tyr Phe Asp Ser
1               5                   10                  15
Leu Leu His Ala Cys Ile Pro Cys Gln Leu Arg Cys Ser Ser Asn Thr
            20                  25                  30
Pro Pro Leu Thr Cys Gln Arg Tyr Cys Asn Ala Ser Val Thr Asn Ser
        35                  40                  45
Val Lys Gly Thr Asn Ala Ile Leu Trp Thr Cys Leu Gly Leu Ser Leu
    50                  55                  60
Ile Ile Ser Leu Ala Val Phe Val Leu Met Phe Leu Leu Arg Lys Ile
65                  70                  75                  80
Asn Ser Glu Pro Leu Lys Asp Glu Phe Lys Asn Thr Gly Ser Gly Leu
                85                  90                  95
Leu Gly Met Ala Asn Ile Asp Leu Glu Lys Ser Arg Thr Gly Asp Glu
            100                 105                 110
Ile Ile Leu Pro Arg Gly Leu Glu Tyr Thr Val Glu Glu Cys Thr Cys
        115                 120                 125
Glu Asp Cys Ile Lys Ser Lys Pro Lys Val Asp Ser Asp His Cys Phe
    130                 135                 140
Pro Leu Pro Ala Met Glu Gly Ala Thr Ile Leu Val Thr Thr Lys
145                 150                 155                 160
Thr Asn Asp Tyr Cys Lys Ser Leu Pro Ala Ala Leu Ser Ala Thr Glu
                165                 170                 175
Ile Glu Lys Ser Ile Ser Ala Arg
            180

<210> SEQ ID NO 31
<211> LENGTH: 994
<212> TYPE: DNA
<213> ORGANISM: Homo sapiens

<400> SEQUENCE: 31
aagactcaaa cttagaaact tgaattagat gtggtattca atccttagc tgccgcgaag      60
acacagacag cccccgtaag aacccacgaa gcaggcgaag ttcattgttc tcaacattct    120
agctgctctt gctgcatttg ctctggaatt cttgtagaga tattacttgt ccttccaggc    180
tgttctttct gtagctccct tgttttcttt ttgtgatcat gttgcagatg gctgggcagt    240
gctcccaaaa tgaatatttt gacagtttgt tgcatgcttg catacccttgt caacttcgat    300
gttcttctaa tactcctcct ctaacatgtc agcgttattg taatgcaagt gtgaccaatt    360
cagtgaaagg aacgaatgcg attctctgga cctgtttggg actgagctta ataatttctt    420
tggcagtttt cgtgctaatg ttttgctaa ggaagataaa ctctgaacca ttaaaggacg    480
agtttaaaaa cacaggatca ggtctcctgg gcatggctaa cattgacctg gaaaagagca    540
ggactggtga tgaaattatt cttccgagag gcctcgagta cacggtggaa gaatgcacct    600
gtgaagactg catcaagagc aaaccgaagg tcgactctga ccattgcttt ccactcccag    660
ctatggagga aggcgcaacc attcttgtca ccacgaaaac gaatgactat tgcaagagcc    720
tgccagctgc tttgagtgct acggagatag agaaatcaat ttctgctagg taattaacca    780
tttcgactcg agcagtgcca ctttaaaaat cttttgtcag aatagatgat gtgtcagatc    840
tctttaggat gactgtattt tcagttgcc gatacagctt tttgtcctct aactgtggaa    900

```
actctttatg ttagatatat ttctctaggt tactgttggg agcttaatgg tagaaacttc      960
cttggtttca tgattaaact cttttttttc ctga                                 994
```

<210> SEQ ID NO 32
<211> LENGTH: 135
<212> TYPE: PRT
<213> ORGANISM: Homo sapiens

<400> SEQUENCE: 32

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Arg Ser Gly Leu Leu
        35                  40                  45

Gly Met Ala Asn Ile Asp Leu Glu Lys Ser Arg Thr Gly Asp Glu Ile
    50                  55                  60

Ile Leu Pro Arg Gly Leu Glu Tyr Thr Val Glu Cys Thr Cys Glu
65                  70                  75                  80

Asp Cys Ile Lys Ser Lys Pro Lys Val Asp Ser Asp His Cys Phe Pro
                85                  90                  95

Leu Pro Ala Met Glu Glu Gly Ala Thr Ile Leu Val Thr Thr Lys Thr
            100                 105                 110

Asn Asp Tyr Cys Lys Ser Leu Pro Ala Ala Leu Ser Ala Thr Glu Ile
        115                 120                 125

Glu Lys Ser Ile Ser Ala Arg
    130                 135

<210> SEQ ID NO 33
<211> LENGTH: 668
<212> TYPE: DNA
<213> ORGANISM: Homo sapiens

<400> SEQUENCE: 33

```
gttctcaaca ttctagctgc tcttgctgca tttgctctgg aattcttgta gagatattac      60
ttgtccttcc aggctgttct ttctgtagct cccttgtttt cttttgtga tcatgttgca       120 gatggctggg cagtgctccc aaaatgaata ttttgacagt tgttgcatg cttgcatacc       180 ttgtcaactt cgatgttctt ctaatactcc tcctctaaca tgtcagcgtt attgtaatgc      240
aagatcaggt ctcctgggca tggctaacat tgacctggaa agagcagga ctggtgatga      300 aattattctt ccgagaggcc tcgagtacac ggtggaagaa tgcacctgtg aagactgcat      360
caagagcaaa ccgaaggtcg actctgacca ttgctttcca ctcccagcta tggaggaagg      420
cgcaaccatt cttgtcacca cgaaaacgaa tgactattgc aagagcctgc cagctgcttt      480
gagtgctacg gagatagaga atcaatttc tgctaggtaa ttaaccattt cgactcgagc      540
agtgccactt taaaaatctt ttgtcagaat agatgatgtg tcagatctct ttaggatgac      600 tgtattttc agttgccgat acagcttttt gtcctctaac tgtggaaact ctttatgtta      660
gatatatt                                                              668
```

<210> SEQ ID NO 34
<211> LENGTH: 977
<212> TYPE: PRT
<213> ORGANISM: Homo sapiens

<400> SEQUENCE: 34

```
Met Leu Leu Trp Val Ile Leu Val Leu Ala Pro Val Ser Gly Gln
1               5                   10                  15

Phe Ala Arg Thr Pro Arg Pro Ile Ile Phe Leu Gln Pro Trp Thr
                20                  25              30

Thr Val Phe Gln Gly Glu Arg Val Thr Leu Thr Cys Lys Gly Phe Arg
            35                  40                  45

Phe Tyr Ser Pro Gln Lys Thr Lys Trp Tyr His Arg Tyr Leu Gly Lys
50                      55                  60

Glu Ile Leu Arg Glu Thr Pro Asp Asn Ile Leu Glu Val Gln Glu Ser
65                  70                  75                  80

Gly Glu Tyr Arg Cys Gln Ala Gln Gly Ser Pro Leu Ser Ser Pro Val
                85                  90                  95

His Leu Asp Phe Ser Ser Ala Ser Leu Ile Leu Gln Ala Pro Leu Ser
                100                 105                 110

Val Phe Glu Gly Asp Ser Val Val Leu Arg Cys Arg Ala Lys Ala Glu
            115                 120                 125

Val Thr Leu Asn Asn Thr Ile Tyr Lys Asn Asp Asn Val Leu Ala Phe
130                 135                 140

Leu Asn Lys Arg Thr Asp Phe His Ile Pro His Ala Cys Leu Lys Asp
145                 150                 155                 160

Asn Gly Ala Tyr Arg Cys Thr Gly Tyr Lys Glu Ser Cys Cys Pro Val
                165                 170                 175

Ser Ser Asn Thr Val Lys Ile Gln Val Gln Glu Pro Phe Thr Arg Pro
            180                 185                 190

Val Leu Arg Ala Ser Ser Phe Gln Pro Ile Ser Gly Asn Pro Val Thr
        195                 200                 205

Leu Thr Cys Glu Thr Gln Leu Ser Leu Glu Arg Ser Asp Val Pro Leu
210                 215                 220

Arg Phe Arg Phe Phe Arg Asp Asp Gln Thr Leu Gly Leu Gly Trp Ser
225             230                 235                 240

Leu Ser Pro Asn Phe Gln Ile Thr Ala Met Trp Ser Lys Asp Ser Gly
            245                 250                 255

Phe Tyr Trp Cys Lys Ala Ala Thr Met Pro Tyr Ser Val Ile Ser Asp
            260                 265                 270

Ser Pro Arg Ser Trp Ile Gln Val Gln Ile Pro Ala Ser His Pro Val
        275                 280                 285

Leu Thr Leu Ser Pro Glu Lys Ala Leu Asn Phe Glu Gly Thr Lys Val
290                 295                 300

Thr Leu His Cys Glu Thr Gln Glu Asp Ser Leu Arg Thr Leu Tyr Arg
305                 310                 315                 320

Phe Tyr His Glu Gly Val Pro Leu Arg His Lys Ser Val Arg Cys Glu
            325                 330                 335

Arg Gly Ala Ser Ile Ser Phe Ser Leu Thr Thr Glu Asn Ser Gly Asn
        340                 345                 350

Tyr Tyr Cys Thr Ala Asp Asn Gly Leu Gly Ala Lys Pro Ser Lys Ala
            355                 360                 365

Val Ser Leu Ser Val Thr Val Pro Val Ser His Pro Val Leu Asn Leu
370                 375                 380

Ser Ser Pro Glu Asp Leu Ile Phe Glu Gly Ala Lys Val Thr Leu His
385                 390                 395                 400

Cys Glu Ala Gln Arg Gly Ser Leu Pro Ile Leu Tyr Gln Phe His His
                405                 410                 415
```

```
Glu Gly Ala Ala Leu Glu Arg Arg Ser Ala Asn Ser Ala Gly Gly Val
            420                 425                 430

Ala Ile Ser Phe Ser Leu Thr Ala Glu His Ser Gly Asn Tyr Tyr Cys
            435                 440                 445

Thr Ala Asp Asn Gly Phe Gly Pro Gln Arg Ser Lys Ala Val Ser Leu
            450                 455                 460

Ser Val Thr Val Pro Val Ser His Pro Val Leu Thr Leu Ser Ser Ala
465                 470                 475                 480

Glu Ala Leu Thr Phe Glu Gly Ala Thr Val Thr Leu His Cys Glu Val
            485                 490                 495

Gln Arg Gly Ser Pro Gln Ile Leu Tyr Gln Phe Tyr His Glu Asp Met
            500                 505                 510

Pro Leu Trp Ser Ser Ser Thr Pro Ser Val Gly Arg Val Ser Phe Ser
            515                 520                 525

Phe Ser Leu Thr Glu Gly His Ser Gly Asn Tyr Tyr Cys Thr Ala Asp
            530                 535                 540

Asn Gly Phe Gly Pro Gln Arg Ser Glu Val Val Ser Leu Phe Val Thr
545                 550                 555                 560

Val Pro Val Ser Arg Pro Ile Leu Thr Leu Arg Val Pro Arg Ala Gln
            565                 570                 575

Ala Val Val Gly Asp Leu Leu Glu Leu His Cys Glu Ala Pro Arg Gly
            580                 585                 590

Ser Pro Pro Ile Leu Tyr Trp Phe Tyr His Glu Asp Val Thr Leu Gly
            595                 600                 605

Ser Ser Ser Ala Pro Ser Gly Gly Glu Ala Ser Phe Asn Leu Ser Leu
            610                 615                 620

Thr Ala Glu His Ser Gly Asn Tyr Ser Cys Glu Ala Asn Asn Gly Leu
625                 630                 635                 640

Val Ala Gln His Ser Asp Thr Ile Ser Leu Ser Val Ile Val Pro Val
            645                 650                 655

Ser Arg Pro Ile Leu Thr Phe Arg Ala Pro Arg Ala Gln Ala Val Val
            660                 665                 670

Gly Asp Leu Leu Glu Leu His Cys Glu Ala Leu Arg Gly Ser Ser Pro
            675                 680                 685

Ile Leu Tyr Trp Phe Tyr His Glu Asp Val Thr Leu Gly Lys Ile Ser
            690                 695                 700

Ala Pro Ser Gly Gly Gly Ala Ser Phe Asn Leu Ser Leu Thr Thr Glu
705                 710                 715                 720

His Ser Gly Ile Tyr Ser Cys Glu Ala Asp Asn Gly Leu Glu Ala Gln
            725                 730                 735

Arg Ser Glu Met Val Thr Leu Lys Val Ala Val Pro Val Ser Arg Pro
            740                 745                 750

Val Leu Thr Leu Arg Ala Pro Gly Thr His Ala Ala Val Gly Asp Leu
            755                 760                 765

Leu Glu Leu His Cys Glu Ala Leu Arg Gly Ser Pro Leu Ile Leu Tyr
            770                 775                 780

Arg Phe Phe His Glu Asp Val Thr Leu Gly Asn Arg Ser Ser Pro Ser
785                 790                 795                 800

Gly Gly Ala Ser Leu Asn Leu Ser Leu Thr Ala Glu His Ser Gly Asn
            805                 810                 815

Tyr Ser Cys Glu Ala Asp Asn Gly Leu Gly Ala Gln Arg Ser Glu Thr
            820                 825                 830

Val Thr Leu Tyr Ile Thr Gly Leu Thr Ala Asn Arg Ser Gly Pro Phe
```

```
                835                 840                 845
Ala Thr Gly Val Ala Gly Leu Leu Ser Ile Ala Gly Leu Ala Ala
            850                 855                 860
Gly Ala Leu Leu Leu Tyr Cys Trp Leu Ser Arg Lys Ala Gly Arg Lys
865                 870                 875                 880
Pro Ala Ser Asp Pro Ala Arg Ser Pro Ser Asp Ser Asp Ser Gln Glu
                    885                 890                 895
Pro Thr Tyr His Asn Val Pro Ala Trp Glu Glu Leu Gln Pro Val Tyr
                900                 905                 910
Thr Asn Ala Asn Pro Arg Gly Glu Asn Val Val Tyr Ser Glu Val Arg
                915                 920                 925
Ile Ile Gln Glu Lys Lys Lys His Ala Val Ala Ser Asp Pro Arg His
            930                 935                 940
Leu Arg Asn Lys Gly Ser Pro Ile Ile Tyr Ser Glu Val Lys Val Ala
945                 950                 955                 960
Ser Thr Pro Val Ser Gly Ser Leu Phe Leu Ala Ser Ser Ala Pro His
                    965                 970                 975
Arg
```

<210> SEQ ID NO 35
<211> LENGTH: 5395
<212> TYPE: DNA
<213> ORGANISM: Homo sapiens

<400> SEQUENCE: 35

```
aattcactaa tgcattctgc tctttttgag agcacagctt ctcagatgtg ctccttggag      60
ctggtgtgca gtgtcctgac tgtaagatca agtccaaacc tgttttggaa ttgaggaaac     120
ttctcttttg atctcagccc ttggtggtcc aggtcttcat gctgctgtgg gtgatattac     180
tggtcctggc tcctgtcagt ggacagtttg caaggacacc caggcccatt atttttcctcc    240
agcctccatg gaccacagtc ttccaaggag agagagtgac cctcacttgc aagggatttc     300
gcttctactc accacagaaa acaaaatggt accatcggta ccttgggaaa gaaatactaa     360
gagaaacccc agacaatatc cttgaggttc aggaatctgg agagtacaga tgccaggccc     420
agggctcccc tctcagtagc cctgtgcact tgatttttc ttcagcttcg ctgatcctgc      480
aagctccact ttctgtgttt gaaggagact ctgtggttct gaggtgccgg gcaaaggcgg     540
aagtaacact gaataatact atttacaaga atgataatgt cctggcattc ttaataaaa      600
gaactgactt ccatattcct catgcatgtc tcaaggacaa tggtgcatat cgctgtactg     660
gatataagga agttgttgc cctgtttctt ccaatacagt caaaatccaa gtccaagagc      720
catttacacg tccagtgctg agagccagct ccttccagcc catcagcggg aacccagtga     780
ccctgacctg tgagacccag ctctctctag agaggtcaga tgtcccgctc cggttccgct     840
tcttcagaga tgaccagacc tgggattag gctggagtct ccccccgaat ttccagatta     900
ctgccatgtg gagtaaagat tcaggggttct actggtgtaa ggcagcaaca atgccttaca    960
gcgtcatatc tgacagcccg agatcctgga tacaggtgca gatccctgca tctcatcctg    1020
tcctcactct cagccctgaa aaggctctga attttgaggg aaccaaggtg cacttcact    1080
gtgaaaccca ggaagattct ctgcgcactt tgtacaggtt ttatcatgag ggtgtccccc    1140
tgaggcacaa gtcagtccgc tgtgaaaggg gagcatccat cagcttctca ctgactacag    1200
agaattcagg gaactactac tgcacagctg acaatggcct tggcgccaag cccagtaagg    1260
ctgtgagcct ctcagtcact gttcccgtgt ctcatcctgt cctcaacctc agctctcctg    1320
```

```
aggacctgat ttttgaggga gccaaggtga cacttcactg tgaagcccag agaggttcac   1380
tccccatcct gtaccagttt catcatgagg gtgctgccct ggagcgtagg tcggccaact   1440
ctgcaggagg agtggccatc agcttctctc tgactgcaga gcattcaggg aactactact   1500
gcacagctga caatggcttt ggcccccagc gcagtaaggc ggtgagcctc tccgtcactg   1560
tccctgtgtc tcatcctgtc ctcaccctca gctctgctga ggccctgact tttgaaggag   1620
ccactgtgac acttcactgt gaagtccaga gaggttcccc acaaatccta taccagtttt   1680
atcatgagga catgcccctg tggagcagct caacaccctc tgtgggaaga gtgtccttca   1740
gcttctctct gactgaagga cattcaggga attactactg cacagctgac aatggctttg   1800
gtccccagcg cagtgaagtg gtgagccttt ttgtcactgt tccagtgtct cgccccatcc   1860
tcaccctcag ggttcccagg gcccaggctg tggtggggga cctgctggag cttcactgtg   1920
aggccccgag aggctctccc ccaatcctgt actggtttta tcatgaggat gtcaccctgg   1980
ggagcagctc agcccctct ggaggagaag cttctttcaa cctctctctg actgcagaac   2040
attctggaaa ctactcatgt gaggccaaca atggcctagt ggcccagcac agtgacacaa   2100
tatcactcag tgttatagtt ccagtatctc gtcccatcct caccttcagg gctcccaggg   2160
cccaggctgt ggtgggggac ctgctggagc ttcactgtga ggccctgaga ggctcctccc   2220
caatcctgta ctggttttat catgaagatg tcaccctggg taagatctca gcccctctg   2280 gaggagggc ctccttcaac ctctctctga ctacagaaca ttctggaatc tactcctgtg   2340
aggcagacaa tggtctggag gcccagcgca gtgagatggt gacactgaaa gttgcagttc   2400
cggtgtctcg cccggtcctc accctcaggg ctcccgggac ccatgctgcg gtggggacc   2460 tgctggagct tcactgtgag gccctgagag gctctcccct gatcctgtac cggttttttc   2520
atgaggatgt caccctagga aataggtcgt cccctctgg aggagcgtcc ttaaacctct   2580
ctctgactgc agagcactct ggaaactact cctgtgaggc cgacaatggc ctcggggccc   2640
agcgcagtga gacagtgaca ctttatatca cagggctgac cgcgaacaga agtggccctt   2700
ttgccacagg agtcgccggg ggcctgctca gcatagcagg ccttgctgcg ggggcactgc   2760
tgctctactg ctggctctcg agaaaagcag ggagaaagcc tgcctctgac cccgccagga   2820
gcccttcaga ctcggactcc caagagccca cctatcacaa tgtaccagcc tgggaagagc   2880
tgcaaccagt gtacactaat gcaaatccta gaggagaaaa tgtggtttac tcagaagtac   2940
ggatcatcca agagaaaaag aaacatgcag tggcctctga ccccaggcat ctcaggaaca   3000
agggttcccc tatcatctac tctgaagtta aggtggcgtc aaccccggtt tccggatccc   3060
tgttcttggc ttcctcagct cctcacagat gagtccacac gtctctccaa ctgctgtttc   3120
agcctctgca ccccaaagtt ccccttgggg gagaagcagc attgaagtgg gaagatttag   3180
gctgccccag accatatcta ctggcctttg tttcacatgt cctcattctc agtctgacca   3240
gaatgcaggg ccctgctgga ctgtcacctg tttcccagtt aaagccctga ctggcaggtt   3300
ttttaatcca gtggcaaggt gctcccactc agggcccag cacatctcct ggattcctta   3360
gtgggcttca gctgtggttg ctgttctgag tactgctctc atcacacccc cacagagggg   3420
gtcttaccac acaaagggag agtgggcctt caggagatgc cgggctggcc taacagctca   3480
ggtgctccta aactccgaca cagagttcct gctttgggtg gatgcatttc tcaattgtca   3540
tcagcctggt ggggctactg cagtgtgctg ccaaatggga cagcacacag cctgtgcaca   3600
tgggacatgt gatgggtctc cccacggggg ctgcatttca cactcctcca cctgtctcaa   3660
```

```
actctaaggt cggcacttga caccaaggta acttctctcc tgctcatgtg tcagtgtcta   3720
cctgcccaag taagtggctt tcatacacca agtcccaagt tcttcccatc ctaacagaag   3780
taacccagca agtcaaggcc aggaggacca ggggtgcaga cagaacacat actggaacac   3840
aggaggtgct caattactat ttgactgact gactgaatga atgaatgaat gaggaagaaa   3900
actgtgggta atcaaactgg cataaaatcc agtgcactcc ctaggaaatc cgggaggtat   3960
tctggcttcc ctaagaaaca atggaagaga aggagcttgg atgaggaaac tgttcagcaa   4020
gaggaagggc ttctcacact tcatgtgct tgtggatcac ctgaggatcc tgtgaaaata    4080
cagatactga ttcagtgggt ctgcgtagag cctgagactg ccattctaac atgttcccag   4140
gggatgctga tgctgctggc cctgggactg cactgcatgc atgtgaagcc ctataggtct   4200
cagcagaggc ccatggagag ggaatgtgtg gctctggctg cccagggccc aactcggttc   4260
acacggatcg tgctgctccc tggccagcct ttggccacag caccaccagc tgctgttgct   4320
gagagagctt cttctctgtg acatgttggc tttcatcagc cacctggga agcggaaagt    4380
agctgccact atctttgttt ccccacctca ggcctcacac tttcccatga aaagggtgaa   4440
tgtatataac ctgagccctc tccattcaga gttgttctcc catctctgag caatgggatg   4500
ttctgttccg cttttatgat atccatcaca tcttatcttg atctttgctc ccagtggatt   4560
gtacagtgat gactttcaag ccccacggcc ctgaaataaa atccttccaa gggcattgga   4620
agctcactcc acctgaacca tggcttttca tgcttccaag tgtcagggcc ttgcccagat   4680
agacagggct ggctctgctg ccccaacctt tcaaggagga aaccagacac ctgagacagg   4740
agcctgtatg cagcccagtg cagccttgca gaggacaagg ctggaggcat tgtcatcac   4800
tacagatatg caactaaaat agacgtggag caagagaaat gcattccac cgaggccgct   4860
tttttaggcc tagttgaaag tcaagaagga cagcagcaag cataggctca ggattaaaga   4920
aaaaaatctg ctcacagtct gttctggagg tcacatcacc aacaaagctc acgccctatg   4980
cagttctgag aaggtggagg caccaggctc aaaagaggaa atttagaatt tctcattggg   5040
agagtaaggt accccccatcc cagaatgata actgcacagt ggcagaacaa actccaccct   5100
aatgtgggtg gaccccgtcc agtctgttga aggcctgaat gtaacaaaag gcttattct    5160
tcctcaagta aggggaact cctgctttgg gctgggacat aagttttct gctttcagac     5220
gcaaactgaa aaatggctct tcttgggtct tgagcttgct ggcatatgga ctgaaagaaa   5280
ctatgctatt ggatctcctg gatctccagc ttgctgactg cagatcttga gatatgtcag   5340
cctctacagt cacaagagct aattcattct aataaaccaa tctttctgta aaaaa        5395
```

<210> SEQ ID NO 36
<211> LENGTH: 998
<212> TYPE: PRT
<213> ORGANISM: Homo sapiens

<400> SEQUENCE: 36

Met Leu Leu Trp Val Ile Leu Leu Val Leu Ala Pro Val Ser Gly Gln
1               5                   10                  15

Phe Ala Arg Thr Pro Arg Pro Ile Ile Phe Leu Gln Pro Pro Trp Thr
            20                  25                  30

Thr Val Phe Gln Gly Glu Arg Val Thr Leu Thr Cys Lys Gly Phe Arg
        35                  40                  45

Phe Tyr Ser Pro Gln Lys Thr Lys Trp Tyr His Arg Tyr Leu Gly Lys
    50                  55                  60

Glu Ile Leu Arg Glu Thr Pro Asp Asn Ile Leu Glu Val Gln Glu Ser

```
            65                  70                  75                  80
Gly Glu Tyr Arg Cys Gln Ala Gln Gly Ser Pro Leu Ser Ser Pro Val
                        85                  90                  95
His Leu Asp Phe Ser Ser Ala Ser Leu Ile Leu Gln Ala Pro Leu Ser
                    100                 105                 110
Val Phe Glu Gly Asp Ser Val Val Leu Arg Cys Arg Ala Lys Ala Glu
                115                 120                 125
Val Thr Leu Asn Asn Thr Ile Tyr Lys Asn Asp Asn Val Leu Ala Phe
            130                 135                 140
Leu Asn Lys Arg Thr Asp Phe His Ile Pro His Ala Cys Leu Lys Asp
145                 150                 155                 160
Asn Gly Ala Tyr Arg Cys Thr Gly Tyr Lys Glu Ser Cys Cys Pro Val
                    165                 170                 175
Ser Ser Asn Thr Val Lys Ile Gln Val Gln Glu Pro Phe Thr Arg Pro
                180                 185                 190
Val Leu Arg Ala Ser Ser Phe Gln Pro Ile Ser Gly Asn Pro Val Thr
                195                 200                 205
Leu Thr Cys Glu Thr Gln Leu Ser Leu Glu Arg Ser Asp Val Pro Leu
            210                 215                 220
Arg Phe Arg Phe Phe Arg Asp Asp Gln Thr Leu Gly Leu Gly Trp Ser
225                 230                 235                 240
Leu Ser Pro Asn Phe Gln Ile Thr Ala Met Trp Ser Lys Asp Ser Gly
                    245                 250                 255
Phe Tyr Trp Cys Lys Ala Ala Thr Met Pro Tyr Ser Val Ile Ser Asp
                260                 265                 270
Ser Pro Arg Ser Trp Ile Gln Val Gln Ile Pro Ala Ser His Pro Val
                275                 280                 285
Leu Thr Leu Ser Pro Glu Lys Ala Leu Asn Phe Glu Gly Thr Lys Val
            290                 295                 300
Thr Leu His Cys Glu Thr Gln Glu Asp Ser Leu Arg Thr Leu Tyr Arg
305                 310                 315                 320
Phe Tyr His Glu Gly Val Pro Leu Arg His Lys Ser Val Arg Cys Glu
                    325                 330                 335
Arg Gly Ala Ser Ile Ser Phe Ser Leu Thr Thr Glu Asn Ser Gly Asn
                340                 345                 350
Tyr Tyr Cys Thr Ala Asp Asn Gly Leu Gly Ala Lys Pro Ser Lys Ala
            355                 360                 365
Val Ser Leu Ser Val Thr Val Pro Val Ser His Pro Val Leu Asn Leu
            370                 375                 380
Ser Ser Pro Glu Asp Leu Ile Phe Glu Gly Ala Lys Val Thr Leu His
385                 390                 395                 400
Cys Glu Ala Gln Arg Gly Ser Leu Pro Ile Leu Tyr Gln Phe His His
                    405                 410                 415
Glu Gly Ala Ala Leu Glu Arg Arg Ser Ala Asn Ser Ala Gly Gly Val
                420                 425                 430
Ala Ile Ser Phe Ser Leu Thr Ala Glu His Ser Gly Asn Tyr Tyr Cys
            435                 440                 445
Thr Ala Asp Asn Gly Phe Gly Pro Gln Arg Ser Lys Ala Val Ser Leu
            450                 455                 460
Ser Val Thr Val Pro Val Ser His Pro Val Leu Thr Leu Ser Ser Ala
465                 470                 475                 480
Glu Ala Leu Thr Phe Glu Gly Ala Thr Val Thr Leu His Cys Glu Val
                    485                 490                 495
```

-continued

Gln Arg Gly Ser Pro Gln Ile Leu Tyr Gln Phe Tyr His Glu Asp Met
            500                 505                 510
Pro Leu Trp Ser Ser Ser Thr Pro Ser Val Gly Arg Val Ser Phe Ser
            515                 520                 525
Phe Ser Leu Thr Glu Gly His Ser Gly Asn Tyr Tyr Cys Thr Ala Asp
            530                 535                 540
Asn Gly Phe Gly Pro Gln Arg Ser Glu Val Val Ser Leu Phe Val Thr
545                 550                 555                 560
Val Pro Val Ser Arg Pro Ile Leu Thr Leu Arg Val Pro Arg Ala Gln
                565                 570                 575
Ala Val Val Gly Asp Leu Leu Glu Leu His Cys Glu Ala Pro Arg Gly
            580                 585                 590
Ser Pro Pro Ile Leu Tyr Trp Phe Tyr His Glu Asp Val Thr Leu Gly
            595                 600                 605
Ser Ser Ser Ala Pro Ser Gly Gly Glu Ala Ser Phe Asn Leu Ser Leu
            610                 615                 620
Thr Ala Glu His Ser Gly Asn Tyr Ser Cys Glu Ala Asn Asn Gly Leu
625                 630                 635                 640
Val Ala Gln His Ser Asp Thr Ile Ser Leu Ser Val Ile Val Pro Val
                645                 650                 655
Ser Arg Pro Ile Leu Thr Phe Arg Ala Pro Arg Ala Gln Ala Val Val
            660                 665                 670
Gly Asp Leu Leu Glu Leu His Cys Glu Ala Leu Arg Gly Ser Ser Pro
            675                 680                 685
Ile Leu Tyr Trp Phe Tyr His Glu Asp Val Thr Leu Gly Lys Ile Ser
            690                 695                 700
Ala Pro Ser Gly Gly Gly Ala Ser Phe Asn Leu Ser Leu Thr Thr Glu
705                 710                 715                 720
His Ser Gly Ile Tyr Ser Cys Glu Ala Asp Asn Gly Leu Glu Ala Gln
                725                 730                 735
Arg Ser Glu Met Val Thr Leu Lys Val Ala Val Pro Val Ser Arg Pro
            740                 745                 750
Val Leu Thr Leu Arg Ala Pro Gly Thr His Ala Ala Val Gly Asp Leu
            755                 760                 765
Leu Glu Leu His Cys Glu Ala Leu Arg Gly Ser Pro Leu Ile Leu Tyr
            770                 775                 780
Arg Phe Phe His Glu Asp Val Thr Leu Gly Asn Arg Ser Ser Pro Ser
785                 790                 795                 800
Gly Gly Ala Ser Leu Asn Leu Ser Leu Thr Ala Glu His Ser Gly Asn
                805                 810                 815
Tyr Ser Cys Glu Ala Asp Asn Gly Leu Gly Ala Gln Arg Ser Glu Thr
            820                 825                 830
Val Thr Leu Tyr Ile Thr Gly Leu Thr Ala Asn Arg Ser Gly Pro Phe
            835                 840                 845
Ala Thr Gly Val Ala Gly Gly Leu Leu Ser Ile Ala Gly Leu Ala Ala
            850                 855                 860
Gly Ala Leu Leu Leu Tyr Cys Trp Leu Ser Arg Lys Ala Gly Arg Lys
865                 870                 875                 880
Pro Ala Ser Asp Pro Ala Arg Ser Pro Ser Asp Ser Asp Ser Gln Glu
                885                 890                 895
Pro Thr Tyr His Asn Val Pro Ala Trp Glu Glu Leu Gln Pro Val Tyr
            900                 905                 910

```
Thr Asn Glu Glu Lys Met Trp Phe Thr Gln Lys Tyr Gly Ser Ser Lys
            915                 920                 925

Arg Lys Arg Asn Met Gln Trp Pro Leu Thr Pro Gly Ile Ser Gly Thr
    930                 935                 940

Arg Val Pro Leu Ser Ser Thr Leu Lys Leu Arg Trp Arg Gln Pro Arg
945                 950                 955                 960

Phe Pro Asp Pro Cys Ser Trp Leu Pro Gln Leu Leu Thr Asp Glu Ser
                965                 970                 975

Thr Arg Leu Ser Asn Cys Cys Phe Ser Leu Cys Thr Pro Lys Phe Pro
            980                 985                 990

Leu Gly Glu Lys Gln His
        995

<210> SEQ ID NO 37
<211> LENGTH: 5380
<212> TYPE: DNA
<213> ORGANISM: Homo sapiens

<400> SEQUENCE: 37
aattcactaa tgcattctgc tcttttgag agcacagctt ctcagatgtg ctccttggag      60
ctggtgtgca gtgtcctgac tgtaagatca agtccaaacc tgttttggaa ttgaggaaac    120
ttctcttttg atctcagccc ttggtggtcc aggtcttcat gctgctgtgg gtgatattac    180
tggtcctggc tcctgtcagt ggacagtttg caaggcacac caggcccatt atttcctcc     240 agcctccatg gaccacagtc ttccaaggag agagagtgac cctcacttgc aagggatttc    300
gcttctactc accacagaaa acaaaatggt accatcggta ccttgggaaa gaaatactaa    360
gagaaacccc agacaatatc cttgaggttc aggaatctgg agagtacaga tgccaggccc    420
agggctcccc tctcagtagc cctgtgcact tggattttc ttcagcttcg ctgatcctgc     480
aagctccact ttctgtgttt aaggagact ctgtggttct gaggtgccgg gcaaaggcgg     540
aagtaacact gaataatact atttacaaga atgataatgt cctggcattc cttaataaaa    600
gaactgactt ccatattcct catgcatgtc tcaaggacaa tggtgcatat cgctgtactg    660
gatataagga aagttgttgc cctgtttctt ccaatacagt caaaatccaa gtccaagagc    720
catttacacg tccagtgctg agagccagct ccttccagcc catcagcggg aacccagtga    780
ccctgacctg tgagacccag ctctctctag agaggtcaga tgtcccgctc cggttccgct    840
tcttcagaga tgaccagacc ctgggattag ctggagtct ctccccgaat tccagatta      900 ctgccatgtg gagtaaagat tcaggttct actggtgtaa ggcagcaaca atgcccttaca   960 gcgtcatatc tgacagcccg agatcctgga tacaggtgca gatccctgca tctcatcctg   1020
tcctcactct cagccctgaa aaggctctga attttgaggg aaccaaggtg cacttcact    1080 gtgaaaccca ggaagattct ctgcgcactt tgtacaggtt ttatcatgag ggtgtcccccc   1140 tgaggcacaa gtcagtccgc tgtgaaaggg gagcatccat cagcttctca ctgactacag   1200
agaattcagg gaactactac tgcacagctg acaatggcct tggcgccaag cccagtaagg   1260
ctgtgagcct ctcagtcact gttcccgtgt ctcatcctgt cctcaacctc agctctcctg   1320
aggacctgat ttttgaggga gccaaggtga cacttcactg tgaagcccag agaggttcac   1380
tccccatcct gtaccagttt catcatgagg gtgctgccct ggagcgtagg tcggccaact   1440
ctgcaggagg agtggccatc agcttctctc tgactgcaga gcattcaggg aactactact   1500
gcacagctga caatggcttt ggccccccagc gcagtaaggc ggtgagcctc tccgtcactg   1560
tccctgtgtc tcatcctgtc ctcaccctca gctctgctga ggccctgact tttgaaggag   1620
```

-continued

```
ccactgtgac acttcactgt gaagtccaga gaggttcccc acaaatccta taccagtttt    1680
atcatgagga catgcccctg tggagcagct caacaccctc tgtgggaaga gtgtccttca    1740
gcttctctct gactgaagga cattcaggga attactactg cacagctgac aatggctttg    1800
gtccccagcg cagtgaagtg gtgagccttt ttgtcactgt tccagtgtct cgccccatcc    1860
tcaccctcag ggttcccagg gcccaggctg tggtggggga cctgctggag cttcactgtg    1920
aggccccgag aggctctccc ccaatcctgt actggtttta tcatgaggat gtcaccctgg    1980
ggagcagctc agcccctct ggaggagaag cttctttcaa cctctctctg actgcagaac     2040
attctggaaa ctactcatgt gaggccaaca atggcctagt ggcccagcac agtgacacaa    2100
tatcactcag tgttatagtt ccagtatctc gtcccatcct caccttcagg gctcccaggg    2160
cccaggctgt ggtggggac ctgctggagc ttcactgtga ggcctgaga ggctcctccc      2220
caatcctgta ctggttttat catgaagatg tcaccctggg taagatctca gcccctctg    2280
gaggagggc ctccttcaac ctctctctga ctacagaaca ttctggaatc tactcctgtg    2340
aggcagacaa tggtctggag gcccagcgca gtgagatggt gacactgaaa gttgcagttc    2400
cggtgtctcg cccggtcctc accctcaggg ctccgggac ccatgctgcg gtgggggacc    2460
tgctggagct tcactgtgag gccctgagag gctctcccct gatcctgtac cggttttttc    2520
atgaggatgt caccctagga aataggtcgt cccctctgg aggagcgtcc ttaaacctct    2580
ctctgactgc agagcactct ggaaactact cctgtgaggc cgacaatggc ctcggggccc    2640
agcgcagtga gacagtgaca ctttatatca cagggctgac cgcgaacaga agtggccctt    2700
ttgccacagg agtcgccggg ggcctgctca gcatagcagg ccttgctgcg ggggcactgc    2760
tgctctactg ctggctctcg agaaaagcag ggagaaagcc tgcctctgac cccgccagga    2820
gcccttcaga ctcggactcc caagagccca cctatcacaa tgtaccagcc tgggaagagc    2880
tgcaaccagt gtacactaat gaggagaaaa tgtggtttac tcagaagtac ggatcatcca    2940
agagaaaaag aaacatgcag tggcctctga ccccaggcat ctcaggaaca agggttcccc    3000
tatcatctac tctgaagtta aggtggcgtc aaccccggtt tccggatccc tgttcttggc    3060
ttcctcagct cctcacagat gagtccacac gtctctccaa ctgctgtttc agcctctgca    3120
ccccaaagtt ccccttgggg gagaagcagc attgaagtgg gaagatttag gctgccccag    3180
accatatcta ctggcctttg tttcacatgt cctcattctc agtctgacca gaatgcaggg    3240
ccctgctgga ctgtcacctg tttcccagtt aaagccctga ctggcaggtt ttttaatcca    3300
gtggcaaggt gctcccactc cagggcccag cacatctcct ggattcctta gtgggcttca    3360
gctgtggttg ctgttctgag tactgctctc atcacacccc cacagagggg gtcttaccac    3420
acaaagggag agtgggcctt caggagatgc cgggctggcc taacagctca ggtgctccta    3480
aactccgaca cagagttcct gctttgggtg gatgcatttc tcaattgtca tcagcctggt    3540
ggggctactg cagtgtgctg ccaaatggga cagcacacag cctgtgcaca tgggacatgt    3600
gatgggtctc cccacggggg ctgcatttca cactcctcca cctgtctcaa actctaaggt    3660
cggcacttga caccaaggta acttctctcc tgctcatgtg tcagtgtcta cctgcccaag    3720
taagtggctt tcatacacca agtcccaagt tcttcccatc ctaacagaag taaccagca    3780
agtcaaggcc aggaggacca ggggtgcaga cagaacacat actggaacac aggaggtgct    3840
caattactat ttgactgact gactgaatga atgaatgaat gaggaagaaa actgtgggta    3900
atcaaactgg cataaaatcc agtgcactcc ctaggaaatc cgggaggtat tctggcttcc    3960
```

| | |
|---|---|
| ctaagaaaca atggaagaga aggagcttgg atgaggaaac tgttcagcaa gaggaagggc | 4020 |
| ttctcacact tcatgtgct tgtggatcac ctgaggatcc tgtgaaaata cagatactga | 4080 |
| ttcagtgggt ctgcgtagag cctgagactg ccattctaac atgttcccag gggatgctga | 4140 |
| tgctgctggc cctgggactg cactgcatgc atgtgaagcc ctataggtct cagcagaggc | 4200 |
| ccatggagag ggaatgtgtg gctctggctg cccagggccc aactcggttc acacggatcg | 4260 |
| tgctgctccc tggccagcct ttggccacag caccaccagc tgctgttgct gagagagctt | 4320 |
| cttctctgtg acatgttggc tttcatcagc caccctggga agcggaaagt agctgccact | 4380 |
| atctttgttt ccccacctca ggcctcacac tttcccatga aaagggtgaa tgtatataac | 4440 |
| ctgagccctc tccattcaga gttgttctcc catctctgag caatgggatg ttctgttccg | 4500 |
| cttttatgat atccatcaca tcttatcttg atctttgctc ccagtggatt gtacagtgat | 4560 |
| gacttttaag ccccacggcc ctgaaataaa atccttccaa gggcattgga agctcactcc | 4620 |
| acctgaacca tggcttttca tgcttccaag tgtcagggcc ttgcccagat agacagggct | 4680 |
| ggctctgctg ccccaacctt tcaaggagga accagacact gagacagg agcctgtatg | 4740 |
| cagcccagtg cagccttgca gaggacaagg ctggaggcat tgtcatcac tacagatatg | 4800 |
| caactaaaat agacgtggag caagagaaat gcattcccac cgaggccgct ttttaggcc | 4860 |
| tagttgaaag tcaagaagga cagcagcaag cataggctca ggattaaaga aaaaatctg | 4920 |
| ctcacagtct gttctggagg tcacatcacc aacaaagctc acgccctatg cagttctgag | 4980 |
| aaggtggagg caccaggctc aaaagaggaa atttagaatt tctcattggg agagtaaggt | 5040 |
| accccccatcc cagaatgata actgcacagt ggcagaacaa actccaccct aatgtgggtg | 5100 |
| gaccccgtcc agtctgttga aggcctgaat gtaacaaaag gcttattct tcctcaagta | 5160 |
| agggggaact cctgctttgg gctgggacat aagttttct gctttcagac gcaaactgaa | 5220 |
| aaatggctct tcttgggtct tgagcttgct ggcatatgga ctgaaagaaa ctatgctatt | 5280 |
| ggatctcctg gatctccagc ttgctgactg cagatcttga gatatgtcag cctctacagt | 5340 |
| cacaagagct aattcattct aataaaccaa tctttctgta | 5380 |

<210> SEQ ID NO 38
<211> LENGTH: 27
<212> TYPE: PRT
<213> ORGANISM: Homo sapiens

<400> SEQUENCE: 38

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 39
<211> LENGTH: 81
<212> TYPE: DNA
<213> ORGANISM: Homo sapiens

<400> SEQUENCE: 39
ttttgggtgc tggtggtggt tgtggagtc ctggcttgct atagcttgct agtaacagtg    60
gcctttatta ttttctgggt g                                            81

<210> SEQ ID NO 40
<211> LENGTH: 26
<212> TYPE: PRT
<213> ORGANISM: Homo sapiens

<400> SEQUENCE: 40

Val Met Ser Val Ala Thr Ile Val Ile Val Asp Ile Cys Ile Thr Gly
1               5                   10                  15

Gly Leu Leu Leu Leu Val Tyr Tyr Trp Ser
            20                  25

<210> SEQ ID NO 41
<211> LENGTH: 78
<212> TYPE: DNA
<213> ORGANISM: Homo sapiens

<400> SEQUENCE: 41
gtgatgtcgg tggccacaat tgtcatagtg gacatctgca tcactggggg cttgctgctg      60
ctggtttact actggagc                                                   78

<210> SEQ ID NO 42
<211> LENGTH: 22
<212> TYPE: PRT
<213> ORGANISM: Homo sapiens

<400> SEQUENCE: 42

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 43
<211> LENGTH: 66
<212> TYPE: DNA
<213> ORGANISM: Homo sapiens

<400> SEQUENCE: 43
atggccctga ttgtgctggg gggcgtcgcc ggcctcctgc ttttcattgg gctaggcatc      60
ttcttc                                                                66

<210> SEQ ID NO 44
<211> LENGTH: 30
<212> TYPE: PRT
<213> ORGANISM: Homo sapiens

<400> SEQUENCE: 44

Ala Gly Leu Ala Ala Gly Thr Val Ala Ser Ile Ile Leu Ala Leu Val
1               5                   10                  15

Leu Leu Val Val Leu Leu Val Val Cys Gly Pro Leu Ala Tyr
            20                  25                  30

<210> SEQ ID NO 45
<211> LENGTH: 90
<212> TYPE: DNA
<213> ORGANISM: Homo sapiens

<400> SEQUENCE: 45
gcaggcctgg ccgcaggcac ggtggcaagc atcatcctgg ccctggtgct cctggtggtg      60
ctgctggtcg tgtgcggccc ccttgcctac                                      90

<210> SEQ ID NO 46
<211> LENGTH: 21
<212> TYPE: PRT
<213> ORGANISM: Homo sapiens

<400> SEQUENCE: 46

Ile Pro Ser Ile Val Leu Gly Ile Leu Leu Gly Ser Leu Ile Phe
1               5                   10                  15

Ile Ala Phe Ile Leu
            20

<210> SEQ ID NO 47
<211> LENGTH: 63
<212> TYPE: DNA
<213> ORGANISM: Homo sapiens

<400> SEQUENCE: 47
atcccctcca tcgttctggg aattctcctc cttggctccc tcatcttcat agccttcatc    60
ctc                                                                 63

<210> SEQ ID NO 48
<211> LENGTH: 21
<212> TYPE: PRT
<213> ORGANISM: Homo sapiens

<400> SEQUENCE: 48

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 49
<211> LENGTH: 63
<212> TYPE: DNA
<213> ORGANISM: Homo sapiens

<400> SEQUENCE: 49
atctacatct gggcgccctt ggccgggact tgtggggtcc ttctcctgtc actggttatc    60
acc                                                                 63

<210> SEQ ID NO 50
<211> LENGTH: 21
<212> TYPE: PRT
<213> ORGANISM: Homo sapiens

<400> SEQUENCE: 50

Leu Leu Phe Gly Phe Asn Phe Ile Phe Trp Leu Ala Gly Ile Ala Val
1               5                   10                  15

Leu Ala Ile Gly Leu
            20

<210> SEQ ID NO 51
<211> LENGTH: 63
<212> TYPE: DNA
<213> ORGANISM: Homo sapiens

<400> SEQUENCE: 51
ctgctgttcg gatttaactt catcttctgg cttgccggga ttgctgtcct tgccattgga    60
cta                                                                 63

<210> SEQ ID NO 52
<211> LENGTH: 21
<212> TYPE: PRT
<213> ORGANISM: Homo sapiens

<400> SEQUENCE: 52

Phe Tyr Thr Gly Val Tyr Ile Leu Ile Gly Ala Gly Ala Leu Met Met
1               5                   10                  15

Leu Val Gly Phe Leu
            20

<210> SEQ ID NO 53
<211> LENGTH: 63
<212> TYPE: DNA
<213> ORGANISM: Homo sapiens

<400> SEQUENCE: 53
ttctacacag gagtctatat tctgatcgga gccggcgccc tcatgatgct ggtgggcttc    60
ctg                                                                 63

<210> SEQ ID NO 54
<211> LENGTH: 24
<212> TYPE: PRT
<213> ORGANISM: Homo sapiens

<400> SEQUENCE: 54

Met Leu Gly Leu Phe Phe Gly Phe Leu Leu Val Ile Phe Ala Ile Glu
1               5                   10                  15

Ile Ala Ala Ala Ile Trp Gly Tyr
            20

<210> SEQ ID NO 55
<211> LENGTH: 72
<212> TYPE: DNA
<213> ORGANISM: Homo sapiens

<400> SEQUENCE: 55
atgctgggac tgttcttcgg cttcctcttg gtgatattcg ccattgaaat agctgcggcc    60
atctggggat at                                                       72

<210> SEQ ID NO 56
<211> LENGTH: 26
<212> TYPE: PRT
<213> ORGANISM: Homo sapiens

<400> SEQUENCE: 56

Ile Gly Ala Val Gly Ile Gly Ile Ala Val Val Met Ile Phe Gly Met
1               5                   10                  15

Ile Phe Ser Met Ile Leu Cys Cys Ala Ile
            20                  25

<210> SEQ ID NO 57
<211> LENGTH: 78
<212> TYPE: DNA
<213> ORGANISM: Homo sapiens

<400> SEQUENCE: 57
atcggcgcag tgggcatcgg cattgccgtg gtcatgatat ttggcatgat cttcagtatg    60
atcttgtgct gtgctatc                                                 78

<210> SEQ ID NO 58
<211> LENGTH: 21
<212> TYPE: PRT
<213> ORGANISM: Homo sapiens

<400> SEQUENCE: 58

```
Val Ser Phe Cys Leu Val Met Val Leu Leu Phe Ala Val Asp Thr Gly
1               5                   10                  15

Leu Tyr Phe Ser Val
            20

<210> SEQ ID NO 59
<211> LENGTH: 19
<212> TYPE: PRT
<213> ORGANISM: Homo sapiens

<400> SEQUENCE: 59

Val Ala Val Gly Leu Gly Ser Cys Leu Ala Ile Leu Ile Leu Ala Ile
1               5                   10                  15

Cys Gly Leu

<210> SEQ ID NO 60
<211> LENGTH: 23
<212> TYPE: PRT
<213> ORGANISM: Homo sapiens

<400> SEQUENCE: 60

Gly Ala Ile Gly Gly Ala Gly Val Thr Ala Leu Leu Ala Leu Cys Leu
1               5                   10                  15

Cys Leu Ile Phe Phe Ile Val
            20

<210> SEQ ID NO 61
<211> LENGTH: 15
<212> TYPE: PRT
<213> ORGANISM: Homo sapiens

<400> SEQUENCE: 61

Val Leu Ala Ile Ser Gly Ile Phe Thr Met Gly Ile Ala Leu Leu
1               5                   10                  15

<210> SEQ ID NO 62
<211> LENGTH: 45
<212> TYPE: DNA
<213> ORGANISM: Homo sapiens

<400> SEQUENCE: 62
gtcctggcca tctcaggaat cttcaccatg ggcatcgccc tcctg          45

<210> SEQ ID NO 63
<211> LENGTH: 26
<212> TYPE: PRT
<213> ORGANISM: Homo sapiens

<400> SEQUENCE: 63

Leu Leu Gly Leu Tyr Phe Gly Met Leu Leu Leu Phe Ala Thr Gln
1               5                   10                  15

Ile Thr Leu Gly Ile Leu Ile Ser Thr Gln
            20                  25

<210> SEQ ID NO 64
<211> LENGTH: 78
<212> TYPE: DNA
<213> ORGANISM: Homo sapiens

<400> SEQUENCE: 64
ctcctgggcc tgtatttttgg gatgctgctg ctcctgtttg ccacacagat caccctggga    60
atcctcatct ccactcag                                                   78
```

<210> SEQ ID NO 65
<211> LENGTH: 25
<212> TYPE: PRT
<213> ORGANISM: Homo sapiens

<400> SEQUENCE: 65

Leu Ile Ser Ile Val Gly Ile Cys Leu Gly Val Gly Leu Leu Glu Leu
1               5                   10                  15

Gly Phe Met Thr Leu Ser Ile Phe Leu
            20                  25

<210> SEQ ID NO 66
<211> LENGTH: 75
<212> TYPE: DNA
<213> ORGANISM: Homo sapiens

<400> SEQUENCE: 66
cttatttcca tagtgggcat ttgcctgggc gtcggcctac tcgagctcgg gttcatgacg    60
ctctcgatat tcctg                                                    75

<210> SEQ ID NO 67
<211> LENGTH: 21
<212> TYPE: PRT
<213> ORGANISM: Homo sapiens

<400> SEQUENCE: 67

Phe Asn Leu Phe Phe Val Leu Gly Ser Leu Ile Phe Cys Phe Gly
1               5                   10                  15

Ile Trp Ile Leu Ile
            20

<210> SEQ ID NO 68
<211> LENGTH: 63
<212> TYPE: DNA
<213> ORGANISM: Homo sapiens

<400> SEQUENCE: 68
ttcaacctct tcttcttcgt cctcggcagc ctgatcttct gcttcggcat ctggatcctc    60
att                                                                 63

<210> SEQ ID NO 69
<211> LENGTH: 21
<212> TYPE: PRT
<213> ORGANISM: Homo sapiens

<400> SEQUENCE: 69

Val Leu Phe Tyr Leu Ala Val Gly Ile Met Phe Leu Val Asn Thr Val
1               5                   10                  15

Leu Trp Val Thr Ile
            20

<210> SEQ ID NO 70
<211> LENGTH: 63
<212> TYPE: DNA
<213> ORGANISM: Homo sapiens

<400> SEQUENCE: 70
gtccttttct atctggcagt gggaataatg ttttagtga acactgttct ctgggtgaca    60
ata                                                                 63

```
<210> SEQ ID NO 71
<211> LENGTH: 21
<212> TYPE: PRT
<213> ORGANISM: Homo sapiens

<400> SEQUENCE: 71

Leu Leu Pro Ser Trp Ala Ile Thr Leu Ile Ser Val Asn Gly Ile Phe
1               5                   10                  15

Val Ile Cys Cys Leu
            20

<210> SEQ ID NO 72
<211> LENGTH: 63
<212> TYPE: DNA
<213> ORGANISM: Homo sapiens

<400> SEQUENCE: 72
ctgctcccat cctgggccat taccttaatc tcagtaaatg gaattttgt gatatgctgc      60 ctg                                                                  63

<210> SEQ ID NO 73
<211> LENGTH: 21
<212> TYPE: PRT
<213> ORGANISM: Homo sapiens

<400> SEQUENCE: 73

Trp Ile Thr Ala Val Leu Pro Thr Val Ile Ile Cys Val Met Val Phe
1               5                   10                  15

Cys Leu Ile Leu Trp
            20

<210> SEQ ID NO 74
<211> LENGTH: 21
<212> TYPE: PRT
<213> ORGANISM: Homo sapiens

<400> SEQUENCE: 74

Val Ala Ala Ile Leu Gly Leu Gly Leu Val Leu Gly Leu Leu Gly Pro
1               5                   10                  15

Leu Ala Ile Leu Leu
            20

<210> SEQ ID NO 75
<211> LENGTH: 63
<212> TYPE: DNA
<213> ORGANISM: Homo sapiens

<400> SEQUENCE: 75
gttgccgcca tcctgggcct gggcctggtg ctggggctgc tgggccccct ggccatcctg     60
ctg                                                                  63

<210> SEQ ID NO 76
<211> LENGTH: 27
<212> TYPE: PRT
<213> ORGANISM: Homo sapiens

<400> SEQUENCE: 76

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25
```

<210> SEQ ID NO 77
<211> LENGTH: 81
<212> TYPE: DNA
<213> ORGANISM: Homo sapiens

<400> SEQUENCE: 77
atcatctcct tctttcttgc gctgacgtcg actgcgttgc tcttcctgct gttcttcctc    60
acgctccgtt tctctgttgt t                                              81

<210> SEQ ID NO 78
<211> LENGTH: 24
<212> TYPE: PRT
<213> ORGANISM: Homo sapiens

<400> SEQUENCE: 78

Ile Phe Met Tyr Leu Leu Thr Val Phe Leu Ile Thr Gln Met Ile Gly
1               5                   10                  15

Ser Ala Leu Phe Ala Val Tyr Leu
            20

<210> SEQ ID NO 79
<211> LENGTH: 72
<212> TYPE: DNA
<213> ORGANISM: Homo sapiens

<400> SEQUENCE: 79 attttatgt atttacttac tgtttttctt atcacccaga tgattgggtc agcactttt    60 gctgtgtatc tt                                                        72

<210> SEQ ID NO 80
<211> LENGTH: 39
<212> TYPE: PRT
<213> ORGANISM: Homo sapiens

<400> SEQUENCE: 80

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 81
<211> LENGTH: 45
<212> TYPE: PRT
<213> ORGANISM: Homo sapiens

<400> SEQUENCE: 81

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 82
<211> LENGTH: 135
<212> TYPE: DNA
<213> ORGANISM: Homo sapiens

<400> SEQUENCE: 82

```
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                    135
```

<210> SEQ ID NO 83
<211> LENGTH: 230
<212> TYPE: PRT
<213> ORGANISM: Homo sapiens

<400> SEQUENCE: 83

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys Met
225                 230
```

<210> SEQ ID NO 84
<211> LENGTH: 690
<212> TYPE: DNA
<213> ORGANISM: Homo sapiens

<400> SEQUENCE: 84

```
gagagcaagt acggccctcc ctgcccccct tgccctgccc ccgagttcct gggcggaccc    60
agcgtgttcc tgttcccccc caagcccaag acaccctga tgatcagccg gacccccgag   120
gtgacctgtg tggtggtgga cgtgtcccag gaggaccccg aggtccagtt caactggtac   180
gtggacggcg tggaggtgca caacgccaag accaagcccc gggaggagca gttcaatagc   240
acctaccggg tggtgtccgt gctgaccgtg ctgcaccagg actggctgaa cggcaaggaa   300
```

```
tacaagtgta aggtgtccaa caagggcctg cccagcagca tcgagaaaac catcagcaag    360
gccaagggcc agcctcggga gccccaggtg tacaccctgc ccctagccca agaggagatg    420
accaagaacc aggtgtccct gacctgcctg gtgaagggct tctaccccag cgacatcgcc    480
gtggagtggg agagcaacgg ccagcccgag aacaactaca agaccacccc ccctgtgctg    540
gacagcgacg gcagcttctt cctgtacagc cggctgaccg tggacaagag ccggtggcag    600
gagggcaacg tctttagctg ctccgtgatg cacgaggccc tgcacaacca ctacacccag    660
aagagcctga gcctgtccct gggcaagatg                                     690

<210> SEQ ID NO 85
<211> LENGTH: 112
<212> TYPE: PRT
<213> ORGANISM: Homo sapiens

<400> SEQUENCE: 85

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 86
<211> LENGTH: 42
<212> TYPE: PRT
<213> ORGANISM: Homo sapiens

<400> SEQUENCE: 86

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 87
<211> LENGTH: 126
<212> TYPE: DNA
<213> ORGANISM: Homo sapiens

<400> SEQUENCE: 87
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                               126

<210> SEQ ID NO 88
<211> LENGTH: 41
<212> TYPE: PRT
<213> ORGANISM: Homo sapiens
```

<400> SEQUENCE: 88

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 89
<211> LENGTH: 93
<212> TYPE: PRT
<213> ORGANISM: Homo sapiens

<400> SEQUENCE: 89

Lys Lys Leu Val Lys Lys Phe Arg Gln Lys Lys Gln Arg Gln Trp Ile
1               5                   10                  15

Gly Pro Thr Gly Met Asn Gln Asn Met Ser Phe His Arg Asn His Thr
            20                  25                  30

Ala Thr Val Arg Ser His Ala Glu Asn Pro Thr Ala Ser His Val Asp
        35                  40                  45

Asn Glu Tyr Ser Gln Pro Pro Arg Asn Ser His Leu Ser Ala Tyr Pro
50                  55                  60

Ala Leu Glu Gly Ala Leu His Arg Ser Ser Met Gln Pro Asp Asn Ser
65                  70                  75                  80

Ser Asp Ser Asp Tyr Asp Leu His Gly Ala Gln Arg Leu
                85                  90

<210> SEQ ID NO 90
<211> LENGTH: 141
<212> TYPE: PRT
<213> ORGANISM: Homo sapiens

<400> SEQUENCE: 90

Lys Leu Gln Arg Arg Trp Lys Arg Thr Gln Ser Gln Gln Gly Leu Gln
1               5                   10                  15

Glu Asn Ser Ser Gly Gln Ser Phe Phe Val Arg Asn Lys Lys Val Arg
            20                  25                  30

Arg Ala Pro Leu Ser Glu Gly Pro His Ser Leu Gly Cys Tyr Asn Pro
        35                  40                  45

Met Met Glu Asp Gly Ile Ser Tyr Thr Thr Leu Arg Phe Pro Glu Met
50                  55                  60

Asn Ile Pro Arg Thr Gly Asp Ala Glu Ser Ser Glu Met Gln Arg Pro
65                  70                  75                  80

Pro Pro Asp Cys Asp Asp Thr Val Thr Tyr Ser Ala Leu His Lys Arg
                85                  90                  95

Gln Val Gly Asp Tyr Glu Asn Val Ile Pro Asp Phe Pro Glu Asp Glu
            100                 105                 110

Gly Ile His Tyr Ser Glu Leu Ile Gln Phe Gly Val Gly Glu Arg Pro
        115                 120                 125

Gln Ala Gln Glu Asn Val Asp Tyr Val Ile Leu Lys His
    130                 135                 140

<210> SEQ ID NO 91
<211> LENGTH: 61
<212> TYPE: PRT
<213> ORGANISM: Homo sapiens

```
<400> SEQUENCE: 91

Arg Lys Arg Trp Gln Asn Glu Lys Leu Gly Leu Asp Ala Gly Asp Glu
1               5                   10                  15

Tyr Glu Asp Glu Asn Leu Tyr Glu Gly Leu Asn Leu Asp Asp Cys Ser
                20                  25                  30

Met Tyr Glu Asp Ile Ser Arg Gly Leu Gln Gly Thr Tyr Gln Asp Val
            35                  40                  45

Gly Ser Leu Asn Ile Gly Asp Val Gln Leu Glu Lys Pro
        50                  55                  60

<210> SEQ ID NO 92
<211> LENGTH: 42
<212> TYPE: PRT
<213> ORGANISM: Homo sapiens

<400> SEQUENCE: 92

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 93
<211> LENGTH: 41
<212> TYPE: PRT
<213> ORGANISM: Homo sapiens

<400> SEQUENCE: 93

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 94
<211> LENGTH: 40
<212> TYPE: PRT
<213> ORGANISM: Homo sapiens

<400> SEQUENCE: 94

Cys Val Arg Cys Arg His Arg Arg Gln Ala Glu Arg Met Ser Gln
1               5                   10                  15

Ile Lys Arg Leu Leu Ser Glu Lys Lys Thr Cys Gln Cys Pro His Arg
                20                  25                  30

Phe Gln Lys Thr Cys Ser Pro Ile
            35                  40

<210> SEQ ID NO 95
<211> LENGTH: 48
<212> TYPE: PRT
<213> ORGANISM: Homo sapiens

<400> SEQUENCE: 95

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
                20                  25                  30
```

Ile Pro Ile Gln Glu Asp Tyr Arg Lys Pro Glu Pro Ala Cys Ser Pro
                35                  40                  45

<210> SEQ ID NO 96
<211> LENGTH: 32
<212> TYPE: PRT
<213> ORGANISM: Homo sapiens

<400> SEQUENCE: 96

Leu Tyr Cys Asn His Arg Asn Arg Arg Val Cys Lys Cys Pro Arg
1               5                   10                  15

Pro Val Val Lys Ser Gly Asp Lys Pro Ser Leu Ser Ala Arg Tyr Val
                20                  25                  30

<210> SEQ ID NO 97
<211> LENGTH: 116
<212> TYPE: PRT
<213> ORGANISM: Homo sapiens

<400> SEQUENCE: 97

Lys Arg Lys Lys Gln Arg Ser Arg Arg Asn Asp Glu Glu Leu Glu Thr
1               5                   10                  15

Arg Ala His Arg Val Ala Thr Glu Glu Arg Gly Arg Lys Pro His Gln
                20                  25                  30

Ile Pro Ala Ser Thr Pro Gln Asn Pro Ala Thr Ser Gln His Pro Pro
            35                  40                  45

Pro Pro Pro Gly His Arg Ser Gln Ala Pro Ser His Arg Pro Pro Pro
        50                  55                  60

Pro Gly His Arg Val Gln His Gln Pro Gln Lys Arg Pro Pro Ala Pro
65                  70                  75                  80

Ser Gly Thr Gln Val His Gln Gln Lys Gly Pro Pro Leu Pro Arg Pro
                85                  90                  95

Arg Val Gln Pro Lys Pro Pro His Gly Ala Ala Glu Asn Ser Leu Ser
                100                 105                 110

Pro Ser Ser Asn
            115

<210> SEQ ID NO 98
<211> LENGTH: 42
<212> TYPE: PRT
<213> ORGANISM: Homo sapiens

<400> SEQUENCE: 98

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 99
<211> LENGTH: 126
<212> TYPE: DNA
<213> ORGANISM: Homo sapiens

<400> SEQUENCE: 99
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

-continued

```
<210> SEQ ID NO 100
<211> LENGTH: 18
<212> TYPE: PRT
<213> ORGANISM: Artificial
<220> FEATURE:
<223> OTHER INFORMATION: Whitlow Linker

<400> SEQUENCE: 100

Gly Ser Thr Ser Gly Ser Gly Lys Pro Gly Ser Gly Glu Gly Ser Thr
1               5                   10                  15

Lys Gly

<210> SEQ ID NO 101
<211> LENGTH: 11
<212> TYPE: PRT
<213> ORGANISM: Artificial
<220> FEATURE:
<223> OTHER INFORMATION: CDR1 of SEQ ID NO: 1

<400> SEQUENCE: 101

Ser Ala Ser Gln Asp Ile Ser Asn Tyr Leu Asn
1               5                   10

<210> SEQ ID NO 102
<211> LENGTH: 7
<212> TYPE: PRT
<213> ORGANISM: Artificial
<220> FEATURE:
<223> OTHER INFORMATION: CDR2 of SEQ ID NO: 1

<400> SEQUENCE: 102

Tyr Thr Ser Asn Leu His Ser
1               5

<210> SEQ ID NO 103
<211> LENGTH: 9
<212> TYPE: PRT
<213> ORGANISM: Artificial
<220> FEATURE:
<223> OTHER INFORMATION: CDR3 of SEQ ID NO: 1

<400> SEQUENCE: 103

Gln Gln Tyr Arg Lys Leu Pro Trp Thr
1               5

<210> SEQ ID NO 104
<211> LENGTH: 5
<212> TYPE: PRT
<213> ORGANISM: Artificial
<220> FEATURE:
<223> OTHER INFORMATION: CDR1 of SEQ ID NO: 2

<400> SEQUENCE: 104

Asn Tyr Trp Met His
1               5

<210> SEQ ID NO 105
<211> LENGTH: 17
<212> TYPE: PRT
<213> ORGANISM: Artificial
<220> FEATURE:
<223> OTHER INFORMATION: CDR2 of SEQ ID NO: 2

<400> SEQUENCE: 105

Ala Thr Tyr Arg Gly His Ser Asp Thr Tyr Tyr Asn Gln Lys Phe Lys
```

```
1               5                   10                  15
Gly

<210> SEQ ID NO 106
<211> LENGTH: 12
<212> TYPE: PRT
<213> ORGANISM: Artificial
<220> FEATURE:
<223> OTHER INFORMATION: CDR3 of SEQ ID NO: 2

<400> SEQUENCE: 106

Gly Ala Ile Tyr Asp Gly Tyr Asp Val Leu Asp Asn
1               5                   10

<210> SEQ ID NO 107
<211> LENGTH: 11
<212> TYPE: PRT
<213> ORGANISM: Artificial
<220> FEATURE:
<223> OTHER INFORMATION: CDR1 of SEQ ID NO: 5

<400> SEQUENCE: 107

Lys Ala Ser Gln Asp Val Ser Thr Ala Val Ala
1               5                   10

<210> SEQ ID NO 108
<211> LENGTH: 7
<212> TYPE: PRT
<213> ORGANISM: Artificial
<220> FEATURE:
<223> OTHER INFORMATION: CDR2 of SEQ ID NO: 5

<400> SEQUENCE: 108

Ser Ala Ser Tyr Arg Tyr Thr
1               5

<210> SEQ ID NO 109
<211> LENGTH: 9
<212> TYPE: PRT
<213> ORGANISM: Artificial
<220> FEATURE:
<223> OTHER INFORMATION: CDR3 of SEQ ID NO: 5

<400> SEQUENCE: 109

Gln Gln His Phe Ser Ser Pro Arg Thr
1               5

<210> SEQ ID NO 110
<211> LENGTH: 10
<212> TYPE: PRT
<213> ORGANISM: Artificial
<220> FEATURE:
<223> OTHER INFORMATION: CDR1 of SEQ ID NO: 6

<400> SEQUENCE: 110

Gly Phe Thr Phe Ser Ser Tyr Ala Val Ser
1               5                   10

<210> SEQ ID NO 111
<211> LENGTH: 17
<212> TYPE: PRT
<213> ORGANISM: Artificial
<220> FEATURE:
<223> OTHER INFORMATION: CDR2 of SEQ ID NO: 6

<400> SEQUENCE: 111
```

```
Ala Thr Ile Ser Ser Gly Gly Ser Leu Thr Phe Tyr Leu Asp Ser Val
1               5                   10                  15

Arg

<210> SEQ ID NO 112
<211> LENGTH: 10
<212> TYPE: PRT
<213> ORGANISM: Artificial
<220> FEATURE:
<223> OTHER INFORMATION: CDR3 of SEQ ID NO: 6

<400> SEQUENCE: 112

Pro Ile Pro Asp Tyr Tyr Ala Leu Asp Tyr
1               5                   10

<210> SEQ ID NO 113
<211> LENGTH: 11
<212> TYPE: PRT
<213> ORGANISM: Artificial
<220> FEATURE:
<223> OTHER INFORMATION: CDR1 of SEQ ID NO: 9

<400> SEQUENCE: 113

Lys Ala Ser Gln Asp Val Ser Thr Ala Val Ala
1               5                   10

<210> SEQ ID NO 114
<211> LENGTH: 7
<212> TYPE: PRT
<213> ORGANISM: Artificial
<220> FEATURE:
<223> OTHER INFORMATION: CDR2 of SEQ ID NO: 9

<400> SEQUENCE: 114

Ser Ala Ser Tyr Arg Tyr Thr
1               5

<210> SEQ ID NO 115
<211> LENGTH: 9
<212> TYPE: PRT
<213> ORGANISM: Artificial
<220> FEATURE:
<223> OTHER INFORMATION: CDR13  of SEQ ID NO: 9

<400> SEQUENCE: 115

Gln Gln His Phe Ser Ser Pro Arg Thr
1               5

<210> SEQ ID NO 116
<211> LENGTH: 10
<212> TYPE: PRT
<213> ORGANISM: Artificial
<220> FEATURE:
<223> OTHER INFORMATION: CDR1 of SEQ ID NO: 10

<400> SEQUENCE: 116

Gly Phe Thr Phe Ser Ser Tyr Ala Val Ser
1               5                   10

<210> SEQ ID NO 117
<211> LENGTH: 17
<212> TYPE: PRT
<213> ORGANISM: Artificial
<220> FEATURE:
<223> OTHER INFORMATION: CDR2 of SEQ ID NO: 10

<400> SEQUENCE: 117
```

```
Ala Thr Ile Ser Ser Gly Gly Ser Leu Thr Phe Tyr Leu Asp Ser Val
1               5                   10                  15
Arg

<210> SEQ ID NO 118
<211> LENGTH: 10
<212> TYPE: PRT
<213> ORGANISM: Artificial
<220> FEATURE:
<223> OTHER INFORMATION: CDR3 of SEQ ID NO: 10

<400> SEQUENCE: 118

Pro Ile Pro Asp Tyr Tyr Ala Leu Asp Tyr
1               5                   10

<210> SEQ ID NO 119
<211> LENGTH: 11
<212> TYPE: PRT
<213> ORGANISM: Artificial
<220> FEATURE:
<223> OTHER INFORMATION: CDR1 of SEQ ID NO: 13

<400> SEQUENCE: 119

Lys Ala Ser Gln Asp Val Arg Asn Leu Val Val
1               5                   10

<210> SEQ ID NO 120
<211> LENGTH: 6
<212> TYPE: PRT
<213> ORGANISM: Artificial
<220> FEATURE:
<223> OTHER INFORMATION: CDR2 of SEQ ID NO: 13

<400> SEQUENCE: 120

Ser Gly Ser Tyr Arg Tyr
1               5

<210> SEQ ID NO 121
<211> LENGTH: 9
<212> TYPE: PRT
<213> ORGANISM: Artificial
<220> FEATURE:
<223> OTHER INFORMATION: CDR3 of SEQ ID NO: 13

<400> SEQUENCE: 121

Gln Gln His Tyr Ser Pro Pro Tyr Thr
1               5

<210> SEQ ID NO 122
<211> LENGTH: 5
<212> TYPE: PRT
<213> ORGANISM: Artificial
<220> FEATURE:
<223> OTHER INFORMATION: CDR1 of SEQ ID NO: 14

<400> SEQUENCE: 122

Arg Phe Gly Val His
1               5

<210> SEQ ID NO 123
<211> LENGTH: 16
<212> TYPE: PRT
<213> ORGANISM: Artificial
<220> FEATURE:
<223> OTHER INFORMATION: CDR2 of SEQ ID NO: 14
```

```
<400> SEQUENCE: 123

Val Ile Trp Arg Gly Gly Ser Thr Asp Tyr Asn Ala Ala Phe Val Ser
1               5                   10                  15

<210> SEQ ID NO 124
<211> LENGTH: 12
<212> TYPE: PRT
<213> ORGANISM: Artificial
<220> FEATURE:
<223> OTHER INFORMATION: CDR3 of SEQ ID NO: 14

<400> SEQUENCE: 124

His Tyr Tyr Gly Ser Ser Asp Tyr Ala Leu Asp Asn
1               5                   10

<210> SEQ ID NO 125
<211> LENGTH: 11
<212> TYPE: PRT
<213> ORGANISM: Artificial
<220> FEATURE:
<223> OTHER INFORMATION: CDR1 of SEQ ID NO: 17

<400> SEQUENCE: 125

Lys Ala Ser Gln Asp Val Ser Asn Leu Val Val
1               5                   10

<210> SEQ ID NO 126
<211> LENGTH: 7
<212> TYPE: PRT
<213> ORGANISM: Artificial
<220> FEATURE:
<223> OTHER INFORMATION: CDR2 of SEQ ID NO: 17

<400> SEQUENCE: 126

Ser Gly Ser Tyr Arg Tyr Ser
1               5

<210> SEQ ID NO 127
<211> LENGTH: 9
<212> TYPE: PRT
<213> ORGANISM: Artificial
<220> FEATURE:
<223> OTHER INFORMATION: CDR3 of SEQ ID NO: 17

<400> SEQUENCE: 127

Gln Gln His Tyr Ser Pro Pro Tyr Thr
1               5

<210> SEQ ID NO 128
<211> LENGTH: 5
<212> TYPE: PRT
<213> ORGANISM: Artificial
<220> FEATURE:
<223> OTHER INFORMATION: CDR1 of SEQ ID NO: 18

<400> SEQUENCE: 128

Arg Phe Gly Val His
1               5

<210> SEQ ID NO 129
<211> LENGTH: 14
<212> TYPE: PRT
<213> ORGANISM: Artificial
<220> FEATURE:
<223> OTHER INFORMATION: CDR2 of SEQ ID NO: 18

<400> SEQUENCE: 129
```

```
Ile Trp Arg Gly Gly Ser Thr Asp Tyr Asn Ala Ala Phe Val
1               5                   10

<210> SEQ ID NO 130
<211> LENGTH: 12
<212> TYPE: PRT
<213> ORGANISM: Artificial
<220> FEATURE:
<223> OTHER INFORMATION: CDR3 of SEQ ID NO: 18

<400> SEQUENCE: 130

His Tyr Tyr Gly Ser Pro Asp Tyr Ala Leu Asp Asn
1               5                   10
```